(12) United States Patent
Saadat

(10) Patent No.: US 7,918,787 B2
(45) Date of Patent: Apr. 5, 2011

(54) TISSUE VISUALIZATION AND MANIPULATION SYSTEMS

(75) Inventor: Vahid Saadat, Atherton, CA (US)

(73) Assignee: Voyage Medical, Inc., Redwood City, CA (US)

( * ) Notice: Subject to any disclaimer, the term of this patent is extended or adjusted under 35 U.S.C. 154(b) by 907 days.

(21) Appl. No.: 11/687,597

(22) Filed: Mar. 16, 2007

(65) Prior Publication Data

US 2007/0287886 A1    Dec. 13, 2007

Related U.S. Application Data

(63) Continuation-in-part of application No. 11/259,498, filed on Oct. 25, 2005.

(60) Provisional application No. 60/783,494, filed on Mar. 17, 2006, provisional application No. 60/649,246, filed on Feb. 2, 2005.

(51) Int. Cl.
*A61B 1/00* (2006.01)
*A61B 6/00* (2006.01)

(52) U.S. Cl. .......................... 600/129; 600/127; 600/476

(58) Field of Classification Search .................. 600/114, 600/127, 129, 156, 476, 115, 116
See application file for complete search history.

(56) References Cited

U.S. PATENT DOCUMENTS

| | | | |
|---|---|---|---|
| 623,022 A | 4/1899 | Johnson | |
| 3,874,388 A | 4/1975 | King et al. | |
| 4,175,545 A | 11/1979 | Termanini | |
| 4,326,529 A | 4/1982 | Doss et al. | |
| 4,445,892 A | 5/1984 | Hussein et al. | |
| 4,470,407 A | 9/1984 | Hussein | |
| 4,619,247 A * | 10/1986 | Inoue et al. | 600/116 |
| 4,676,258 A | 6/1987 | Inokuchi et al. | |
| 4,681,093 A * | 7/1987 | Ono et al. | 600/116 |
| 4,709,698 A | 12/1987 | Johnston et al. | |
| 4,710,192 A | 12/1987 | Liotta et al. | |
| 4,784,133 A * | 11/1988 | Mackin | 606/7 |
| 4,911,148 A * | 3/1990 | Sosnowski et al. | 600/136 |

(Continued)

FOREIGN PATENT DOCUMENTS

DE    10028155 A1    12/2000

(Continued)

OTHER PUBLICATIONS

Avitall, A Catheter System to Ablate Atrial Fibrillation in a Sterile Pericarditis Dog Model, PACE, vol. 17, p. 774, 1994.

(Continued)

*Primary Examiner* — Linda C Dvorak
*Assistant Examiner* — Alireza Nia
(74) *Attorney, Agent, or Firm* — Levine Bagade Han LLP

(57) ABSTRACT

Tissue visualization and manipulation systems are described herein. Such a system may include a deployment catheter and an attached imaging hood deployable into an expanded configuration. In use, the imaging hood is placed against or adjacent to a region of tissue to be imaged in a body lumen that is normally filled with an opaque bodily fluid such as blood. A translucent or transparent fluid, such as saline, can be pumped into the imaging hood until the fluid displaces any blood, thereby leaving a clear region of tissue to be imaged via an imaging element in the deployment catheter. Additionally, any number of therapeutic tools can also be passed through the deployment catheter and into the imaging hood for treating the tissue region of interest.

21 Claims, 57 Drawing Sheets

U.S. PATENT DOCUMENTS

| | | | |
|---|---|---|---|
| 4,914,521 A | 4/1990 | Adair | |
| 4,943,290 A | 7/1990 | Rexroth et al. | |
| 4,950,285 A | 8/1990 | Wilk | |
| 4,961,738 A | 10/1990 | Mackin | |
| 4,976,710 A | 12/1990 | Mackin | |
| 4,994,069 A | 2/1991 | Ritchart et al. | |
| 4,998,916 A | 3/1991 | Hammerslag et al. | |
| 4,998,972 A | 3/1991 | Chin et al. | |
| 5,057,106 A | 10/1991 | Kasevich et al. | |
| 5,090,959 A | 2/1992 | Samson et al. | |
| 5,123,428 A | 6/1992 | Schwarz | |
| RE34,002 E | 7/1992 | Adair | |
| 5,171,259 A | 12/1992 | Inoue | |
| 5,281,238 A | 1/1994 | Chin et al. | |
| 5,282,827 A | 2/1994 | Kensey et al. | |
| 5,306,234 A | 4/1994 | Johnson | |
| 5,313,943 A | 5/1994 | Houser et al. | |
| 5,334,193 A | 8/1994 | Nardella | |
| 5,348,554 A | 9/1994 | Imran et al. | |
| 5,353,792 A | 10/1994 | Lubbers et al. | |
| 5,370,647 A | 12/1994 | Graber et al. | |
| 5,373,840 A | 12/1994 | Knighton | |
| 5,375,612 A | 12/1994 | Cottenceau et al. | |
| 5,385,148 A | 1/1995 | Lesh et al. | |
| 5,403,326 A | 4/1995 | Harrison et al. | |
| 5,421,338 A | 6/1995 | Crowley et al. | |
| 5,431,649 A | 7/1995 | Mulier et al. | |
| 5,453,785 A | 9/1995 | Lenhardt et al. | |
| 5,462,521 A | 10/1995 | Brucker et al. | |
| 5,471,515 A | 11/1995 | Fossum et al. | |
| 5,498,230 A | 3/1996 | Adair | |
| 5,505,730 A | 4/1996 | Edwards | |
| 5,515,853 A | 5/1996 | Smith et al. | |
| 5,527,338 A | 6/1996 | Purdy | |
| 5,549,603 A | 8/1996 | Feiring | |
| 5,571,088 A | 11/1996 | Lennox et al. | |
| 5,575,756 A * | 11/1996 | Karasawa et al. | 600/157 |
| 5,575,810 A | 11/1996 | Swanson et al. | |
| 5,584,872 A | 12/1996 | LaFontaine et al. | |
| 5,591,119 A | 1/1997 | Adair | |
| 5,593,405 A | 1/1997 | Osypka | |
| 5,593,422 A | 1/1997 | Muijs Van de Moer et al. | |
| 5,593,424 A | 1/1997 | Northrup, III | |
| 5,672,153 A | 9/1997 | Lax et al. | |
| 5,676,693 A | 10/1997 | LaFontaine | |
| 5,681,308 A | 10/1997 | Edwards et al. | |
| 5,695,448 A * | 12/1997 | Kimura et al. | 600/121 |
| 5,697,281 A | 12/1997 | Eggers et al. | |
| 5,697,882 A | 12/1997 | Eggers et al. | |
| 5,709,224 A | 1/1998 | Behl et al. | |
| 5,713,907 A | 2/1998 | Hogendijk et al. | |
| 5,713,946 A | 2/1998 | Ben-Haim | |
| 5,716,321 A * | 2/1998 | Kerin et al. | 600/114 |
| 5,722,403 A | 3/1998 | McGee et al. | |
| 5,725,523 A * | 3/1998 | Mueller | 606/15 |
| 5,746,747 A | 5/1998 | McKeating | |
| 5,749,846 A | 5/1998 | Edwards et al. | |
| 5,754,313 A | 5/1998 | Pelchy et al. | |
| 5,766,137 A | 6/1998 | Omata | |
| 5,769,846 A | 6/1998 | Edwards et al. | |
| 5,792,045 A | 8/1998 | Adair | |
| 5,797,903 A | 8/1998 | Swanson et al. | |
| 5,827,268 A | 10/1998 | Laufer | |
| 5,829,447 A | 11/1998 | Stevens et al. | |
| 5,843,118 A | 12/1998 | Sepetka et al. | |
| 5,848,969 A | 12/1998 | Panescu et al. | |
| 5,860,974 A | 1/1999 | Abele | |
| 5,860,991 A | 1/1999 | Klein et al. | |
| 5,865,791 A | 2/1999 | Whayne et al. | |
| 5,879,366 A | 3/1999 | Shaw et al. | |
| 5,895,417 A | 4/1999 | Pomeranz et al. | |
| 5,897,487 A * | 4/1999 | Ouchi | 600/127 |
| 5,897,553 A | 4/1999 | Mulier et al. | |
| 5,902,328 A | 5/1999 | LaFontaine et al. | |
| 5,904,651 A | 5/1999 | Swanson et al. | |
| 5,908,445 A | 6/1999 | Whayne et al. | |
| 5,928,250 A | 7/1999 | Koike et al. | |
| 5,929,901 A | 7/1999 | Adair et al. | |
| 5,941,845 A | 8/1999 | Tu et al. | |
| 5,944,690 A | 8/1999 | Falwell et al. | |
| 5,964,755 A | 10/1999 | Edwards | |
| 5,968,053 A | 10/1999 | Revelas | |
| 5,986,693 A | 11/1999 | Adair et al. | |
| 5,997,571 A | 12/1999 | Farr et al. | |
| 6,004,269 A | 12/1999 | Crowley et al. | |
| 6,012,457 A | 1/2000 | Lesh | |
| 6,024,740 A | 2/2000 | Lesh et al. | |
| 6,027,501 A | 2/2000 | Goble et al. | |
| 6,036,685 A | 3/2000 | Mueller | |
| 6,043,839 A | 3/2000 | Adair et al. | |
| 6,047,218 A | 4/2000 | Whayne et al. | |
| 6,063,077 A | 5/2000 | Schaer | |
| 6,063,081 A | 5/2000 | Mulier et al. | |
| 6,068,653 A | 5/2000 | LaFontaine | |
| 6,071,302 A | 6/2000 | Sinofsky et al. | |
| 6,081,740 A | 6/2000 | Gombrich et al. | |
| 6,086,528 A | 7/2000 | Adair | |
| 6,099,498 A | 8/2000 | Addis | |
| 6,099,514 A | 8/2000 | Sharkey et al. | |
| 6,102,905 A | 8/2000 | Baxter et al. | |
| 6,115,626 A | 9/2000 | Whayne et al. | |
| 6,123,703 A | 9/2000 | Tu et al. | |
| 6,123,718 A | 9/2000 | Tu et al. | |
| 6,129,724 A | 10/2000 | Fleischman et al. | |
| 6,139,508 A | 10/2000 | Simpson et al. | |
| 6,142,993 A | 11/2000 | Whayne et al. | |
| 6,152,144 A | 11/2000 | Lesh et al. | |
| 6,156,350 A | 12/2000 | Constantz | |
| 6,159,203 A | 12/2000 | Sinofsky | |
| 6,161,543 A | 12/2000 | Cox et al. | |
| 6,164,283 A | 12/2000 | Lesh | |
| 6,167,297 A | 12/2000 | Benaron | |
| 6,168,591 B1 | 1/2001 | Sinofsky | |
| 6,168,594 B1 | 1/2001 | LaFontaine et al. | |
| 6,178,346 B1 | 1/2001 | Amundson et al. | |
| 6,190,381 B1 | 2/2001 | Olsen et al. | |
| 6,211,904 B1 | 4/2001 | Adair et al. | |
| 6,224,553 B1 | 5/2001 | Nevo | |
| 6,231,561 B1 | 5/2001 | Frazier et al. | |
| 6,235,044 B1 | 5/2001 | Root et al. | |
| 6,237,605 B1 | 5/2001 | Vaska et al. | |
| 6,238,393 B1 | 5/2001 | Mulier et al. | |
| 6,240,312 B1 | 5/2001 | Alfano et al. | |
| 6,254,598 B1 | 7/2001 | Edwards et al. | |
| 6,258,083 B1 | 7/2001 | Daniel et al. | |
| 6,270,492 B1 | 8/2001 | Sinofsky | |
| 6,275,255 B1 | 8/2001 | Adair et al. | |
| 6,290,689 B1 | 9/2001 | Delaney et al. | |
| 6,310,642 B1 | 10/2001 | Adair et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,315,777 B1 | 11/2001 | Comben | |
| 6,315,778 B1 | 11/2001 | Gambale et al. | |
| 6,322,536 B1 | 11/2001 | Rosengart et al. | |
| 6,325,797 B1 | 12/2001 | Stewart et al. | |
| 6,328,727 B1 | 12/2001 | Frazier et al. | |
| 6,358,247 B1 | 3/2002 | Altman et al. | |
| 6,358,248 B1 | 3/2002 | Mulier et al. | |
| 6,375,654 B1 | 4/2002 | McIntyre | |
| 6,379,345 B1 | 4/2002 | Constantz | |
| 6,385,476 B1 | 5/2002 | Osadchy et al. | |
| 6,387,043 B1 | 5/2002 | Yoon | |
| 6,387,071 B1 | 5/2002 | Constantz | |
| 6,394,096 B1 | 5/2002 | Constantz | |
| 6,396,873 B1 | 5/2002 | Goldstein et al. | |
| 6,398,780 B1 | 6/2002 | Farley et al. | |
| 6,401,719 B1 | 6/2002 | Farley et al. | |
| 6,409,722 B1 | 6/2002 | Hoey et al. | |
| 6,416,511 B1 | 7/2002 | Lesh et al. | |
| 6,419,669 B1 | 7/2002 | Frazier et al. | |
| 6,423,051 B1 | 7/2002 | Kaplan et al. | |
| 6,423,055 B1 | 7/2002 | Farr et al. | |
| 6,423,058 B1 | 7/2002 | Edwards et al. | |
| 6,428,536 B2 | 8/2002 | Panescu et al. | |
| 6,440,119 B1 | 8/2002 | Nakada et al. | |
| 6,464,697 B1 | 10/2002 | Edwards et al. | |

| | | | | | | |
|---|---|---|---|---|---|---|
| 6,474,340 B1 | 11/2002 | Vaska et al. | | 6,971,394 B2 | 12/2005 | Sliwa, Jr. et al. |
| 6,475,223 B1 | 11/2002 | Werp et al. | | 6,974,464 B2 | 12/2005 | Quijano et al. |
| 6,478,769 B1 | 11/2002 | Parker | | 6,979,290 B2 * | 12/2005 | Mourlas et al. ............... 600/115 |
| 6,482,162 B1 | 11/2002 | Moore | | 6,982,740 B2 | 1/2006 | Adair et al. |
| 6,484,727 B1 | 11/2002 | Vaska et al. | | 6,984,232 B2 | 1/2006 | Vanney et al. |
| 6,485,489 B2 | 11/2002 | Teirstein et al. | | 6,994,094 B2 | 2/2006 | Schwartz |
| 6,488,671 B1 | 12/2002 | Constantz et al. | | 7,019,610 B2 | 3/2006 | Creighton, IV et al. |
| 6,494,902 B2 | 12/2002 | Hoey et al. | | 7,030,904 B2 | 4/2006 | Adair et al. |
| 6,497,705 B2 | 12/2002 | Comben | | 7,041,098 B2 | 5/2006 | Farley et al. |
| 6,500,174 B1 | 12/2002 | Maguire et al. | | 7,042,487 B2 | 5/2006 | Nakashima |
| 6,502,576 B1 | 1/2003 | Lesh | | 7,044,135 B2 | 5/2006 | Lesh |
| 6,514,249 B1 | 2/2003 | Maguire et al. | | 7,052,493 B2 | 5/2006 | Vaska et al. |
| 6,517,533 B1 | 2/2003 | Swaminathan | | 7,090,683 B2 | 8/2006 | Brock et al. |
| 6,527,979 B2 | 3/2003 | Constantz et al. | | 7,118,566 B2 | 10/2006 | Jahns |
| 6,533,767 B2 | 3/2003 | Johansson et al. | | 7,156,845 B2 | 1/2007 | Mulier et al. |
| 6,537,272 B2 | 3/2003 | Christopherson et al. | | 7,163,534 B2 | 1/2007 | Brucker et al. |
| 6,540,733 B2 | 4/2003 | Constantz et al. | | 7,166,537 B2 | 1/2007 | Jacobsen et al. |
| 6,540,744 B2 | 4/2003 | Hassett et al. | | 7,169,144 B2 | 1/2007 | Hoey et al. |
| 6,544,195 B2 | 4/2003 | Wilson et al. | | 7,207,984 B2 | 4/2007 | Farr et al. |
| 6,547,780 B1 | 4/2003 | Sinofsky | | 7,217,268 B2 | 5/2007 | Eggers et al. |
| 6,558,375 B1 | 5/2003 | Sinofsky et al. | | 7,242,832 B2 | 7/2007 | Carlin et al. |
| 6,562,020 B1 | 5/2003 | Constantz et al. | | 7,247,155 B2 | 7/2007 | Hoey et al. |
| 6,572,609 B1 | 6/2003 | Farr et al. | | 7,261,711 B2 | 8/2007 | Mulier et al. |
| 6,579,285 B2 | 6/2003 | Sinofsky | | 7,263,397 B2 | 8/2007 | Hauck et al. |
| 6,585,732 B2 | 7/2003 | Mulier et al. | | 7,276,061 B2 | 10/2007 | Schaer et al. |
| 6,587,709 B2 | 7/2003 | Solf et al. | | 7,527,625 B2 | 5/2009 | Knight et al. |
| 6,593,884 B1 | 7/2003 | Gilboa et al. | | 7,534,204 B2 | 5/2009 | Starksen et al. |
| 6,605,055 B1 * | 8/2003 | Sinofsky et al. ........... 604/96.01 | | 7,569,052 B2 | 8/2009 | Phan et al. |
| 6,622,732 B2 | 9/2003 | Constantz | | 7,758,499 B2 | 7/2010 | Adler |
| 6,626,900 B1 | 9/2003 | Sinofsky et al. | | 7,860,555 B2 * | 12/2010 | Saadat .......................... 600/476 |
| 6,635,070 B2 | 10/2003 | Leeflang et al. | | 7,860,556 B2 * | 12/2010 | Saadat .......................... 600/476 |
| 6,645,202 B1 | 11/2003 | Pless et al. | | 2001/0005789 A1 | 6/2001 | Root et al. |
| 6,650,923 B1 | 11/2003 | Lesh et al. | | 2001/0020126 A1 | 9/2001 | Swanson et al. |
| 6,658,279 B2 | 12/2003 | Swanson et al. | | 2001/0031912 A1 | 10/2001 | Adler |
| 6,659,940 B2 | 12/2003 | Adler | | 2001/0047136 A1 | 11/2001 | Domanik et al. |
| 6,673,090 B2 | 1/2004 | Root et al. | | 2001/0052930 A1 | 12/2001 | Adair et al. |
| 6,676,656 B2 | 1/2004 | Sinofsky | | 2002/0065455 A1 | 5/2002 | Ben-Haim et al. |
| 6,679,836 B2 | 1/2004 | Couvillon, Jr. | | 2002/0068853 A1 | 6/2002 | Adler et al. |
| 6,682,526 B1 | 1/2004 | Parker et al. | | 2002/0080248 A1 | 6/2002 | Adair et al. |
| 6,689,128 B2 | 2/2004 | Sliwa, Jr. et al. | | 2002/0087166 A1 | 7/2002 | Brock et al. |
| 6,692,430 B2 | 2/2004 | Adler | | 2002/0087169 A1 | 7/2002 | Brock et al. |
| 6,701,581 B2 | 3/2004 | Senovich et al. | | 2002/0091304 A1 | 7/2002 | Ogura et al. |
| 6,701,931 B2 | 3/2004 | Sliwa, Jr. et al. | | 2003/0069593 A1 | 4/2003 | Tremulis et al. |
| 6,702,780 B1 | 3/2004 | Gilboa et al. | | 2003/0120142 A1 | 6/2003 | Dubuc et al. |
| 6,704,043 B2 | 3/2004 | Goldstein et al. | | 2003/0144657 A1 | 7/2003 | Bowe et al. |
| 6,706,039 B2 | 3/2004 | Mulier et al. | | 2003/0171741 A1 | 9/2003 | Ziebol et al. |
| 6,712,798 B2 | 3/2004 | Constantz | | 2003/0181939 A1 | 9/2003 | Bonutti |
| 6,719,747 B2 | 4/2004 | Constantz et al. | | 2003/0216720 A1 | 11/2003 | Sinofsky |
| 6,719,755 B2 | 4/2004 | Sliwa, Jr. et al. | | 2003/0220574 A1 | 11/2003 | Markus et al. |
| 6,730,063 B2 | 5/2004 | Delaney et al. | | 2003/0222325 A1 | 12/2003 | Jacobsen et al. |
| 6,736,810 B2 | 5/2004 | Hoey et al. | | 2004/0006333 A1 | 1/2004 | Arnold et al. |
| 6,755,790 B2 | 6/2004 | Stewart et al. | | 2004/0049211 A1 | 3/2004 | Tremulis et al. |
| 6,755,811 B1 | 6/2004 | Constantz | | 2004/0054335 A1 | 3/2004 | Lesh et al. |
| 6,764,487 B2 | 7/2004 | Mulier et al. | | 2004/0054389 A1 | 3/2004 | Osypka |
| 6,771,996 B2 | 8/2004 | Bowe et al. | | 2004/0082833 A1 | 4/2004 | Adler et al. |
| 6,805,128 B1 | 10/2004 | Pless et al. | | 2004/0097788 A1 | 5/2004 | Mourlas et al. |
| 6,805,129 B1 | 10/2004 | Pless et al. | | 2004/0117032 A1 | 6/2004 | Roth |
| 6,811,562 B1 | 11/2004 | Pless | | 2004/0133113 A1 | 7/2004 | Krishnan |
| 6,833,814 B2 | 12/2004 | Gilboa et al. | | 2004/0138707 A1 | 7/2004 | Greenhalgh |
| 6,840,923 B1 | 1/2005 | Lapcevic | | 2004/0147806 A1 | 7/2004 | Adler |
| 6,840,936 B2 | 1/2005 | Sliwa, Jr. et al. | | 2004/0147911 A1 | 7/2004 | Sinofsky |
| 6,849,073 B2 | 2/2005 | Hoey et al. | | 2004/0147912 A1 | 7/2004 | Sinofsky |
| 6,858,005 B2 | 2/2005 | Ohline et al. | | 2004/0147913 A1 | 7/2004 | Sinofsky |
| 6,858,026 B2 | 2/2005 | Sliwa, Jr. et al. | | 2004/0158289 A1 | 8/2004 | Girouard et al. |
| 6,866,651 B2 | 3/2005 | Constantz | | 2004/0167503 A1 | 8/2004 | Sinofsky |
| 6,887,237 B2 | 5/2005 | McGaffigan | | 2004/0181237 A1 | 9/2004 | Forde et al. |
| 6,892,091 B1 | 5/2005 | Ben-Haim et al. | | 2004/0199052 A1 | 10/2004 | Banik et al. |
| 6,896,690 B1 | 5/2005 | Lambrecht et al. | | 2004/0215183 A1 | 10/2004 | Hoey et al. |
| 6,899,672 B2 | 5/2005 | Chin et al. | | 2004/0220471 A1 | 11/2004 | Schwartz |
| 6,915,154 B1 | 7/2005 | Docherty et al. | | 2004/0248837 A1 | 12/2004 | Raz et al. |
| 6,923,805 B1 | 8/2005 | LaFontaine et al. | | 2004/0254523 A1 | 12/2004 | Fitzgerald et al. |
| 6,929,010 B2 | 8/2005 | Vaska et al. | | 2005/0014995 A1 | 1/2005 | Amundson et al. |
| 6,932,809 B2 | 8/2005 | Sinofsky | | 2005/0015048 A1 | 1/2005 | Chiu et al. |
| 6,939,348 B2 | 9/2005 | Malecki et al. | | 2005/0020914 A1 | 1/2005 | Amundson et al. |
| 6,942,657 B2 | 9/2005 | Sinofsky et al. | | 2005/0027163 A1 | 2/2005 | Chin et al. |
| 6,949,095 B2 | 9/2005 | Vaska et al. | | 2005/0038419 A9 | 2/2005 | Arnold et al. |
| 6,953,457 B2 | 10/2005 | Farr et al. | | 2005/0059862 A1 | 3/2005 | Phan |
| 6,955,173 B2 | 10/2005 | Lesh | | 2005/0059954 A1 | 3/2005 | Constantz |
| 6,962,589 B2 | 11/2005 | Mulier et al. | | 2005/0059965 A1 | 3/2005 | Eberl et al. |

| | | |
|---|---|---|
| 2005/0065504 A1 | 3/2005 | Melsky et al. |
| 2005/0090818 A1 | 4/2005 | Pike, Jr. et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0119523 A1 | 6/2005 | Starksen et al. |
| 2005/0124969 A1 | 6/2005 | Fitzgerald et al. |
| 2005/0154252 A1 | 7/2005 | Sharkey et al. |
| 2005/0158899 A1 | 7/2005 | Jacobsen et al. |
| 2005/0159702 A1* | 7/2005 | Sekiguchi et al. ......... 604/99.01 |
| 2005/0165279 A1 | 7/2005 | Adler et al. |
| 2005/0165391 A1 | 7/2005 | Maguire et al. |
| 2005/0182465 A1 | 8/2005 | Ness |
| 2005/0197530 A1* | 9/2005 | Wallace et al. ............... 600/116 |
| 2005/0197623 A1 | 9/2005 | Leeflang et al. |
| 2005/0215895 A1 | 9/2005 | Popp et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2005/0267452 A1 | 12/2005 | Farr et al. |
| 2006/0009715 A1 | 1/2006 | Khairkhahan et al. |
| 2006/0009737 A1 | 1/2006 | Whiting et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0030844 A1 | 2/2006 | Knight et al. |
| 2006/0069303 A1 | 3/2006 | Couvillon et al. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0184048 A1 | 8/2006 | Saadat |
| 2006/0217755 A1 | 9/2006 | Eversull et al. |
| 2006/0253113 A1 | 11/2006 | Arnold et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100241 A1 | 5/2007 | Adler |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0265609 A1 | 11/2007 | Thapliyal et al. |
| 2007/0265610 A1 | 11/2007 | Thapliyal et al. |
| 2007/0270686 A1 | 11/2007 | Ritter et al. |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015445 A1 | 1/2008 | Saadat et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033290 A1 | 2/2008 | Saadat et al. |
| 2008/0057106 A1 | 3/2008 | Erickson et al. |
| 2008/0058590 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0188759 A1 | 8/2008 | Saadat et al. |
| 2008/0228032 A1 | 9/2008 | Starksen et al. |
| 2008/0275300 A1 | 11/2008 | Rothe et al. |
| 2008/0281293 A1 | 11/2008 | Peh et al. |
| 2008/0287790 A1 | 11/2008 | Li |
| 2008/0287805 A1 | 11/2008 | Li |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076489 A1 | 3/2009 | Welches et al. |
| 2009/0076498 A1 | 3/2009 | Saadat et al. |
| 2009/0143640 A1 | 6/2009 | Saadat et al. |
| 2009/0264727 A1 | 10/2009 | Markowitz et al. |
| 2009/0267773 A1 | 10/2009 | Markowitz et al. |
| 2010/0004506 A1 | 1/2010 | Saadat |
| 2010/0004661 A1 | 1/2010 | Verin et al. |

FOREIGN PATENT DOCUMENTS

| | | |
|---|---|---|
| EP | 0283661 | 9/1988 |
| EP | 0301288 A1 | 2/1999 |
| JP | 59093413 A | 5/1984 |
| WO | WO 94/07413 | 4/1994 |
| WO | WO 95/03843 | 2/1995 |
| WO | WO 98/18388 | 5/1998 |
| WO | WO 03/039350 | 5/2003 |
| WO | WO 03/053491 | 7/2003 |
| WO | WO 03/101287 | 12/2003 |
| WO | WO 2004/043272 | 5/2004 |
| WO | WO 2004/080508 | 9/2004 |
| WO | WO 2005/070330 | 8/2005 |
| WO | WO 2005/077435 | 8/2005 |
| WO | WO 2005/081202 | 9/2005 |
| WO | WO 2006/017517 | 2/2006 |
| WO | WO 2006/024015 | 3/2006 |
| WO | WO 2006/083794 | 8/2006 |
| WO | WO 2006/091597 | 8/2006 |
| WO | WO 2006/126979 | 11/2006 |
| WO | WO 2007/067323 | 6/2007 |
| WO | WO 2007/079268 | 7/2007 |
| WO | WO 2007/133845 | 11/2007 |
| WO | WO 2007/134258 | 11/2007 |
| WO | WO 2008/015625 | 2/2008 |
| WO | WO 2008/021994 | 2/2008 |
| WO | WO 2008/021997 | 2/2008 |
| WO | WO 2008/021998 | 2/2008 |
| WO | WO 2008/024261 | 2/2008 |
| WO | WO 2008/079828 | 7/2008 |
| WO | WO 2009/112262 | 9/2009 |

OTHER PUBLICATIONS

Avitall, Right-Sided Driven Atrial Fibrillation in a Sterile Pericarditis Dog Model, PACE, vol. 17, p. 774, 1994.

Avitall, Vagally Mediated Atrial Fibrillation in a Dog Model can be Ablated by Placing Linear Radiofrequency Lesions at the Junction of the Right Atrial Appendage and the Superior Vena Cava, PACE, vol. 18, p. 857, 1995.

Baker, Nonpharmacologic Approaches to the Treatment of Atrial Fibrillation and Atrial Flutter, J. Cardiovasc. Electrophysiol., vol. 6, pp. 972-978, 1995.

Bhakta, Principles of Electroanatomic Mapping, Indian Pacing & Electrophysiol J., vol. 8, No. 1, pp. 32-50, 2008.

Bidoggia, Transseptal Left Heart Catheterization: Usefulness of the Intracavitary Electrocardiogram in the Localization of the Fossa Ovalis, Cathet Cardiovasc Diagn., vol. 24, No. 3, pp. 221-225, 1991.

Bredikis, Surgery of Tachyarrhythmia: Intracardiac Closed Heart Cryoablation, PACE, vol. 13, pp. 1980-1984, 1990.

Cox, Cardiac Surgery for Arrhythmias, J. Cardiovasc. Electrophysiol., vol. 15, pp. 250-262, 2004.

Cox, Five-Year Experience With the Maze Procedure for Atrial Fibrillation, Ann. Thorac. Surg., vol. 56, pp. 814-824, 1993.

Cox, Modification of the Maze Procedure for Atrial Flutter and Atrial Fibrillation, J. Thorac. Cardiovasc. Surg., vol. 110, pp. 473-484, 1995.

Cox, The Status of Surgery for Cardiac Arrhythmias, Circulation, vol. 71, pp. 413-417, 1985.

Cox, The Surgical Treatment of Atrial Fibrillation, J. Thorac Cardiovasc. Surg., vol. 101, pp. 584-592, 1991.

Elvan, Replication of the "Maze" Procedure by Radiofrequency Catheter Ablation Reduces the Ability to Induce Atrial Fibrillation, PACE, vol. 17, p. 774, 1994.

Elvan, Radiofrequency Catheter Ablation (RFCA) of the Atria Effectively Abolishes Pacing Induced Chronic Atrial Fibrillation, PACE, vol. 18, p. 856, 1995.

Elvan, Radiofrequency Catheter Ablation of the Atria Reduces Inducibility and Duration of Atrial Fibrillation in Dogs, Circulation, vol. 91, pp. 2235-2244, 1995.

European Patent Application No. 06734083.6 filed Jan. 30, 2006 in the name of Saadat et al., extended European Search Report mailed Jul. 1, 2009.

European Patent Application No. 06734083.6 filed Jan. 30, 2006 in the name of Saadat et al., office action mailed Oct. 23, 2009.

Fieguth, Inhibition of Atrial Fibrillation by Pulmonary Vein Isolation and Auricular Resection—Experimental Study in a Sheep Model, European J. Cardiothorac. Surg., vol. 11, pp. 714-721, 1997.

Hoey, Intramural Ablation Using Radiofrequency Energy Via Screw-Tip Catheter and Saline Electrode, PACE, vol. 18, p. 487, 1995.

Huang, Increase in the Lesion Size and Decrease in the Impedance Rise with a Saline Infusion Electrode Catheter for Radiofrequency, Circulation, vol. 80, No. 4, pp. II-324, 1989.

Moser, Angioscopic Visualization of Pulmonary Emboli, CHEST, vol. 77, No. 2, pp. 198-201, 1980.

Nakamura, Percutaneous Intracardiac Surgery With Cardioscopic Guidance, SPIE, vol. 1652, pp. 214-216, 1992.

Pappone, Circumferential Radiofrequency Ablation of Pulmonary Vein Ostia, Circulation, vol. 102, pp. 2619-2628, 2000.

Sethi, Transseptal Catheterization for the Electrophysiologist: Modification with a "View", J. Interv. Card. Electrophysiol., vol. 5, pp. 97-99, 2001, Kluwer Academic Publishers, Netherlands.

Thiagalingam, Cooled Needle Catheter Ablation Creates Deeper and Wider Lesions than Irrigated Tip Catheter Ablation, J. Cardiovasc. Electrophysiol., vol. 16, pp. 1-8, 2005.

U.S. Appl. No. 11/828,267, filed Jul. 25, 2007 in the name of Saadat et al., Non-final Office Action mailed Jan. 14, 2010.

U.S. Appl. No. 12/117,655, filed May 8, 2008 in the name of Saadat et al., Non-final Office Action mailed Jun. 8, 2009.

Willkampf, Radiofrequency Ablation with a Cooled Porous Electrode Catheter, JACC, vol. 11, No. 2, p. 17A, 1988.

Uchida, Developmental History of Cardioscopes, Coronary Angioscopy, pp. 187-197, 2001, Futura Publishing Co., Armonk, NY.

U.S. Appl. No. 12/117,655, filed May 8, 2008 in the name of Peh et al., non-final Office Action mailed Dec. 16, 2010.

U.S. Appl. No. 12/026,455, filed Feb. 5, 2008 in the name of Saadat et al., non-final Office Action mailed Dec. 27, 2010.

U.S. Appl. No. 11/259,498, filed Oct. 25, 2005 in the name of Saadat, Notice of Allowance mailed Nov. 15, 2010.

U.S. Appl. No. 11/560,742, filed Nov. 16, 2006 in the name of Saadat, Notice of Allowance mailed Nov. 15, 2010.

U.S. Appl. No. 12/464,800, filed May 12, 2009 in the name of Peh et al., non-final Office Action mailed Nov. 24, 2010.

U.S. Appl. No. 11/848,429, filed Aug. 31, 2007 in the name of Peh et al., non-final Office Action mailed Nov. 24, 2010.

U.S. Appl. No. 11/259,498, filed Oct. 25, 2005 in the name of Saadat, Notice of Allowance mailed Nov. 15, 2010.

U.S. Appl. No. 11/560,742, filed Nov. 16, 2006 in the name of Saadat, Notice of Allowance mailed Nov. 15, 2010.

U.S. Appl. No. 12/464,800, filed May 12, 2009 in the name of Peh et al., non-final Office Action mailed Nov. 24, 2010.

U.S. Appl. No. 11/848,429, filed Aug. 31, 2007 in the name of Peh et al., non-final Office Action mailed Nov. 24, 2010.

European Patent Application No. 07812146.4 filed Jun. 14, 2007 in the name of Voyage Medical, Inc., European Search Report mailed Nov. 18, 2010.

U.S. Appl. No. 11/560,732, filed Nov. 16, 2006 in the name of Saadat, Notice of Allowance mailed Feb. 3, 2011.

European Patent Application No. 07799466.3 filed Jul. 10, 2007 in the name of Voyage Medical, Inc., European Search Report mailed Nov. 18, 2010.

U.S. Appl. No. 11/775,771, filed Jul. 10, 2007 in the name of Saadat et al., Non-final Office Action mailed Aug. 27, 2010.

U.S. Appl. No. 11/828,267, filed Jul. 25, 2007 in the name of Saadat et al., final Office Action mailed Sep. 16, 2010.

European Patent Application No. 06734083.6 filed Jan. 30, 2006 in the name of Saadat et al, Examination Communication mailed May 18, 2010.

European Patent Application No. 07841754.0 filed Aug. 31, 2007 in the name of Saadat et al., Supplemental European Search Report mailed Jun. 30, 2010.

European Patent Application No. 08746822.9 filed Apr. 24, 2008 in the name of Rothe et al., European Search Report mailed Mar. 29, 2010.

European Patent Application No. 08746822.9 filed Apr. 24, 2008 in the name of Rothe et al., Office Action mailed Jul. 13, 2010.

U.S. Appl. No. 11/259,498, filed Oct. 25, 2005 in the name of Saadat et al., Non-final Office Action mailed Feb. 25, 2010.

U.S. Appl. No. 11/560,742, filed Nov. 16, 2006 in the name of Saadat, Non-final Office Action mailed Jun. 10, 2010.

U.S. Appl. No. 12/117,655, filed May 8, 2008 in the name of Peh et al., Final Office Action mailed Mar. 1, 2010.

U.S. Appl. No. 61/286,283, filed Dec. 14, 2009 in the name of Rothe et al.

U.S. Appl. No. 61/297,462, filed Jan. 22, 2010 in the name of Rothe et al.

\* cited by examiner

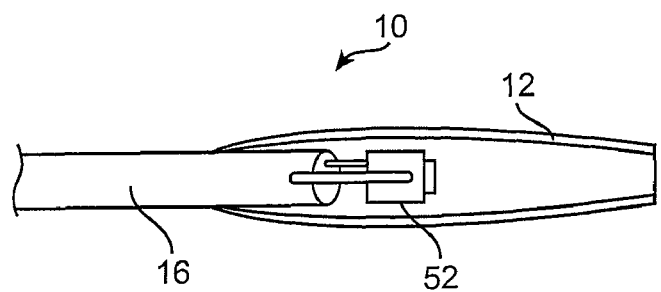
FIG. 4D
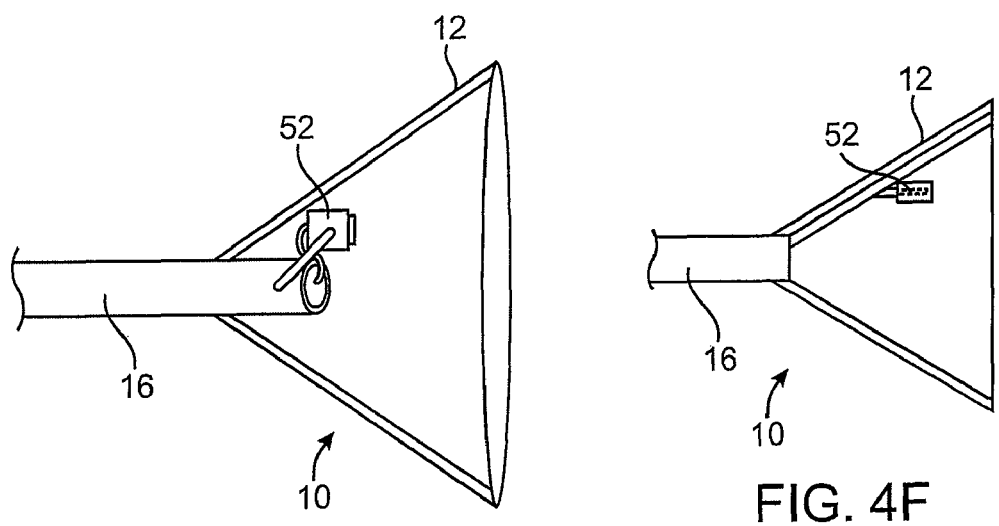
FIG. 4E
FIG. 4F
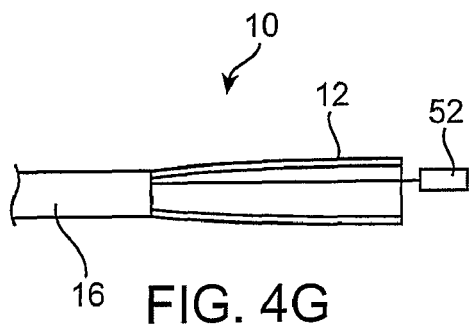
FIG. 4G

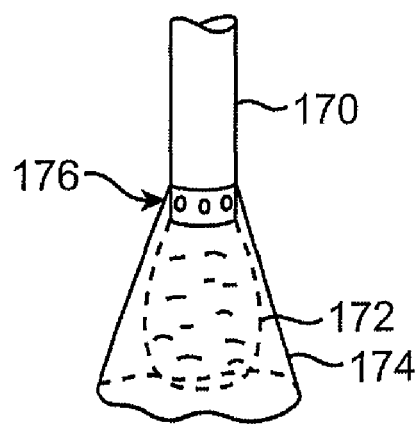
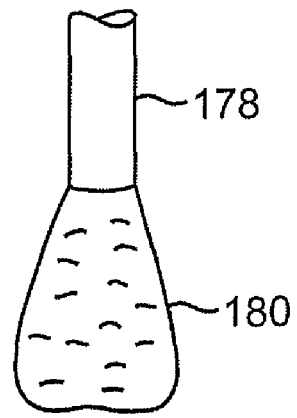
FIG. 11A  FIG. 11B
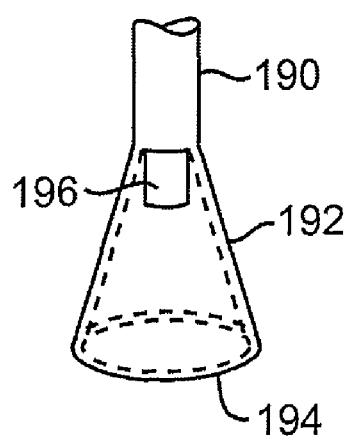
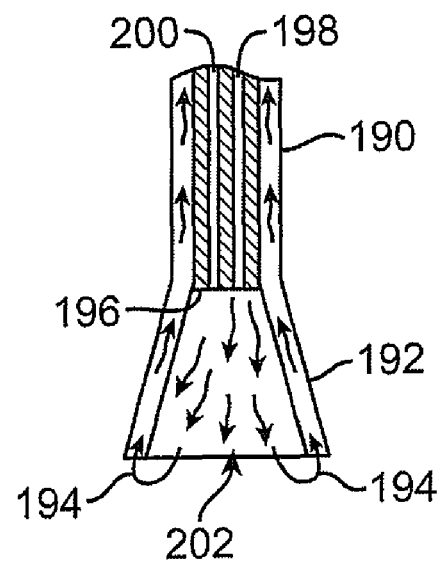
FIG. 13A  FIG. 13B

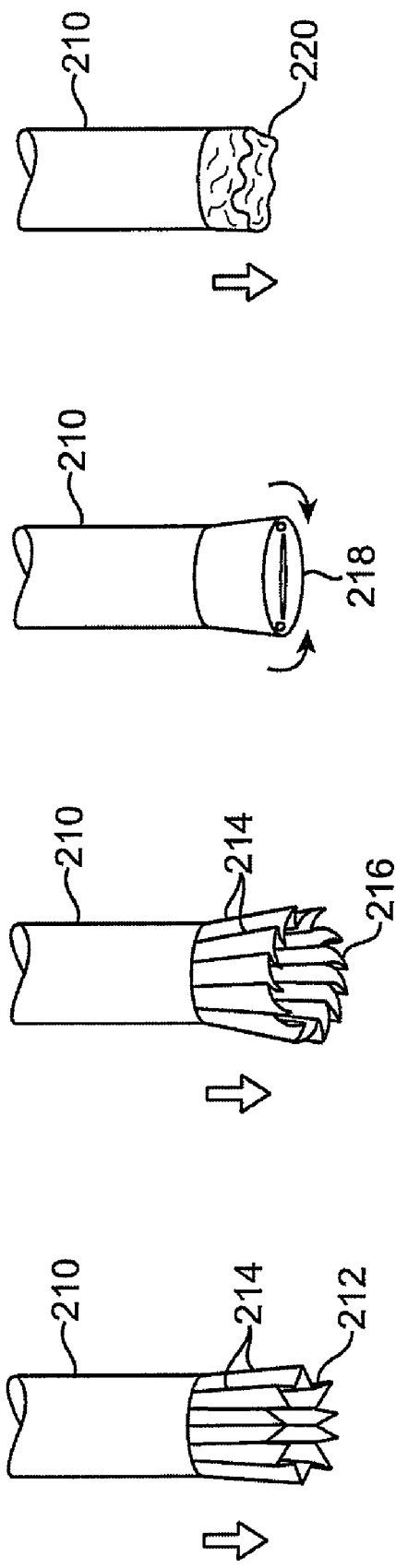

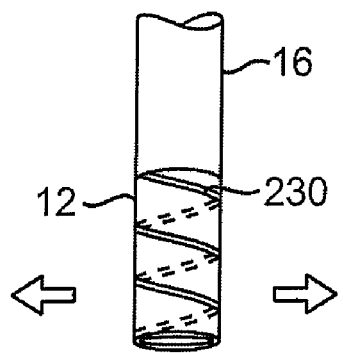 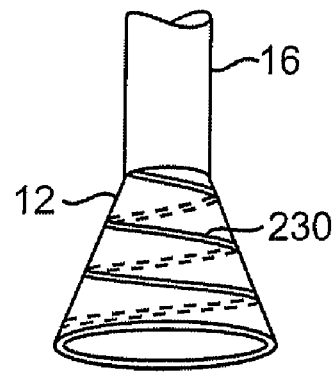
FIG. 15A     FIG. 15B
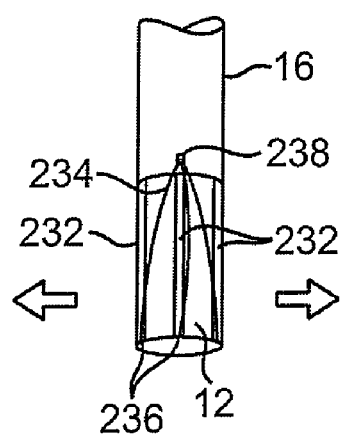 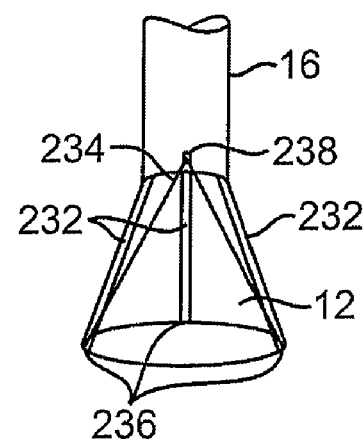
FIG. 16A     FIG. 16B

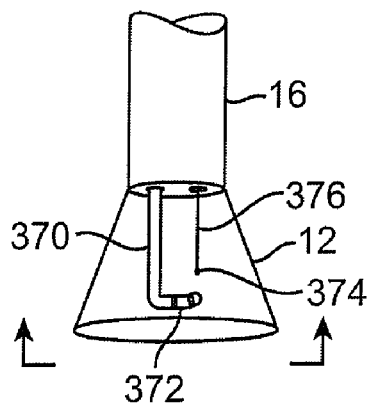
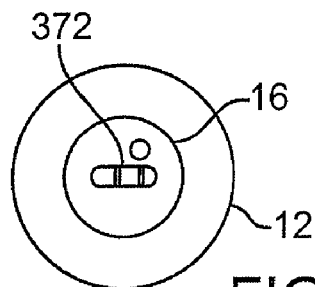
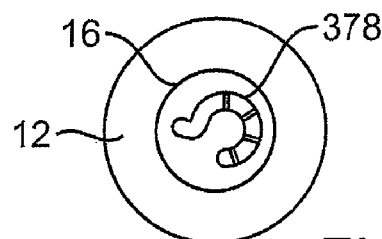
FIG. 31A
FIG. 31B
FIG. 31C
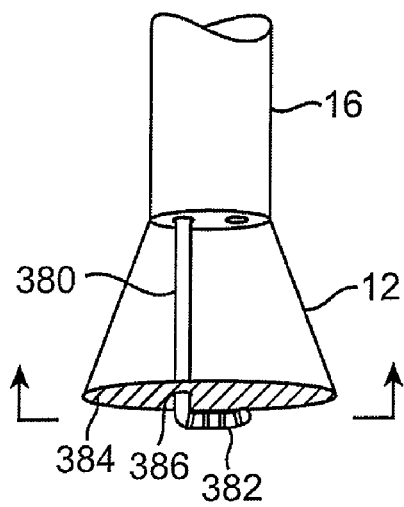
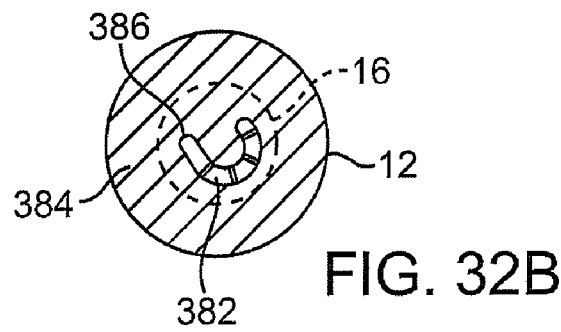
FIG. 32A
FIG. 32B

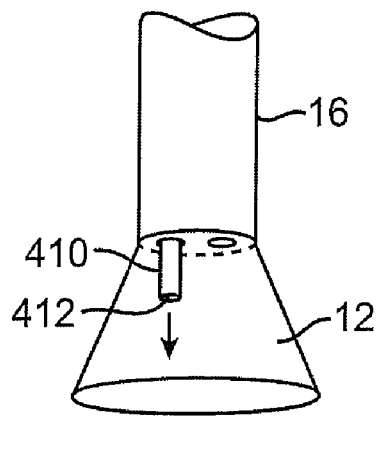
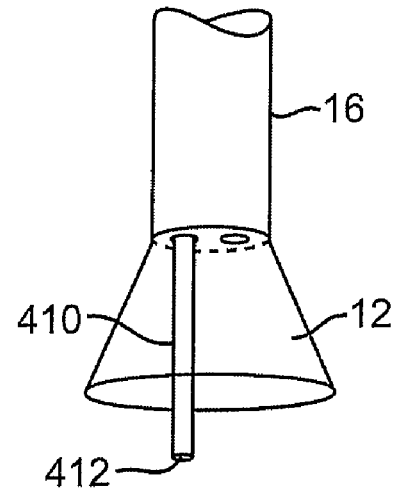
FIG. 35A  FIG. 35B
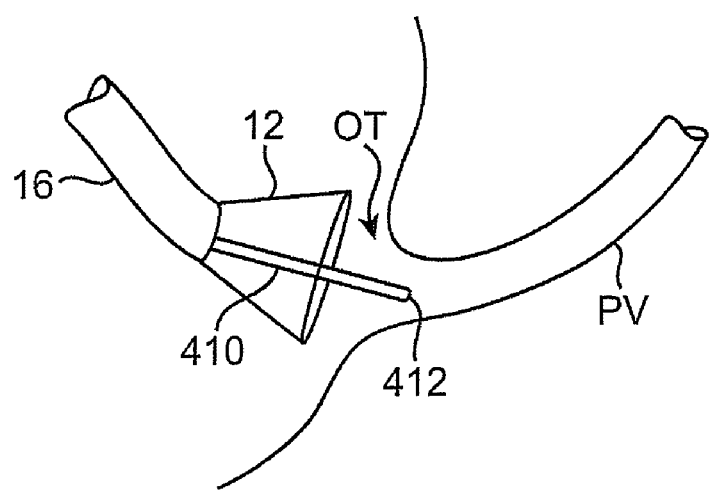
FIG. 35C

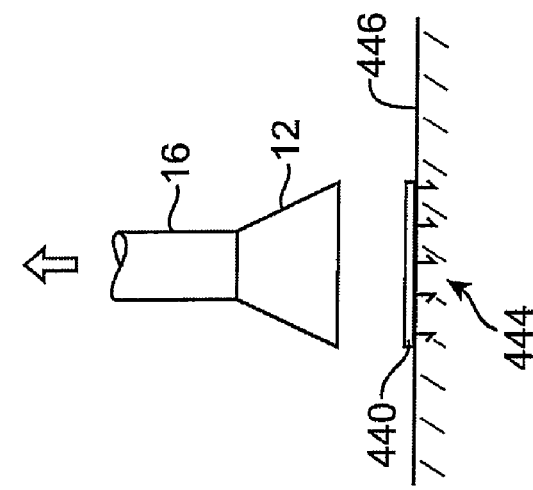
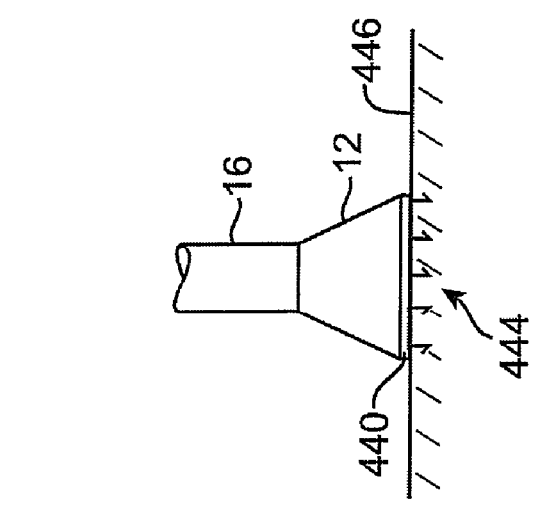
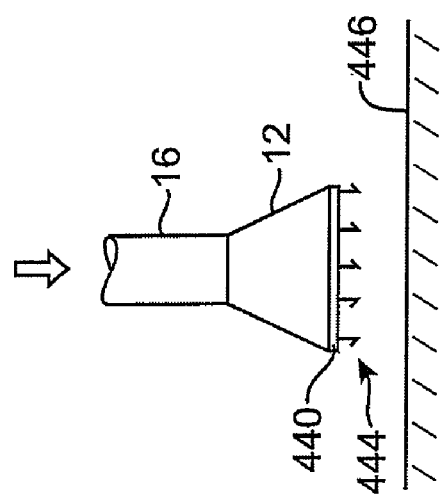

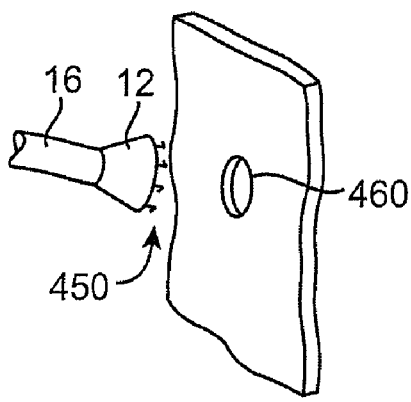 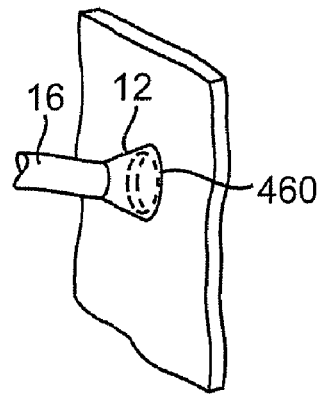
FIG. 41A                FIG. 41B
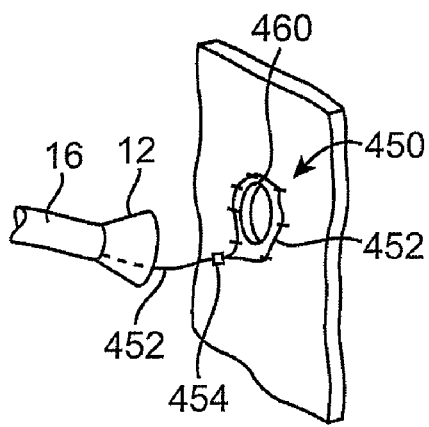 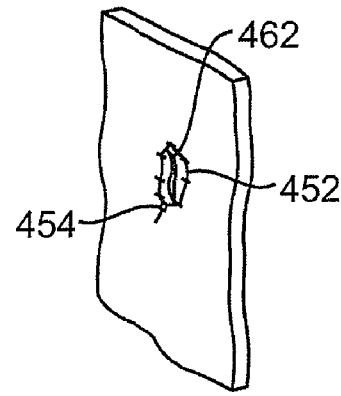
FIG. 41C                FIG. 41D

TISSUE VISUALIZATION AND MANIPULATION SYSTEMS

CROSS-REFERENCE TO RELATED APPLICATIONS

This application claims the benefit of priority to U.S. Provisional Patent Application Ser. No. 60/783,494 filed Mar. 17, 2006 and is a continuation-in-part of U.S. patent application Ser. No. 11/259,498 filed Oct. 25, 2005 which claims the benefit of priority to U.S. Provisional Patent Application Ser. No. 60/649,246 filed Feb. 2, 2005, each of which is incorporated herein by reference in its entirety.

FIELD OF THE INVENTION

The present invention relates generally to medical devices used for visualizing and/or manipulating regions of tissue within a body. More particularly, the present invention relates to apparatus and methods for visualizing and/or manipulating tissue regions within a body lumen, e.g., tissue surrounding or adjacent to valves within a heart, which are generally difficult to image because of surrounding opaque bodily fluids such as blood or the tissue of the inter-atrial septum for trans-septal procedures. However, it is understood that the systems described herein may be used in various parts of the anatomy.

BACKGROUND OF THE INVENTION

Conventional devices for visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood. Imaging may also use a fluorescence or gamma adapted visualization elements. Such elements may be able to distinguish between healthy and diseased tissue (e.g., infracted heart tissue).

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Thus, a tissue imaging system which is able to provide real-time in vivo images of tissue regions within body lumens such as the heart through opaque media such as blood and which also provide instruments for therapeutic procedures upon the visualized tissue are desirable.

BRIEF SUMMARY OF THE INVENTION

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. In addition, the deployment catheter may have additional lumens for various functions. For example, additional lumens may allow aspiration of air bubbles or other substances that may interfere with visualization of the target tissue When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

The imaging hood may be formed into any number of configurations and the imaging assembly may also be utilized with any number of therapeutic tools which may be deployed through the deployment catheter.

Variations of the inventive assemblies and their features described herein may be used with other devices that provide bounded regions. For example, U.S. Pat. No. 6,755,811 and US Published Patent Application No. 2005/0059954, both to Constantz, describe methods and devices for reducing mineral content of a region of non-intimal vascular tissue. The entirety of each of which is incorporated by reference herein.

BRIEF DESCRIPTION OF THE DRAWINGS

FIGS. 4D-4G illustrates cross-sectional views of a variation of a tissue imaging and manipulation assembly with off-axis visualization capabilities.

FIG. 11A shows a side view of another variation of a tissue imager having an imaging balloon within an expandable hood.

FIG. 11B shows another variation of a tissue imager utilizing a translucent or transparent imaging balloon.

FIGS. 13A and 13B show exemplary side and cross-sectional views, respectively, of another variation in which the injected fluid may be drawn back into the device for minimizing fluid input into a body being treated.

FIGS. 14A to 14D show various configurations and methods for configuring an imaging hood into a low-profile for delivery and/or deployment.

FIGS. 15A and 15B show an imaging hood having an helically expanding frame or support.

FIGS. 16A and 16B show another imaging hood having one or more hood support members, which are pivotably attached at their proximal ends to deployment catheter, integrated with a hood membrane.

FIGS. 31A to 31C show side and end views, respectively, of an imaging system which may be utilized with an ablation probe.

FIGS. 32A and 32B show side and end views, respectively, of another variation of the imaging hood with an ablation probe, where the imaging hood may be enclosed for regulating a temperature of the underlying tissue.

FIGS. 35A to 35C show an example of an extendible cannula generally comprising an elongate tubular member which may be positioned within the deployment catheter during delivery and then projected distally through the imaging hood and optionally beyond.

FIGS. 39A to 39C show one method for implanting the removable disk of FIGS. 38A and 38B.

FIGS. 41A to 41D show one method for deploying the anchor assembly of FIGS. 40A and 40B for closing an opening or wound.

DETAILED DESCRIPTION OF THE INVENTION

A tissue-imaging and manipulation apparatus described below is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating trans-septal access to the left atrium, cannulating the coronary sinus, diagnosis of valve regurgitation/stenosis, valvuloplasty, atrial appendage closure, arrhythmogenic focus ablation, among other procedures.

Figure 1A:
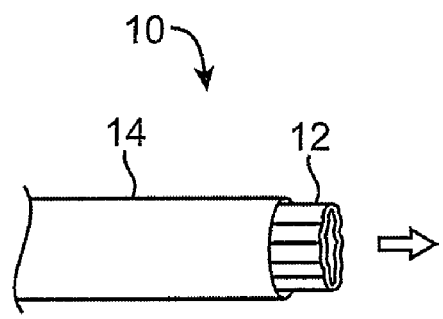
FIG. 1A shows a side view of one variation of a tissue imaging apparatus during deployment from a sheath or delivery catheter.
Figure 1B:
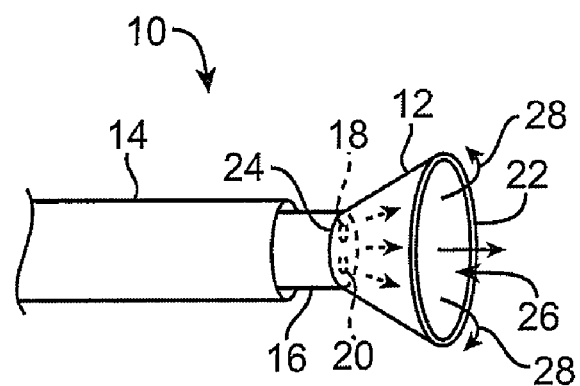
FIG. 1B shows the deployed tissue imaging apparatus of FIG. 1A having an optionally expandable hood or sheath attached to an imaging and/or diagnostic catheter.
Figure 1C:
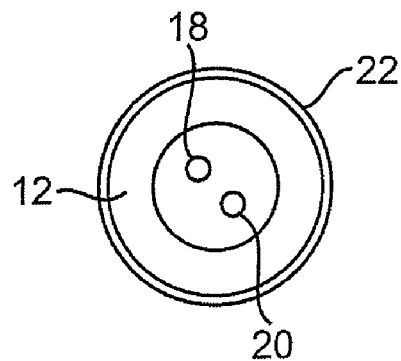
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, such as the mitral valve located at the outflow tract of the left atrium of the heart, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a trans-septal procedure or septostomy. For procedures such as percutaneous valve repair and replacement, trans-septal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 1D:
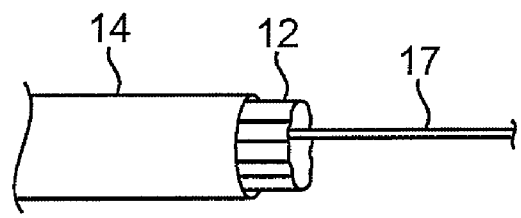
FIGS. 1D to 1F show the apparatus of FIGS. 1A to 1C with an additional lumen, e.g., for passage of a guidewire therethrough.
Figure 1E:
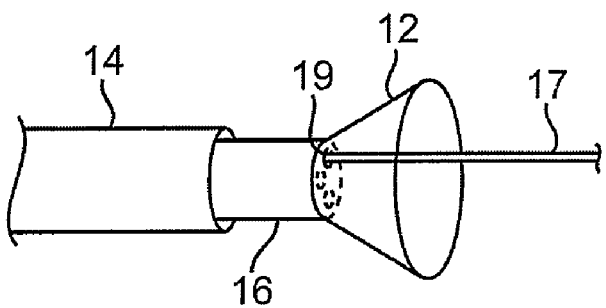
Figure 1F:
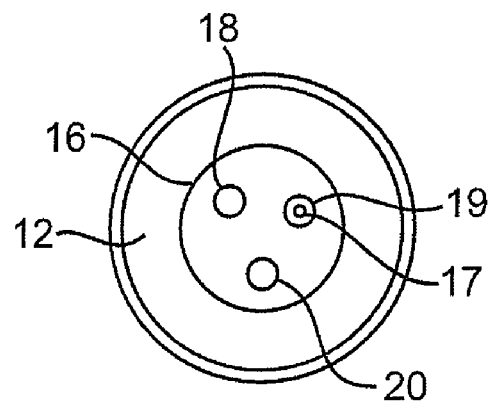

The imaging and manipulation assembly 10 may additionally define a guidewire lumen therethrough, e.g., a concentric or eccentric lumen, as shown in the side and end views, respectively, of FIGS. 1D to 1F. The deployment catheter 16 may define guidewire lumen 19 for facilitating the passage of the system over or along a guidewire 17, which may be advanced intravascularly within a body lumen. The deployment catheter 16 may then be advanced over the guidewire 17, as generally known in the art.

In operation, after imaging hood 12 has been deployed, as in FIG. 1B, and desirably positioned against the tissue region to be imaged along contact edge 22, the displacing fluid may be pumped at positive pressure through fluid delivery lumen 18 until the fluid fills open area 26 completely and displaces any fluid 28 from within open area 26. The displacing fluid flow may be laminarized to improve its clearing effect and to help prevent blood from re-entering the imaging hood 12. Alternatively, fluid flow may be started before the deployment takes place. The displacing fluid, also described herein as imaging fluid, may comprise any biocompatible fluid, e.g., saline, water, plasma, etc., which is sufficiently transparent to allow for relatively undistorted visualization through the fluid. Alternatively or additionally, any number of therapeutic drugs may be suspended within the fluid or may comprise the fluid itself which is pumped into open area 26 and which is subsequently passed into and through the heart and the patient body.

Figure 1G:
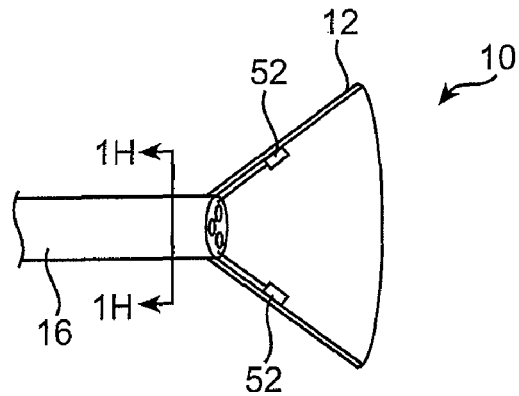
FIGS. 1G-1J illustrate additional variations of the assembly having visualization elements as well as illumination elements.

FIG. 1G illustrates another variation of a tissue imaging and manipulation assembly 10. In this variation, the assembly 10 comprises one or more visualization element 52 located in an "off-axis" position within the hood 12. The benefits of the "off-axis" configuration are discussed below. However, the assemblies of the present invention may comprise anywhere from a single visualization element 52 to several elements 52. For example, some variations of the assembly 10 may include at least two visualization elements 52 to enable 3-dimensional imaging of the open area within the hood 12. For example, the elements 52 may be sufficiently spaced around the perimeter of the hood 12 to allow generation of a 3-dimensional image. It is contemplated that optical fibers may be used in place of or in addition to the visualization elements shown in FIG. 1G. Additional means of obtaining a 3D image includes separating a single imaging element into two or more segments that can look at a target zone from two different angles. For example, such a stereoscopic visualization element may include a lenticular lens layer and light sensor array, the lenticular lens layer includes a plurality of lenticular elements, the sight sensor array includes a plurality of light sensors, where selected light sensors detect light at a predetermined range of wavelengths and where other light sensors detect light at another predetermined range of wavelengths, and where each of the lenticular elements is located in front of a selected group of the light sensors, to direct light from different directions to different light sensors within the selected group of the light sensors. Next, the views are processed producing a 3D image. Examples of such 3D imaging equipment is found in U.S. Pat. Nos. 6,396,873 and 6,704,043 both to Goldstein et al. and entitled "Optical Device". The entirety of both of which are incorporated by reference. Such products may be supplied by Visionsense, Inc. of Petah Tivak, Israel. An additional way to create a 3D image is by using two image guides made from optical fibers and spacing them apart by a small distance (0.1-10 mm) and combining these two images in one cohesive 3D image.

Figure 1H:
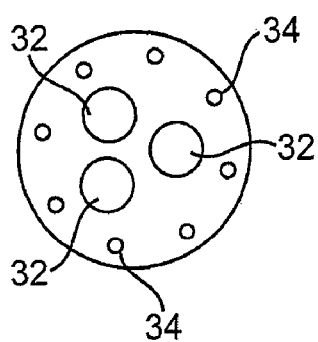

FIG. 1H illustrates a cross-sectional view taken along the line 1H-1H of FIG. 1G. As illustrated, a variation of the catheter 16 may include co-extruded channels 32 to carry wires or optical fibers running along the length or a portion of a length of the catheter 16. The channels 32 may permit connection of a visualization element to imaging equipment without taking up space from the remaining lumens 32. These channels can also contain electrical wires that carry the signal from an imaging detector to a sensor/processor outside the patient.

Figure 1I:
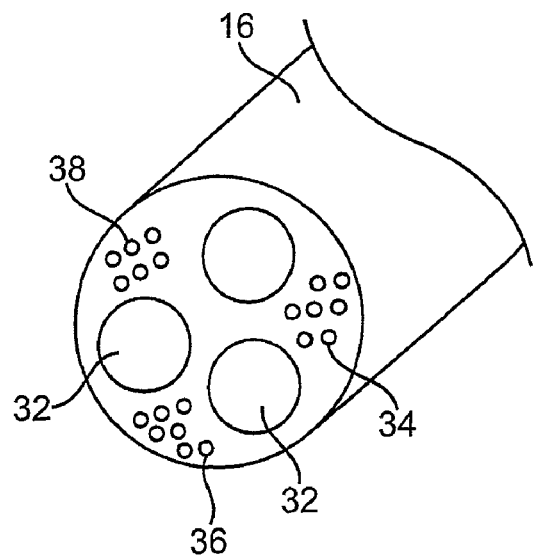

Alternatively, the channels 32 may provide a light source or supply. FIG. 1I illustrates anther variation of a distal end of a catheter according to the present invention. In this variation, the catheter will include a variety of lumens 32. As noted herein, the lumens 32 may be used for visualization, working channels, aspiration, delivery of tools, etc. The variation of FIG. 1I also illustrates the catheter 16 as having a number of illumination sources 36. The illumination sources may small illumination optical fibers or any other illumination source as commonly used. In another variation of the invention, the lumens 38 may provide irrigation or other fluids.

Figure 1J:
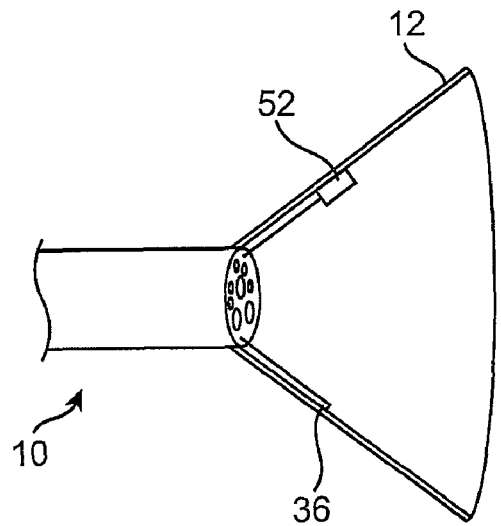

FIG. 1J illustrates another variation of a tissue imaging and manipulation assembly 10. In this variation, the hood 12 includes both a visualization component 52 and an illumination source 36 positioned on the interior surface of the hood 12. Again, as noted above, although the figure illustrates the hood 12 as containing a single visualization element 52 and a single illumination source 36 (such as a fiber, a LED, other light emitting source) variations of the device may include additional elements 52 or illumination sources.

Figure 2A:
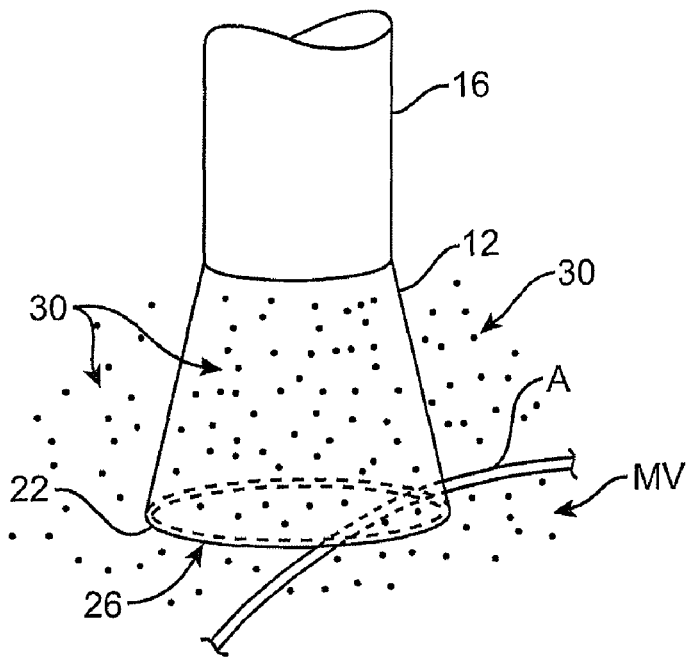
FIGS. 2A and 2B show one example of a deployed tissue imager positioned against or adjacent to the tissue to be imaged and a flow of fluid, such as saline, displacing blood from within the expandable hood.
Figure 2B:
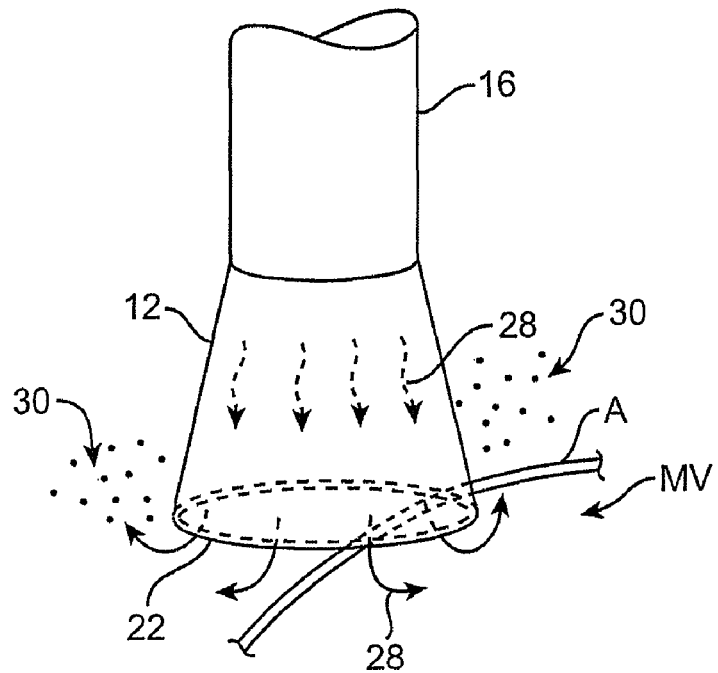

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
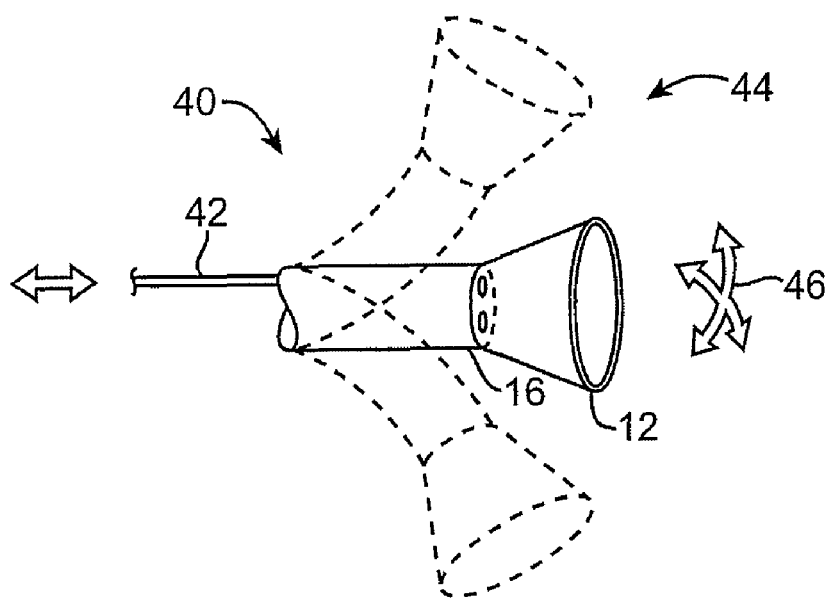
FIG. 3A shows an articulatable imaging assembly which may be manipulated via push-pull wires or by computer control.

In desirably positioning the assembly at various regions within the patient body, a number of articulation and manipulation controls may be utilized. For example, as shown in the articulatable imaging assembly 40 in FIG. 3A, one or more push-pull wires 42 may be routed through deployment catheter 16 for steering the distal end portion of the device in various directions 46 to desirably position the imaging hood 12 adjacent to a region of tissue to be visualized. Depending upon the positioning and the number of push-pull wires 42 utilized, deployment catheter 16 and imaging hood 12 may be articulated into any number of configurations 44. The push-pull wire or wires 42 may be articulated via their proximal ends from outside the patient body manually utilizing one or more controls. Alternatively, deployment catheter 16 may be articulated by computer control, as further described below.

Figure 3B:
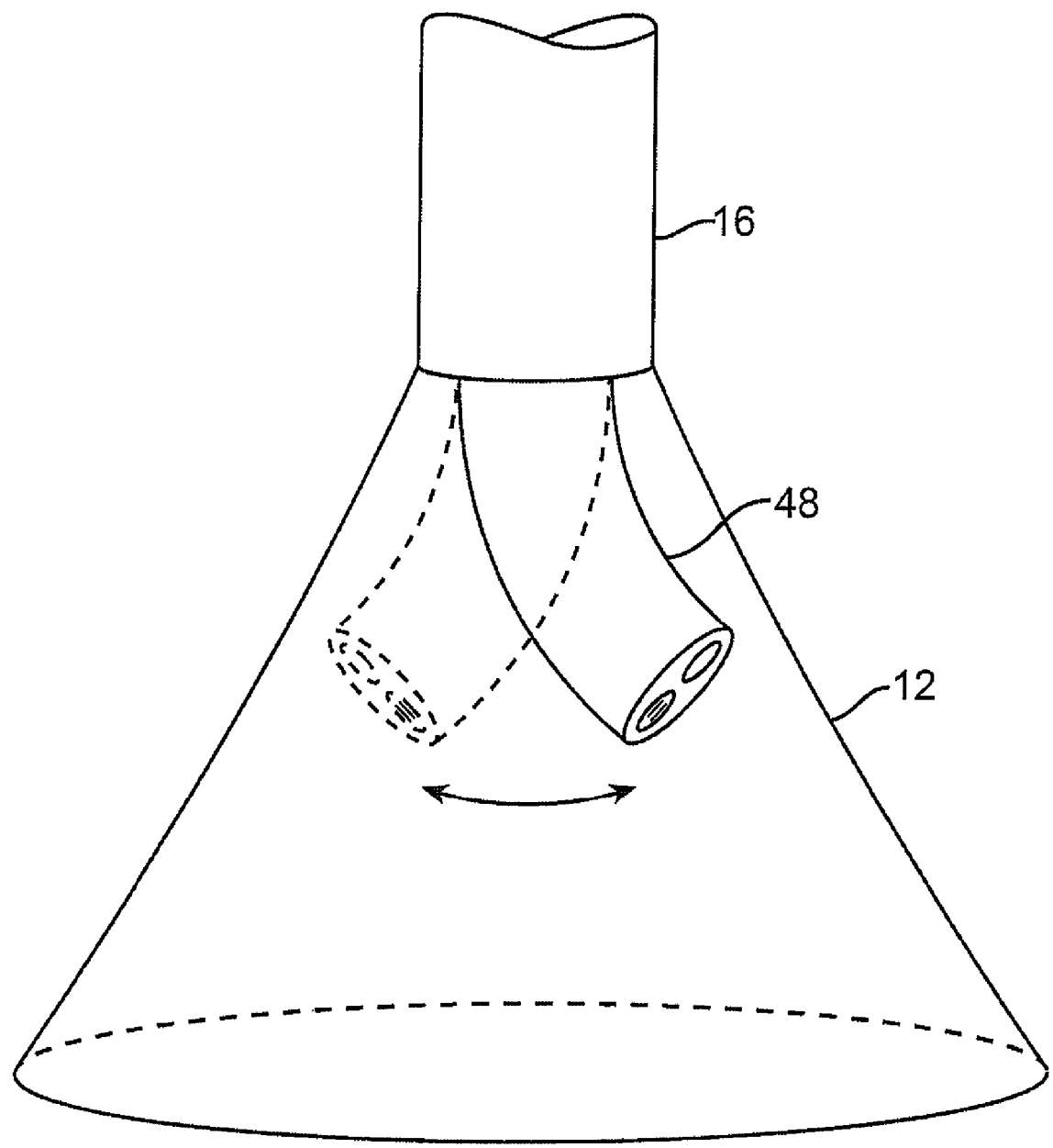
FIGS. 3B and 3C show steerable instruments, respectively, where an articulatable delivery catheter may be steered within the imaging hood or a distal portion of the deployment catheter itself may be steered.

Additionally or alternatively, an articulatable delivery catheter 48, which may be articulated via one or more push-pull wires and having an imaging lumen and one or more working lumens, may be delivered through the deployment catheter 16 and into imaging hood 12. With a distal portion of articulatable delivery catheter 48 within imaging hood 12, the clear displacing fluid may be pumped through delivery catheter 48 or deployment catheter 16 to clear the field within imaging hood 12. As shown in FIG. 3B, the articulatable delivery catheter 48 may be articulated within the imaging hood to obtain a better image of tissue adjacent to the imaging hood 12. Moreover, articulatable delivery catheter 48 may be articulated to direct an instrument or tool passed through the catheter 48, as described in detail below, to specific areas of tissue imaged through imaging hood 12 without having to reposition deployment catheter 16 and re-clear the imaging field within hood 12.

Figure 3C:
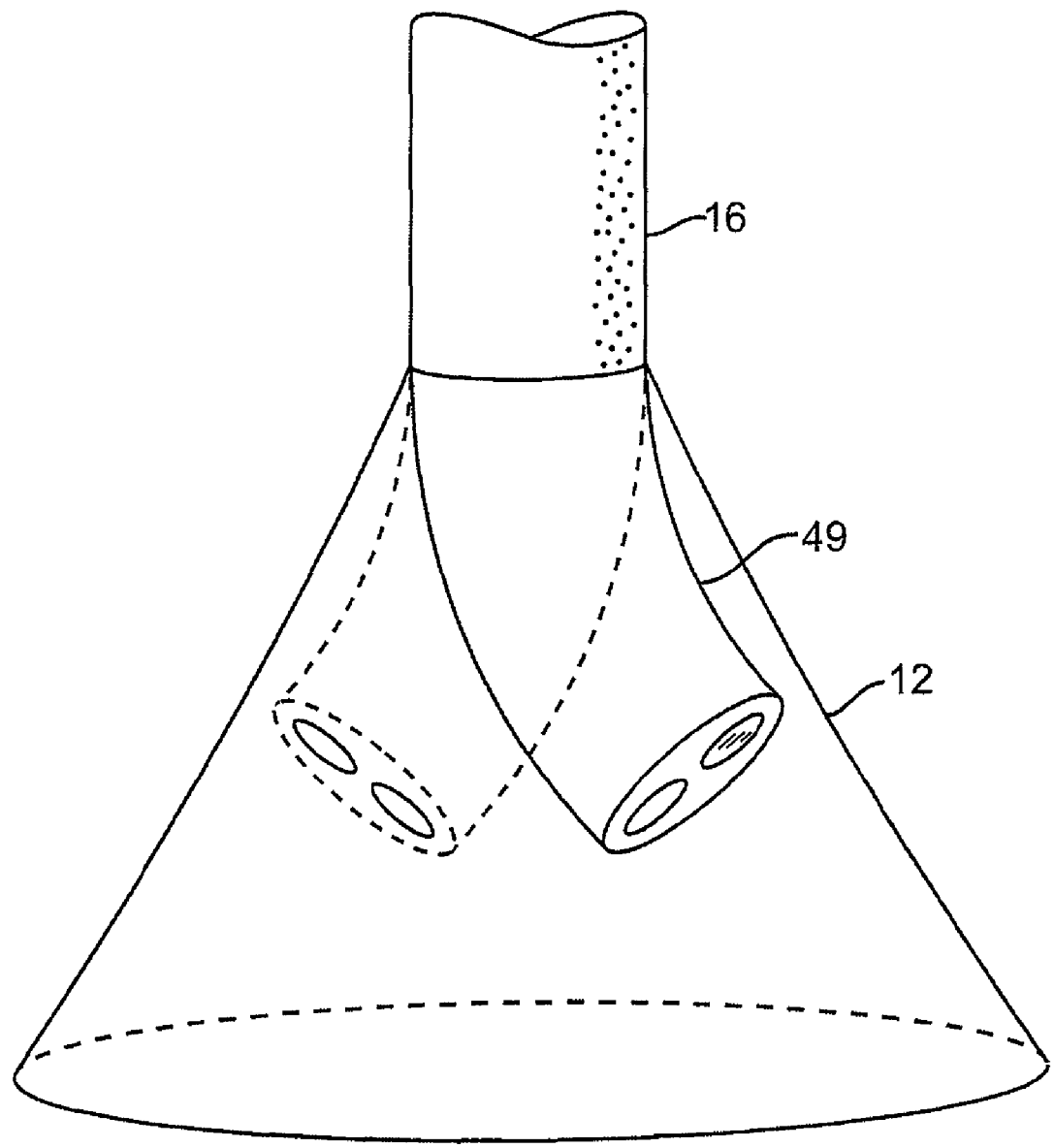

Alternatively, rather than passing an articulatable delivery catheter 48 through the deployment catheter 16, a distal portion of the deployment catheter 16 itself may comprise a distal end 49 which is articulatable within imaging hood 12, as shown in FIG. 3C. Directed imaging, instrument delivery, etc., may be accomplished directly through one or more lumens within deployment catheter 16 to specific regions of the underlying tissue imaged within imaging hood 12.

Figure 4A:
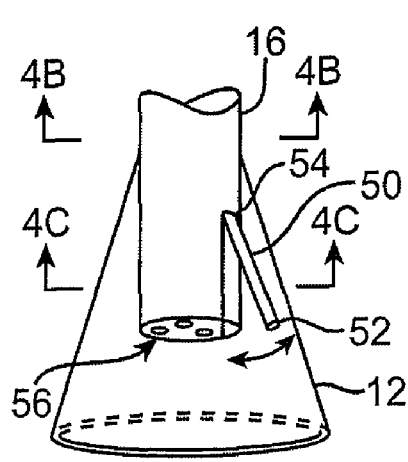
FIGS. 4A to 4C show side and cross-sectional end views, respectively, of another variation having an off-axis imaging capability.

Visualization within the imaging hood 12 may be accomplished through an imaging lumen 20 defined through deployment catheter 16, as described above. In such a configuration, visualization is available in a straight-line manner, i.e., images are generated from the field distally along a longitudinal axis defined by the deployment catheter 16. Alternatively or additionally, an articulatable imaging assembly having a pivotable support member 50 may be connected to, mounted to, or otherwise passed through deployment catheter 16 to provide for visualization off-axis relative to the longitudinal axis defined by deployment catheter 16, as shown in FIG. 4A. Support member 50 may have an imaging element 52, e.g., a CCD or CMOS imager or optical fiber, attached at its distal end with its proximal end connected to deployment catheter 16 via a pivoting connection 54.

Figure 4B:
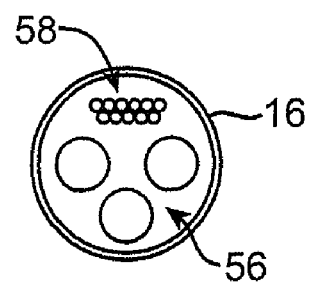
Figure 4C:
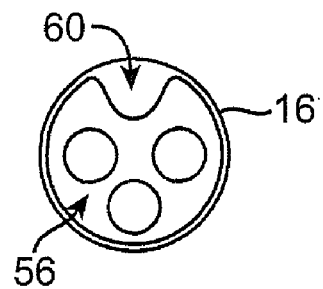

If one or more optical fibers are utilized for imaging, the optical fibers 58 may be passed through deployment catheter 16, as shown in the cross-section of FIG. 4B, and routed through the support member 50. The use of optical fibers 58 may provide for increased diameter sizes of the one or several lumens 56 through deployment catheter 16 for the passage of diagnostic and/or therapeutic tools therethrough. Alternatively, electronic chips, such as a charge coupled device (CCD) or a CMOS imager, which are typically known, may be utilized in place of the optical fibers 58, in which case the electronic imager may be positioned in the distal portion of the deployment catheter 16 with electric wires being routed proximally through the deployment catheter 16. Alternatively, the electronic imagers may be wirelessly coupled to a receiver for the wireless transmission of images. Additional optical fibers or light emitting diodes (LEDs) can be used to provide lighting for the image or operative theater, as described below in further detail. Support member 50 may be pivoted via connection 54 such that the member 50 can be positioned in a low-profile configuration within channel or groove 60 defined in a distal portion of catheter 16, as shown in the cross-section of FIG. 4C. During intravascular delivery of deployment catheter 16 through the patient body, support member 50 can be positioned within channel or groove 60 with imaging hood 12 also in its low-profile configuration. During visualization, imaging hood 12 may be expanded into its deployed configuration and support member 50 may be deployed into its off-axis configuration for imaging the tissue adjacent to hood 12, as in FIG. 4A. Other configurations for support member 50 for off-axis visualization may be utilized, as desired.

FIG. 4D illustrates another variation of a tissue imaging and manipulation assembly 10 with off-axis visualization capabilities. As shown in FIG. 4D, when the hood 12 is in a collapsed position (typically when navigated to a site.) In this variation, the visualization element 52 is adapted such that it may align with an axis of the assembly 10 especially during placement of the assembly 10 at a desired site.

FIG. 4E illustrates the assembly 10 of FIG. 4D when the device reaches the target site. As shown, the hood 12 expands to define the open area. Next, the visualization element 52 may articulate out of alignment with the catheter 16. This configuration permits the device to have a low profile delivery state during delivery and subsequently expand to define the open area. The ability of the visualization element 52 to reposition "off-axis" allows the assembly 10 to accommodate large working instruments through the catheter 16 and substantially reduce the space requirements to accommodate the visualization element. The invention also contemplates placing optical fibers in a similar manner so that the fibers may reposition "off-axis" in a similar manner to the visualization element 52 as depicted. The off-axis visualization allows a more natural operating view akin to how a primate's eyes and hands are positioned relative to one another.

FIG. 4F and FIG. 4G illustrates the assembly 10 where the visualization element 52 is slidable in and out of the hood 12. For instance, when deployed, as shown in FIG. 4F, the visualization element 52 is located along the interior of the hood 12. When in a collapsed position, as shown in FIG. 4G, the visualization element 52 extends out of the hood 12. This variation is useful to allow the hood 12 to compress or collapse to a smaller size without having to accommodate the visualization element 52. Also, the visualization element 52 may be used when navigating the device 10 to a desired site.

Figure 5:
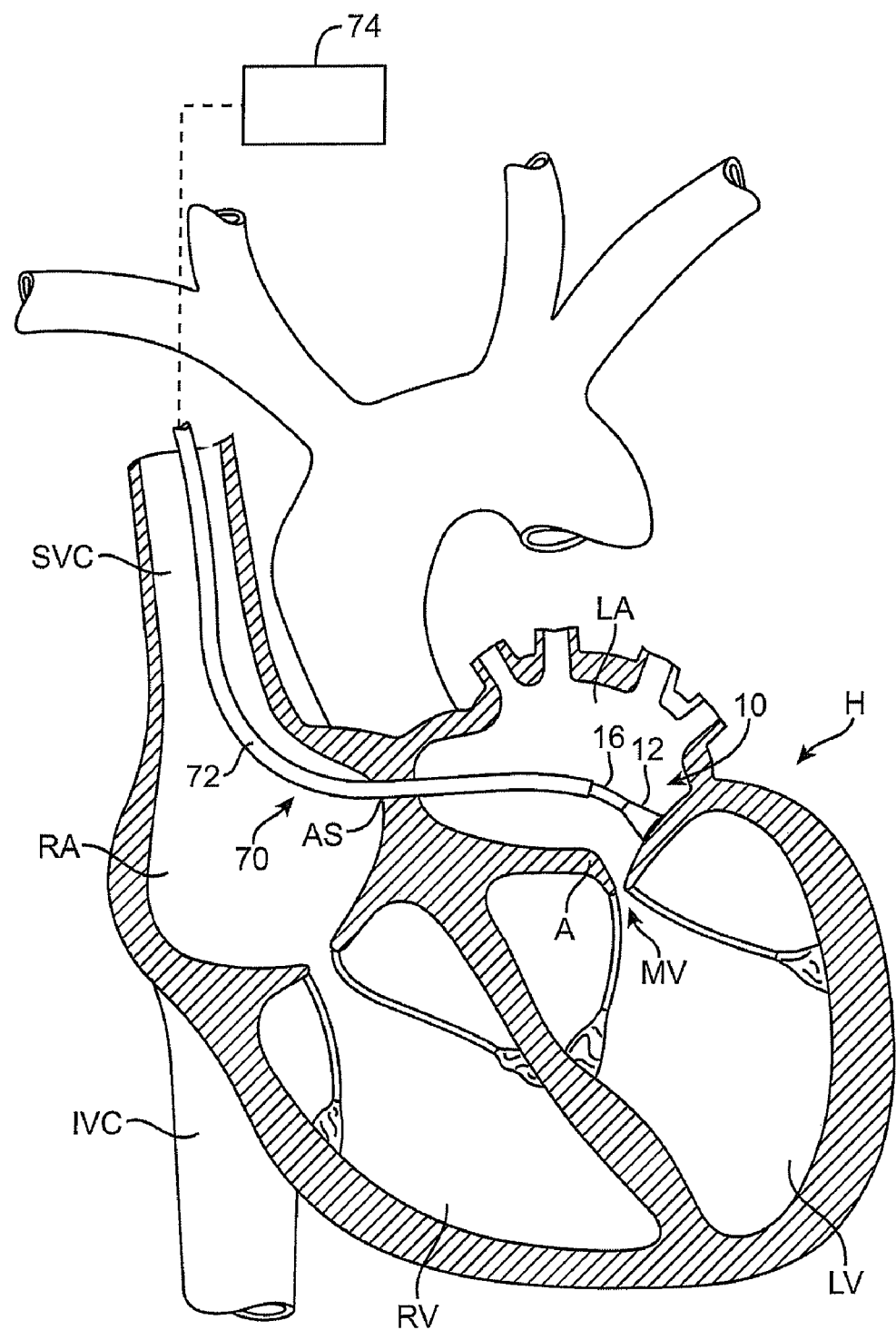
FIG. 5 shows an illustrative view of an example of a tissue imager advanced intravascularly within a heart for imaging tissue regions within an atrial chamber.

FIG. 5 shows an illustrative cross-sectional view of a heart H having tissue regions of interest being viewed via an imaging assembly 10. In this example, delivery catheter assembly 70 may be introduced percutaneously into the patient's vasculature and advanced through the superior vena cava SVC and into the right atrium RA. The delivery catheter or sheath 72 may be articulated through the atrial septum AS and into the left atrium LA for viewing or treating the tissue, e.g., the annulus A, surrounding the mitral valve MV. As shown, deployment catheter 16 and imaging hood 12 may be advanced out of delivery catheter 72 and brought into contact or in proximity to the tissue region of interest. In other examples, delivery catheter assembly 70 may be advanced through the inferior vena cava IVC, if so desired. Moreover, other regions of the heart H, e.g., the right ventricle RV or left ventricle LV, may also be accessed and imaged or treated by imaging assembly 10.

In accessing regions of the heart H or other parts of the body, the delivery catheter or sheath 14 may comprise a conventional intra-vascular catheter or an endoluminal delivery device. Alternatively, robotically-controlled delivery catheters may also be optionally utilized with the imaging assembly described herein, in which case a computer-controller 74 may be used to control the articulation and positioning of the delivery catheter 14. An example of a robotically-controlled delivery catheter which may be utilized is described in further detail in US Pat. Pub. 2002/0087169 A1 to Brock et al. entitled "Flexible Instrument", which is incorporated herein by reference in its entirety. Other robotically-controlled delivery catheters manufactured by Hansen Medical, Inc. (Mountain View, Calif.) may also be utilized with the delivery catheter 14.

Figure 6A:
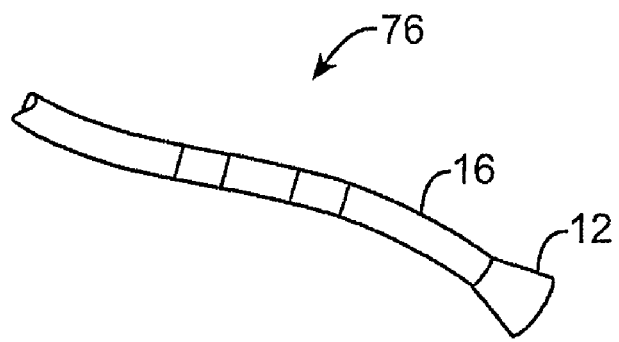
FIGS. 6A to 6C illustrate deployment catheters having one or more optional inflatable balloons or anchors for stabilizing the device during a procedure.
Figure 6B:
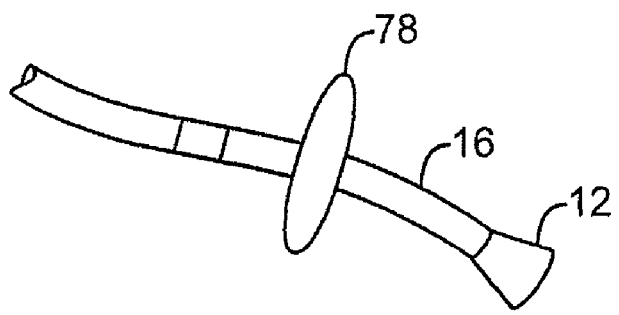
Figure 6C:
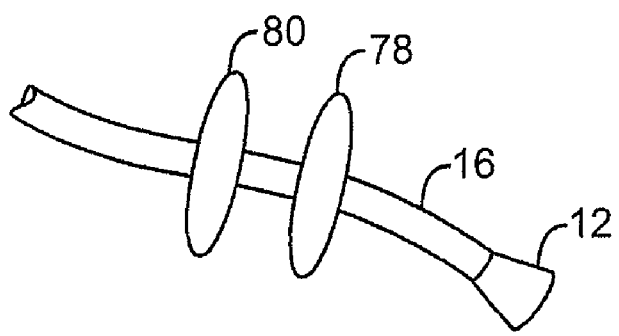

To facilitate stabilization of the deployment catheter 16 during a procedure, one or more inflatable balloons or anchors 76 may be positioned along the length of catheter 16, as shown in FIG. 6A. For example, when utilizing a trans-septal approach across the atrial septum AS into the left atrium LA, the inflatable balloons 76 may be inflated from a low-profile into their expanded configuration to temporarily anchor or stabilize the catheter 16 position relative to the heart H. FIG. 6B shows a first balloon 78 inflated while FIG. 6C also shows a second balloon 80 inflated proximal to the first balloon 78. In such a configuration, the septal wall AS may be wedged or sandwiched between the balloons 78, 80 to temporarily stabilize the catheter 16 and imaging hood 12. A single balloon 78 or both balloons 78, 80 may be used. Other alternatives may utilize expandable mesh members, malecots, or any other temporary expandable structure. After a procedure has been accomplished, the balloon assembly 76 may be deflated or re-configured into a low-profile for removal of the deployment catheter 16.

Figure 7A:
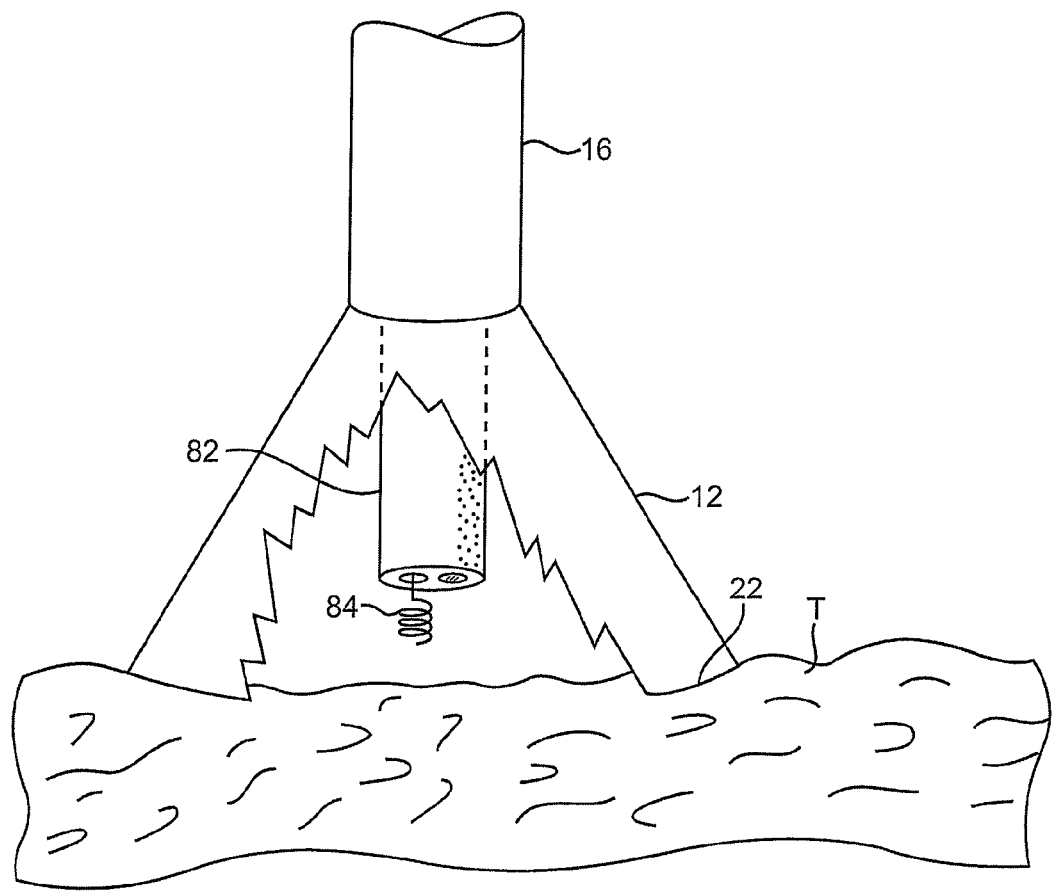
FIGS. 7A and 7B illustrate a variation of an anchoring mechanism such as a helical tissue piercing device for temporarily stabilizing the imaging hood relative to a tissue surface.

To further stabilize a position of the imaging hood 12 relative to a tissue surface to be imaged, various anchoring mechanisms may be optionally employed for temporarily holding the imaging hood 12 against the tissue. Such anchoring mechanisms may be particularly useful for imaging tissue which is subject to movement, e.g., when imaging tissue within the chambers of a beating heart. A tool delivery catheter 82 having at least one instrument lumen and an optional visualization lumen may be delivered through deployment catheter 16 and into an expanded imaging hood 12. As the imaging hood 12 is brought into contact against a tissue surface T to be examined, an anchoring mechanisms such as a helical tissue piercing device 84 may be passed through the tool delivery catheter 82, as shown in FIG. 7A, and into imaging hood 12.

Figure 7B:
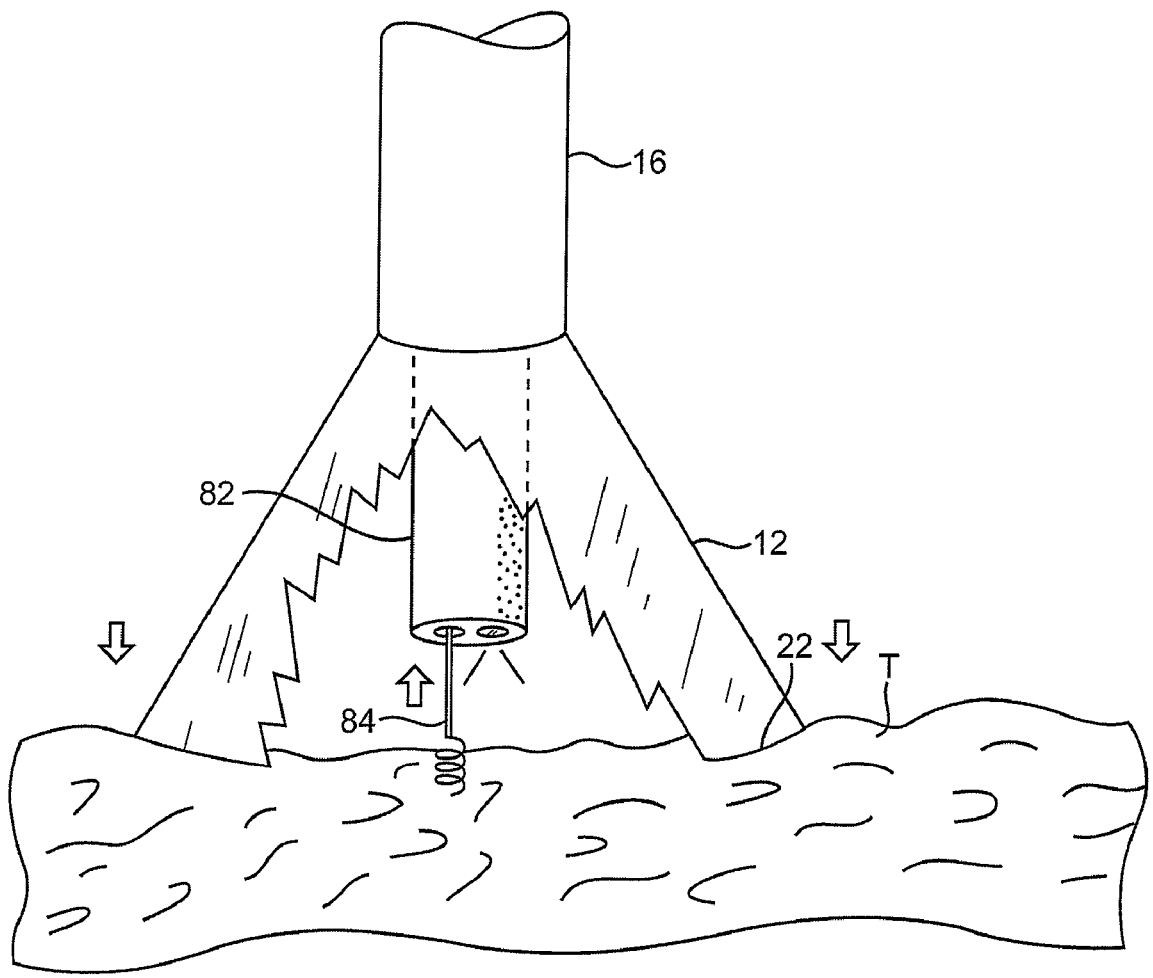

The helical tissue engaging device 84 may be torqued from its proximal end outside the patient body to temporarily anchor itself into the underlying tissue surface T. Once embedded within the tissue T, the helical tissue engaging device 84 may be pulled proximally relative to deployment catheter 16 while the deployment catheter 16 and imaging hood 12 are pushed distally, as indicated by the arrows in FIG. 7B, to gently force the contact edge or lip 22 of imaging hood against the tissue T. The positioning of the tissue engaging device 84 may be locked temporarily relative to the deployment catheter 16 to ensure secure positioning of the imaging hood 12 during a diagnostic or therapeutic procedure within the imaging hood 12. After a procedure, tissue engaging device 84 may be disengaged from the tissue by torquing its proximal end in the opposite direction to remove the anchor form the tissue T and the deployment catheter 16 may be repositioned to another region of tissue where the anchoring process may be repeated or removed from the patient body. The tissue engaging device 84 may also be constructed from other known tissue engaging devices such as vacuum-assisted engagement or grasper-assisted engagement tools, among others.

Although a helical anchor 84 is shown, this is intended to be illustrative and other types of temporary anchors may be utilized, e.g., hooked or barbed anchors, graspers, etc. Moreover, the tool delivery catheter 82 may be omitted entirely and the anchoring device may be delivered directly through a lumen defined through the deployment catheter 16.

Figure 7C:
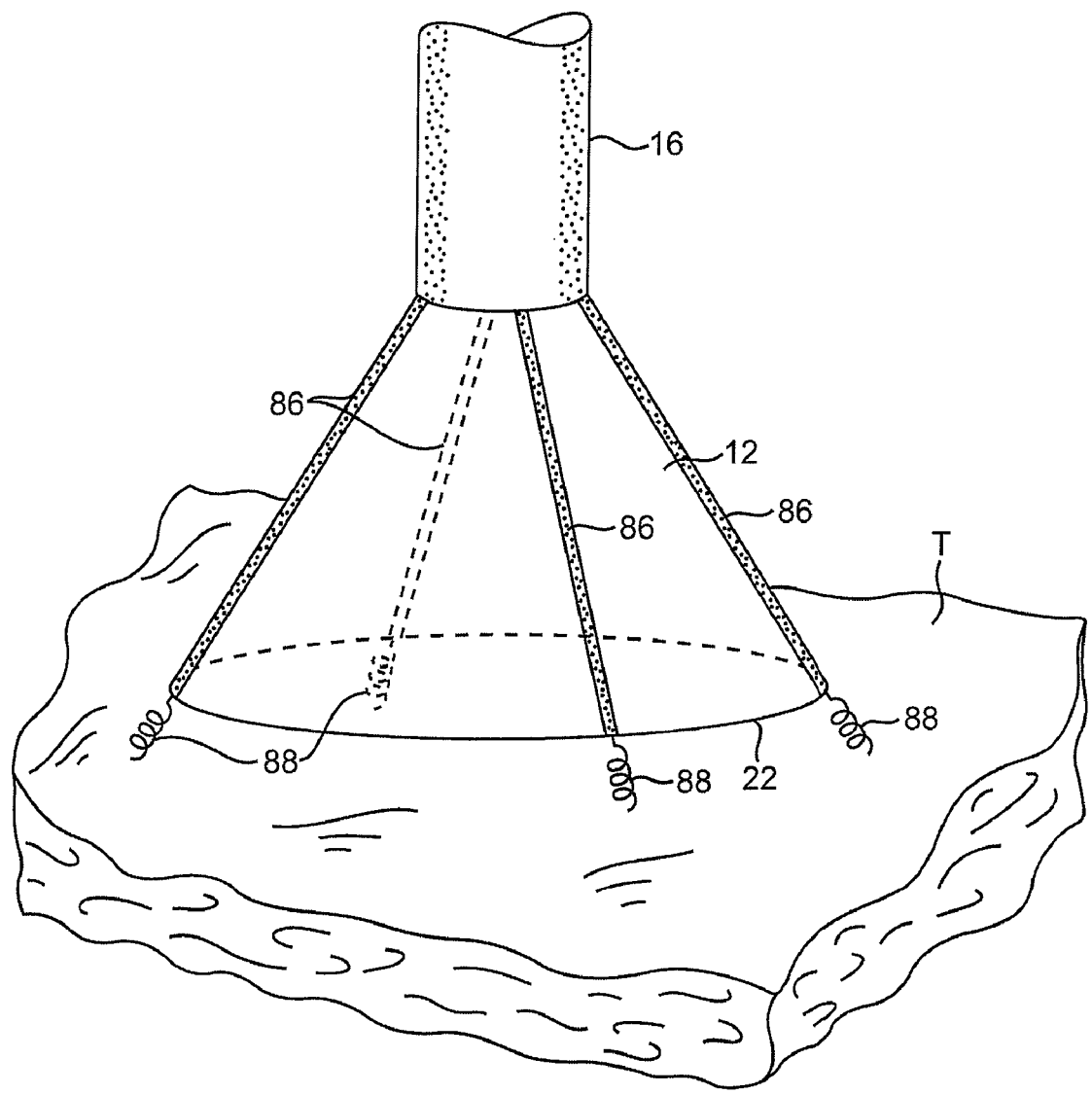
FIG. 7C shows another variation for anchoring the imaging hood having one or more tubular support members integrated with the imaging hood; each support members may define a lumen-therethrough for advancing a helical tissue anchor within.

In another variation where the tool delivery catheter 82 may be omitted entirely to temporarily anchor imaging hood 12, FIG. 7C shows an imaging hood 12 having one or more tubular support members 86, e.g., four support members 86 as shown, integrated with the imaging hood 12. The tubular support members 86 may define lumens therethrough each having helical tissue engaging devices 88 positioned within. When an expanded imaging hood 12 is to be temporarily anchored to the tissue, the helical tissue engaging devices 88 may be urged distally to extend from imaging hood 12 and each may be torqued from its proximal end to engage the underlying tissue T. Each of the helical tissue engaging devices 88 may be advanced through the length of deployment catheter 16 or they may be positioned within tubular support members 86 during the delivery and deployment of imaging hood 12. Once the procedure within imaging hood 12 is finished, each of the tissue engaging devices 88 may be disengaged from the tissue and the imaging hood 12 may be repositioned to another region of tissue or removed from the patient body.

Figure 8A:
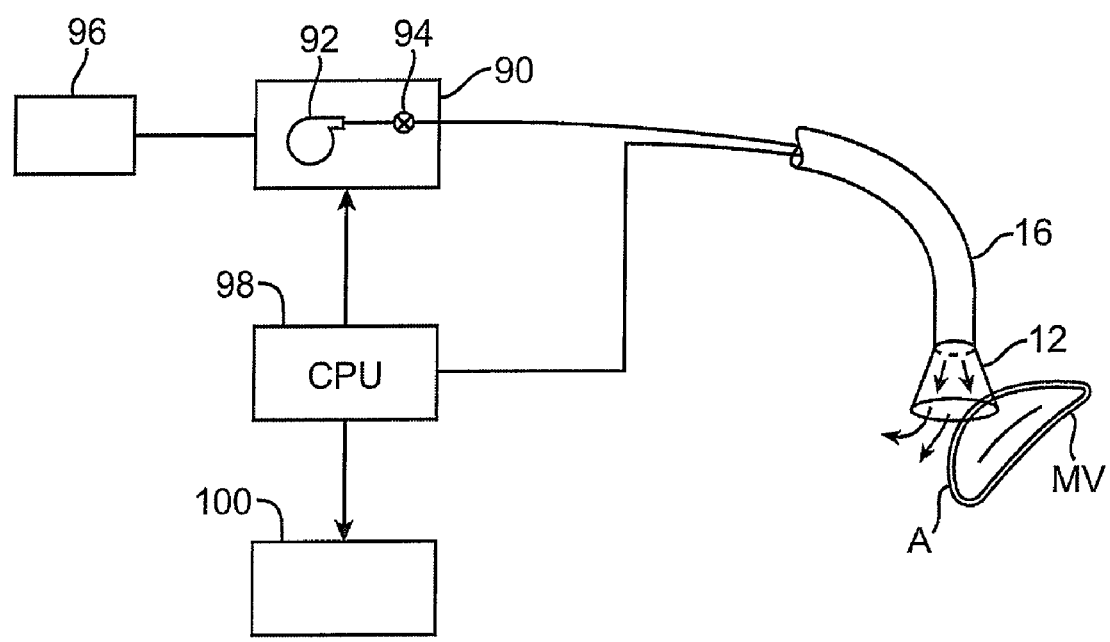
FIG. 8A shows an illustrative example of one variation of how a tissue imager may be utilized with an imaging device.

An illustrative example is shown in FIG. 8A of a tissue imaging assembly connected to a fluid delivery system 90 and to an optional processor 98 and image recorder and/or viewer 100. The fluid delivery system 90 may generally comprise a pump 92 and an optional valve 94 for controlling the flow rate of the fluid into the system. A fluid reservoir 96, fluidly connected to pump 92, may hold the fluid to be pumped through imaging hood 12. An optional central processing unit or processor 98 may be in electrical communication with fluid delivery system 90 for controlling flow parameters such as the flow rate and/or velocity of the pumped fluid. The processor 98 may also be in electrical communication with an image recorder and/or viewer 100 for directly viewing the images of tissue received from within imaging hood 12. Imager recorder and/or viewer 100 may also be used not only to record the image but also the location of the viewed tissue region, if so desired.

Optionally, processor 98 may also be utilized to coordinate the fluid flow and the image capture. For instance, processor 98 may be programmed to provide for fluid flow from reservoir 96 until the tissue area has been displaced of blood to obtain a clear image. Once the image has been determined to be sufficiently clear, either visually by a practitioner or by computer, an image of the tissue may be captured automatically by recorder 100 and pump 92 may be automatically stopped or slowed by processor 98 to cease the fluid flow into the patient. Other variations for fluid delivery and image capture are, of course, possible and the aforementioned configuration is intended only to be illustrative and not limiting.

Figure 8B:
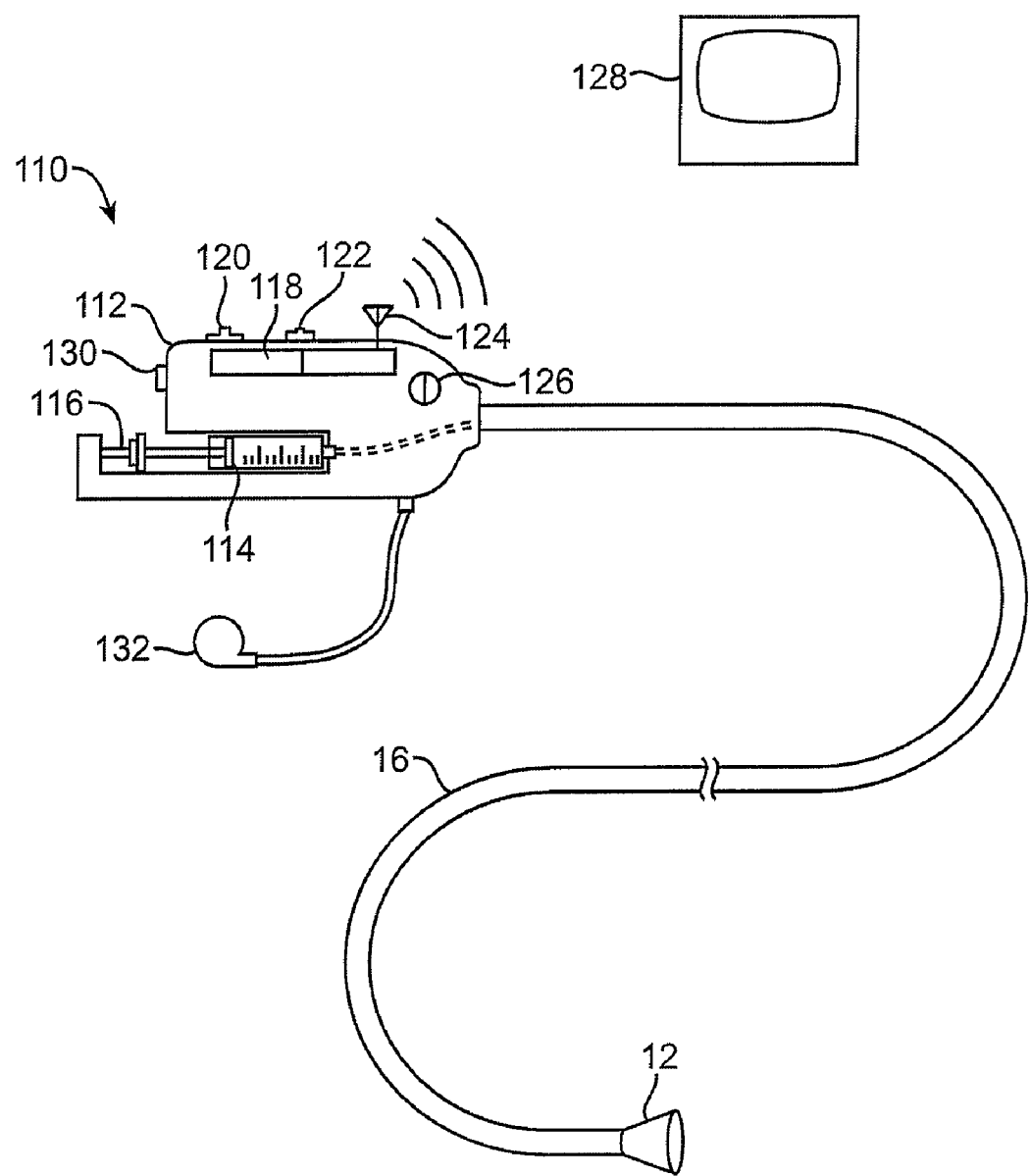
FIG. 8B shows a further illustration of a hand-held variation of the fluid delivery and tissue manipulation system.

FIG. 8B shows a further illustration of a hand-held variation of the fluid delivery and tissue manipulation system 110. In this variation, system 110 may have a housing or handle assembly 112 which can be held or manipulated by the physician from outside the patient body. The fluid reservoir 114, shown in this variation as a syringe, can be fluidly coupled to the handle assembly 112 and actuated via a pumping mechanism 116, e.g., lead screw. Fluid reservoir 114 may be a simple reservoir separated from the handle assembly 112 and fluidly coupled to handle assembly 112 via one or more tubes. The fluid flow rate and other mechanisms may be metered by the electronic controller 118.

Deployment of imaging hood 12 may be actuated by a hood deployment switch 120 located on the handle assembly 112 while dispensation of the fluid from reservoir 114 may be actuated by a fluid deployment switch 122, which can be electrically coupled to the controller 118. Controller 118 may also be electrically coupled to a wired or wireless antenna 124 optionally integrated with the handle assembly 112, as shown in the figure. The wireless antenna 124 can be used to wirelessly transmit images captured from the imaging hood 12 to a receiver, e.g., via Bluetooth® wireless technology (Bluetooth SIG, Inc., Bellevue, Wash.), RF, etc., for viewing on a monitor 128 or for recording for later viewing.

Articulation control of the deployment catheter 16, or a delivery catheter or sheath 14 through which the deployment catheter 16 may be delivered, may be accomplished by computer control, as described above, in which case an additional controller may be utilized with handle assembly 112. In the case of manual articulation, handle assembly 112 may incorporate one or more articulation controls 126 for manual manipulation of the position of deployment catheter 16. Handle assembly 112 may also define one or more instrument ports 130 through which a number of intravascular tools may be passed for tissue manipulation and treatment within imaging hood 12, as described further below. Furthermore, in certain procedures, fluid or debris may be sucked into imaging hood 12 for evacuation from the patient body by optionally fluidly coupling a suction pump 132 to handle assembly 112 or directly to deployment catheter 16.

Figure 9A:
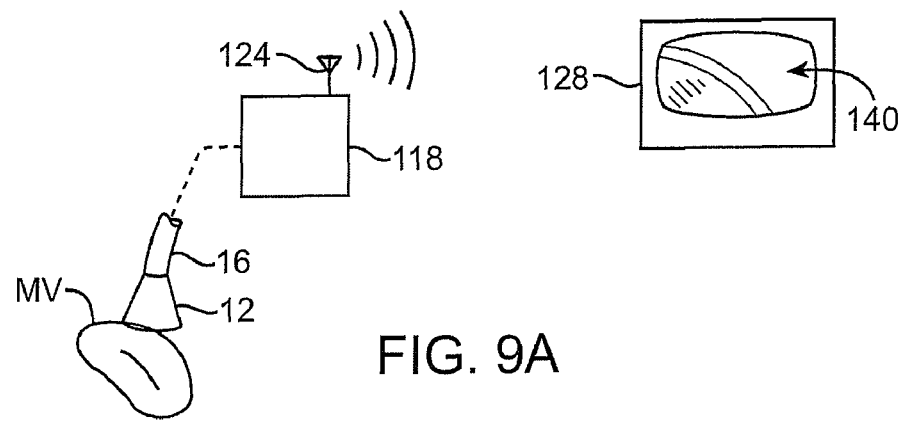
FIGS. 9A to 9C illustrate an example of capturing several images of the tissue at multiple regions.
Figure 9B:
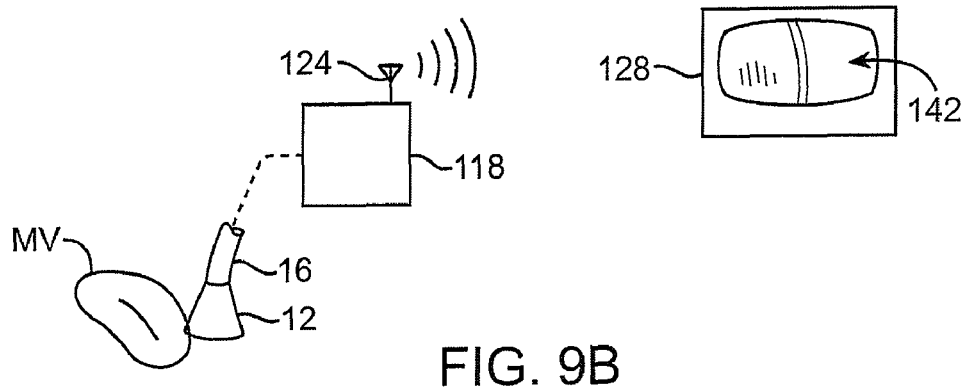
Figure 9C:
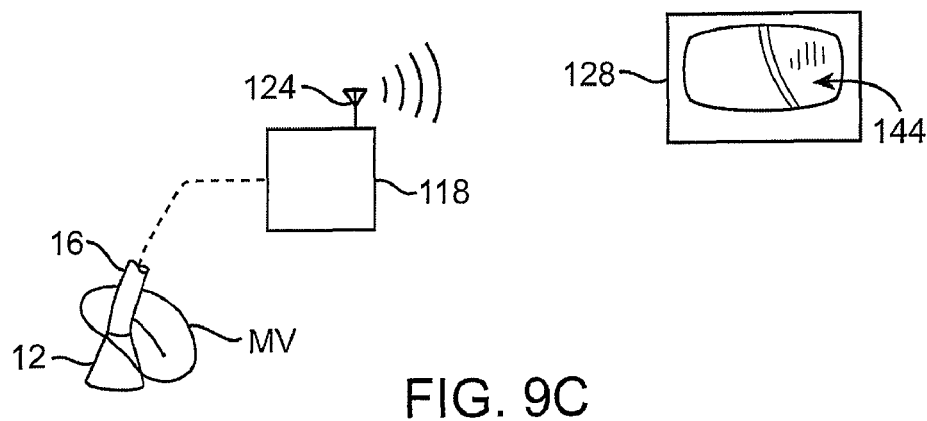

As described above, fluid may be pumped continuously into imaging hood 12 to provide for clear viewing of the underlying tissue. Alternatively, fluid may be pumped temporarily or sporadically only until a clear view of the tissue is available to be imaged and recorded, at which point the fluid flow may cease and the blood may be allowed to seep or flow back into imaging hood 12. FIGS. 9A to 9C illustrate an example of capturing several images of the tissue at multiple regions. Deployment catheter 16 may be desirably positioned and imaging hood 12 deployed and brought into position against a region of tissue to be imaged, in this example the tissue surrounding a mitral valve MV within the left atrium of a patient's heart. The imaging hood 12 may be optionally anchored to the tissue, as described above, and then cleared by pumping the imaging fluid into the hood 12. Once sufficiently clear, the tissue may be visualized and the image captured by control electronics 118. The first captured image 140 may be stored and/or transmitted wirelessly 124 to a monitor 128 for viewing by the physician, as shown in FIG. 9A.

The deployment catheter 16 may be then repositioned to an adjacent portion of mitral valve MV, as shown in FIG. 9B, where the process may be repeated to capture a second image 142 for viewing and/or recording. The deployment catheter 16 may again be repositioned to another region of tissue, as shown in FIG. 9C, where a third image 144 may be captured for viewing and/or recording. This procedure may be repeated as many times as necessary for capturing a comprehensive image of the tissue surrounding mitral valve MV, or any other tissue region. When the deployment catheter 16 and imaging hood 12 is repositioned from tissue region to tissue region, the pump may be stopped during positioning and blood or surrounding fluid may be allowed to enter within imaging hood 12 until the tissue is to be imaged, where the imaging hood 12 may be cleared, as above.

As mentioned above, when the imaging hood 12 is cleared by pumping the imaging fluid within for clearing the blood or other bodily fluid, the fluid may be pumped continuously to maintain the imaging fluid within the hood 12 at a positive pressure or it may be pumped under computer control for slowing or stopping the fluid flow into the hood 12 upon detection of various parameters or until a clear image of the underlying tissue is obtained. The control electronics 118 may also be programmed to coordinate the fluid flow into the imaging hood 12 with various physical parameters to maintain a clear image within imaging hood 12.

Figure 10A:
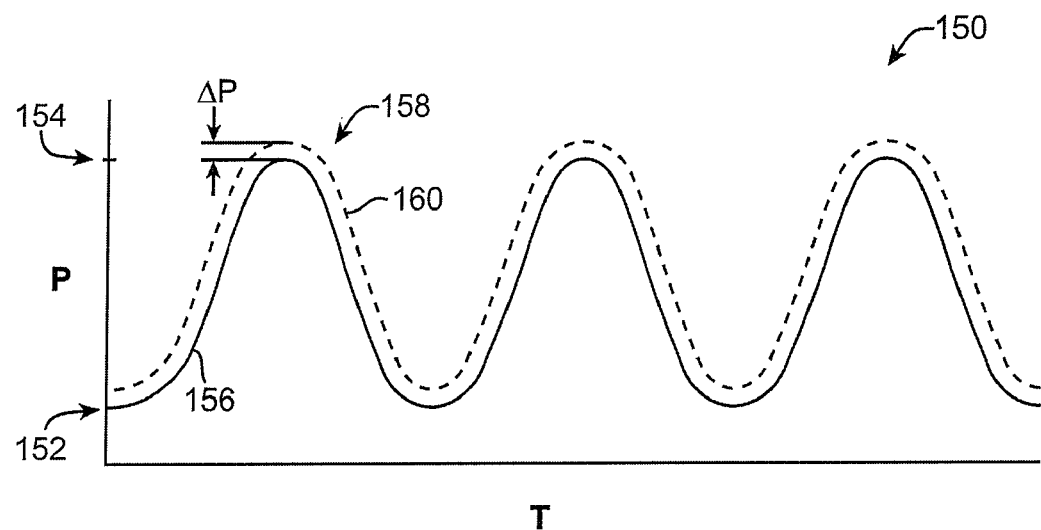
FIGS. 10A and 10B show charts illustrating how fluid pressure within the imaging hood may be coordinated with the surrounding blood pressure; the fluid pressure in the imaging hood may be coordinated with the blood pressure or it may be regulated based upon pressure feedback from the blood.

One example is shown in FIG. 10A which shows a chart 150 illustrating how fluid pressure within the imaging hood 12 may be coordinated with the surrounding blood pressure. Chart 150 shows the cyclical blood pressure 156 alternating between diastolic pressure 152 and systolic pressure 154 over time T due to the beating motion of the patient heart. The fluid pressure of the imaging fluid, indicated by plot 160, within imaging hood 12 may be automatically timed to correspond to the blood pressure changes 160 such that an increased pressure is maintained within imaging hood 12 which is consistently above the blood pressure 156 by a slight increase $\Delta P$, as illustrated by the pressure difference at the peak systolic pressure 158. This pressure difference, $\Delta P$, may be maintained within imaging hood 12 over the pressure variance of the surrounding blood pressure to maintain a positive imaging fluid pressure within imaging hood 12 to maintain a clear view of the underlying tissue. One benefit of maintaining a constant $\Delta P$ is a constant flow and maintenance of a clear field.

Figure 10B:
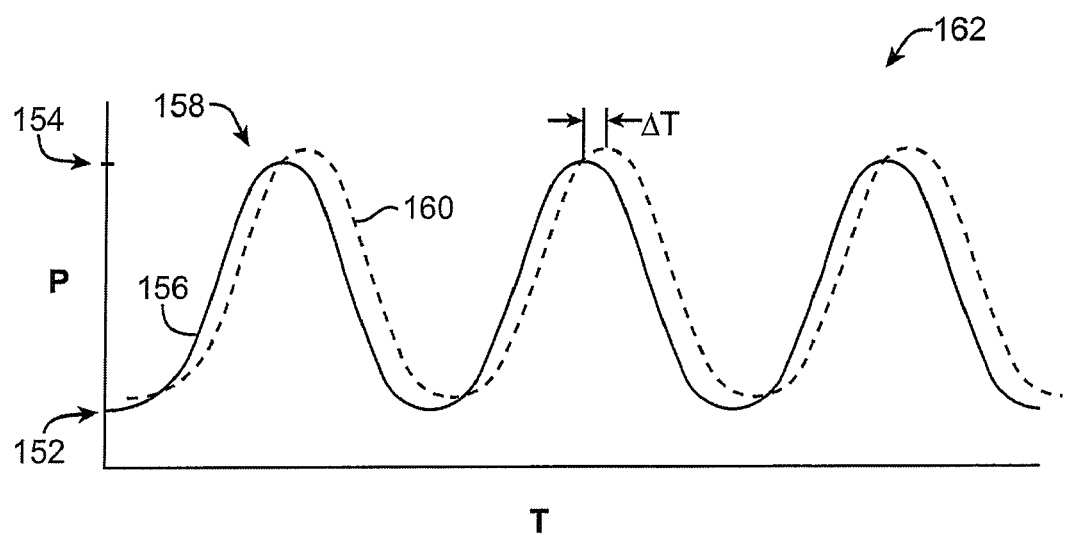

FIG. 10B shows a chart 162 illustrating another variation for maintaining a clear view of the underlying tissue where one or more sensors within the imaging hood 12, as described in further detail below, may be configured to sense pressure changes within the imaging hood 12 and to correspondingly increase the imaging fluid pressure within imaging hood 12. This may result in a time delay, $\Delta T$, as illustrated by the shifted fluid pressure 160 relative to the cycling blood pressure 156, although the time delay $\Delta T$ may be negligible in maintaining the clear image of the underlying tissue. Predictive software algorithms can also be used to substantially eliminate this time delay by predicting when the next pressure wave peak will arrive and by increasing the pressure ahead of the pressure wave's arrival by an amount of time substantially equal to the aforementioned time delay to essentially cancel the time delay out.

The variations in fluid pressure within imaging hood 12 may be accomplished in part due to the nature of imaging hood 12. An inflatable balloon, which is conventionally utilized for imaging tissue, may be affected by the surrounding blood pressure changes. On the other hand, an imaging hood 12 retains a constant volume therewithin and is structurally unaffected by the surrounding blood pressure changes, thus allowing for pressure increases therewithin. The material that hood 12 is made from may also contribute to the manner in which the pressure is modulated within this hood 12. A stiffer hood material, such as high durometer polyurethane or Nylon, may facilitate the maintaining of an open hood when deployed. On the other hand, a relatively lower durometer or softer material, such as a low durometer PVC or polyurethane, may collapse from the surrounding fluid pressure and may not adequately maintain a deployed or expanded hood.

Turning now to the imaging hood, other variations of the tissue imaging assembly may be utilized, as shown in FIG. 11A, which shows another variation comprising an additional imaging balloon 172 within an imaging hood 174. In this variation, an expandable balloon 172 having a translucent skin may be positioned within imaging hood 174. Balloon 172 may be made from any distensible biocompatible material having sufficient translucent properties which allow for visualization therethrough. Once the imaging hood 174 has been deployed against the tissue region of interest, balloon 172 may be filled with a fluid, such as saline, or less preferably a gas, until balloon 172 has been expanded until the blood has been sufficiently displaced. The balloon 172 may thus be expanded proximal to or into contact against the tissue region to be viewed. The balloon 172 can also be filled with contrast media to allow it to be viewed on fluoroscopy to aid in its positioning. The imager, e.g., fiber optic, positioned within deployment catheter 170 may then be utilized to view the tissue region through the balloon 172 and any additional fluid which may be pumped into imaging hood 174 via one or more optional fluid ports 176, which may be positioned proximally of balloon 172 along a portion of deployment catheter 170. Alternatively, balloon 172 may define one or more holes over its surface which allow for seepage or passage of the fluid contained therein to escape and displace the blood from within imaging hood 174.

FIG. 11B shows another alternative in which balloon 180 may be utilized alone. Balloon 180, attached to deployment catheter 178, may be filled with fluid, such as saline or contrast media, and is preferably allowed to come into direct contact with the tissue region to be imaged.

Figure 12A:
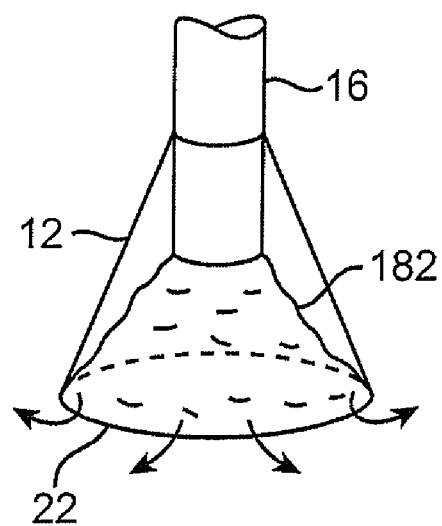
FIG. 12A shows another variation in which a flexible expandable or distensible membrane may be incorporated within the imaging hood to alter the volume of fluid dispensed.

FIG. 12A shows another alternative in which deployment catheter 16 incorporates imaging hood 12, as above, and includes an additional flexible membrane 182 within imaging hood 12. Flexible membrane 182 may be attached at a distal end of catheter 16 and optionally at contact edge 22. Imaging hood 12 may be utilized, as above, and membrane 182 may be deployed from catheter 16 in vivo or prior to placing catheter 16 within a patient to reduce the volume within imaging hood 12. The volume may be reduced or minimized to reduce the amount of fluid dispensed for visualization or may be reduced depending upon the area of tissue to be visualized.

Figure 12B:
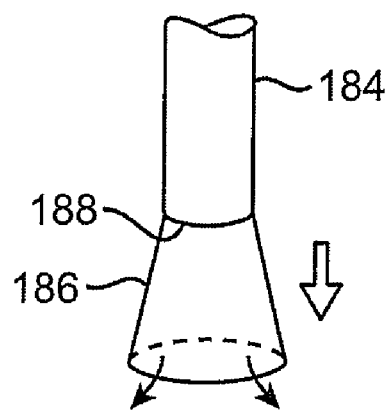
FIGS. 12B and 12C show another variation in which the imaging hood may be partially or selectively deployed from the catheter to alter the area of the tissue being visualized as well as the volume of the dispensed fluid.
Figure 12C:
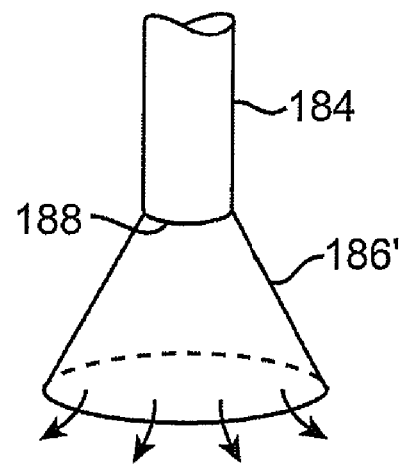

FIGS. 12B and 12C show yet another alternative in which imaging hood 186 may be withdrawn proximally within deployment catheter 184 or deployed distally from catheter 186, as shown, to vary the volume of imaging hood 186 and thus the volume of dispensed fluid. Imaging hood 186 may be seen in FIG. 12B as being partially deployed from, e.g., a circumferentially defined lumen within catheter 184, such as annular lumen 188. The underlying tissue may be visualized with imaging hood 186 only partially deployed. Alternatively, imaging hood 186' may be fully deployed, as shown in FIG. 12C, by urging hood 186' distally out from annular lumen 188. In this expanded configuration, the area of tissue to be visualized may be increased as hood 186' is expanded circumferentially.

Figure 12D:
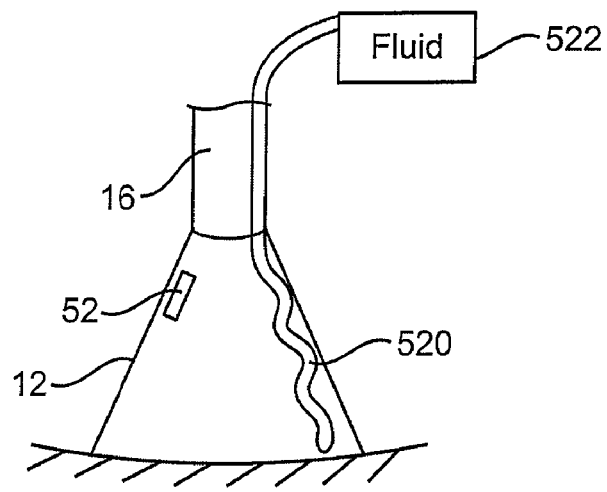
FIGS. 12D-12F show variations of the imaging hood with an inflatable members that displace fluids or other materials from the hood.
Figure 12E:
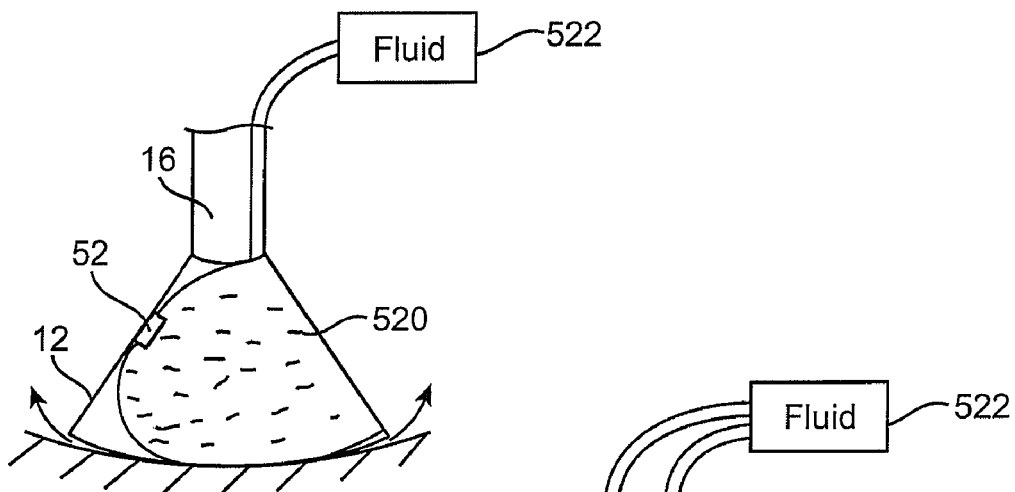
Figure 12F:
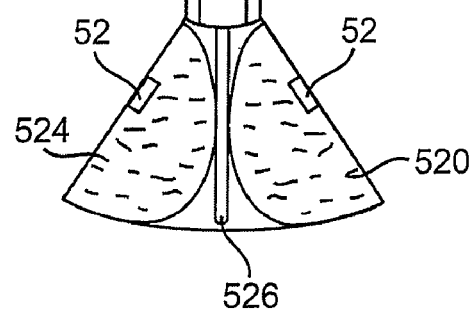

FIG. 12D illustrates another variation of a tissue imaging and manipulation assembly 10. In this variation, the hood 12 includes an inflatable member 520 (e.g., a balloon, bladder, or fillable membrane) that is coupled to a fluid source 522. The inflatable member 520 may be constructed from a clear material. Upon expansion of the hood 12, the inflatable member 520 fills with a clear fluid as shown in FIG. 12E. As the inflatable member 520 expands, it displaces fluids and other substances from within the hood 12 (as shown by the arrows). Because the member 520 and fluid are clear, the visualization element 52 is still able to visualize the tissue in the open area of the hood 12. FIG. 12E illustrates yet another principle of an assembly 10 as described herein. In this variation, the hood 12 includes two or more inflatable members 520, 524. The inflatable members 520, 524 function to displace fluids from the hood 12 while permitting visualization. However, use of two or more inflatable members 520, 524 permits advancement of a tool or device 526 between the inflatable members. In another variation, the inflatable member(s) is constructed from a material having an index of refraction close to or matching that of the displacement liquid. This selection of the index of essentially allows the membrane to "disappear" and not interfere with visualization.

FIGS. 13A and 13B show perspective and cross-sectional side views, respectively, of yet another variation of imaging assembly which may utilize a fluid suction system for minimizing the amount of fluid injected into the patient's heart or other body lumen during tissue visualization. Deployment catheter 190 in this variation may define an inner tubular member 196 which may be integrated with deployment catheter 190 or independently translatable. Fluid delivery lumen 198 defined through member 196 may be fluidly connected to imaging hood 192, which may also define one or more open channels 194 over its contact lip region. Fluid pumped through fluid delivery lumen 198 may thus fill open area 202 to displace any blood or other fluids or objects therewithin. As the clear fluid is forced out of open area 202, it may be sucked or drawn immediately through one or more channels 194 and back into deployment catheter 190. Tubular member 196 may also define one or more additional working channels 200 for the passage of any tools or visualization devices.

In deploying the imaging hood in the examples described herein, the imaging hood may take on any number of configurations when positioned or configured for a low-profile delivery within the delivery catheter, as shown in the examples of FIGS. 14A to 14D. These examples are intended to be illustrative and are not intended to be limiting in scope. FIG. 14A shows one example in which imaging hood 212 may be compressed within catheter 210 by folding hood 212 along a plurality of pleats. Hood 212 may also comprise scaffolding or frame 214 made of a super-elastic or shape memory material or alloy, e.g., Nitinol, Elgiloy, shape memory polymers, electroactive polymers, or a spring stainless steel. The shape memory material may act to expand or deploy imaging hood 212 into its expanded configuration when urged in the direction of the arrow from the constraints of catheter 210.

FIG. 14B shows another example in which imaging hood 216 may be expanded or deployed from catheter 210 from a folded and overlapping configuration. Frame or scaffolding 214 may also be utilized in this example. FIG. 14C shows yet another example in which imaging hood 218 may be rolled, inverted, or everted upon itself for deployment. In yet another example, FIG. 14D shows a configuration in which imaging hood 220 may be fabricated from an extremely compliant material which allows for hood 220 to be simply compressed into a low-profile shape. From this low-profile compressed shape, simply releasing hood 220 may allow for it to expand into its deployed configuration, especially if a scaffold or frame of a shape memory or superelastic material, e.g., Nitinol, is utilized in its construction.

Another variation for expanding the imaging hood is shown in FIGS. 15A and 15B which illustrates a helically expanding frame or support 230. In its constrained low-profile configuration, shown in FIG. 15A, helical frame 230 may be integrated with the imaging hood 12 membrane. When free to expand, as shown in FIG. 15B, helical frame 230 may expand into a conical or tapered shape. Helical frame 230 may alternatively be made out of heat-activated Nitinol to allow it to expand upon application of a current.

FIGS. 16A and 16B show yet another variation in which imaging hood 12 may comprise one or more hood support members 232 integrated with the hood membrane. These longitudinally attached support members 232 may be pivotably attached at their proximal ends to deployment catheter 16. One or more pullwires 234 may be routed through the length of deployment catheter 16 and extend through one or more openings 238 defined in deployment catheter 16 proximally to imaging hood 12 into attachment with a corresponding support member 232 at a pullwire attachment point 236. The support members 232 may be fabricated from a plastic or metal, such as stainless steel. Alternatively, the support members 232 may be made from a superelastic or shape memory alloy, such as Nitinol, which may self-expand into its deployed configuration without the use or need of pullwires. A heat-activated Nitinol may also be used which expands upon the application of thermal energy or electrical energy. In another alternative, support members 232 may also be constructed as inflatable lumens utilizing, e.g., PET balloons. From its low-profile delivery configuration shown in FIG. 16A, the one or more pullwires 234 may be tensioned from their proximal ends outside the patient body to pull a corresponding support member 232 into a deployed configuration, as shown in FIG. 16B, to expand imaging hood 12. To reconfigure imaging hood 12 back into its low profile, deployment catheter 16 may be pulled proximally into a constraining catheter or the pullwires 234 may be simply pushed distally to collapse imaging hood 12.

Figure 17A:
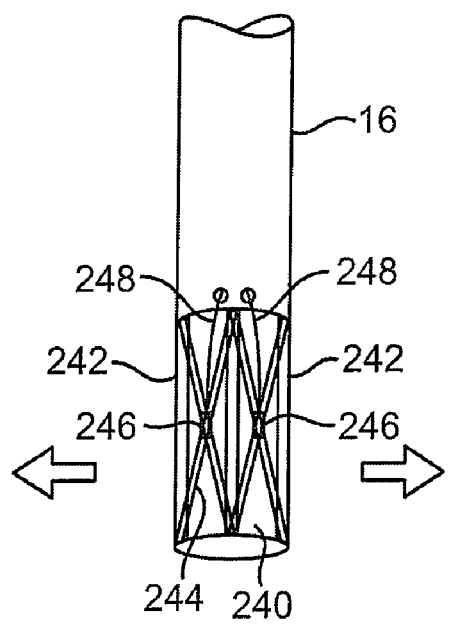
FIGS. 17A and 17B show yet another variation of the imaging hood having at least two or more longitudinally positioned support members supporting the imaging hood membrane where the support members are movable relative to one another via a torquing or pulling or pushing force.
Figure 17B:
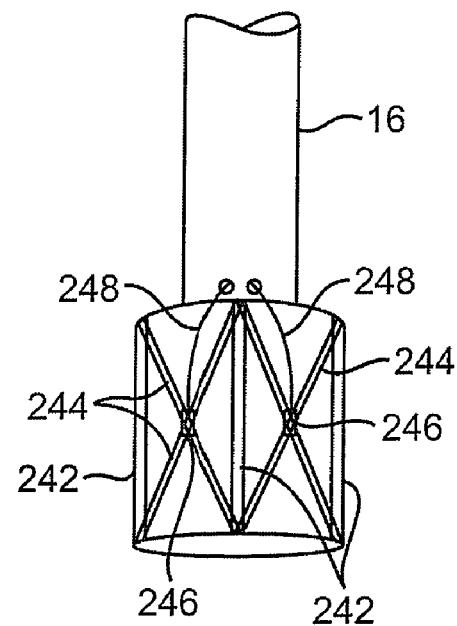

FIGS. 17A and 17B show yet another variation of imaging hood 240 having at least two or more longitudinally positioned support members 242 supporting the imaging hood membrane. The support members 242 each have cross-support members 244 which extend diagonally between and are pivotably attached to the support members 242. Each of the cross-support members 244 may be pivotably attached to one another where they intersect between the support members 242. A jack or screw member 246 may be coupled to each cross-support member 244 at this intersection point and a torquing member, such as a torqueable wire 248, may be coupled to each jack or screw member 246 and extend proximally through deployment catheter 16 to outside the patient body. From outside the patient body, the torqueable wires 248 may be torqued to turn the jack or screw member 246 which in turn urges the cross-support members 244 to angle relative to one another and thereby urge the support members 242 away from one another. Thus, the imaging hood 240 may be transitioned from its low-profile, shown in FIG. 17A, to its expanded profile, shown in FIG. 17B, and back into its low-profile by torquing wires 248.

Figure 18A:
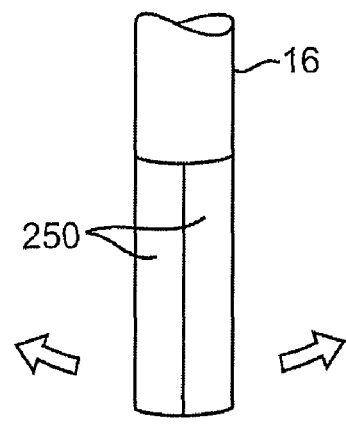
FIGS. 18A and 18B show another variation where a distal portion of the deployment catheter may have several pivoting members which form a tubular shape in its low profile configuration.
Figure 18B:
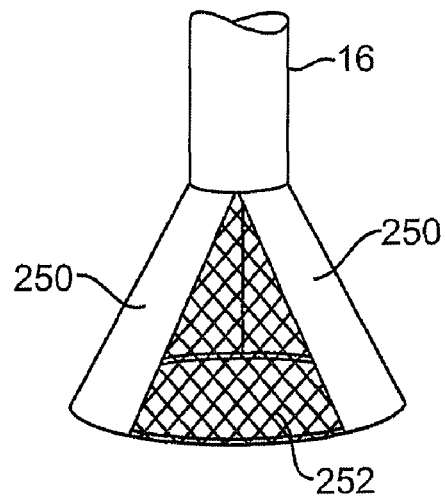

FIGS. 18A and 18B show yet another variation on the imaging hood and its deployment. As shown, a distal portion of deployment catheter 16 may have several pivoting members 250, e.g., two to four sections, which form a tubular shape in its low profile configuration, as shown in FIG. 18A. When pivoted radially about deployment catheter 16, pivoting members 250 may open into a deployed configuration having distensible or expanding membranes 252 extending over the gaps in-between the pivoting members 250, as shown in FIG. 18B. The distensible membrane 252 may be attached to the pivoting members 250 through various methods, e.g., adhesives, such that when the pivoting members 250 are fully extended into a conical shape, the pivoting members 250 and membrane 252 form a conical shape for use as an imaging hood. The distensible membrane 252 may be made out of a porous material such as a mesh or PTFE or out of a translucent or transparent polymer such as polyurethane, PVC, Nylon, etc.

Figure 19A:
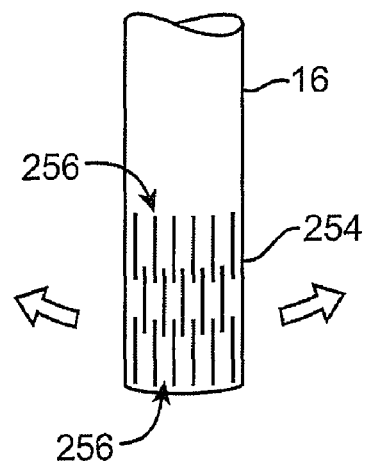
FIGS. 19A and 19B show another variation where the distal portion of deployment catheter may be fabricated from a flexible metallic or polymeric material to form a radially expanding hood.
Figure 19B:
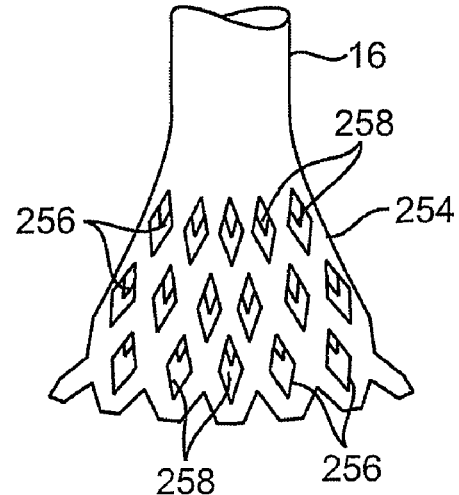

FIGS. 19A and 19B show yet another variation where the distal portion of deployment catheter 16 may be fabricated from a flexible metallic or polymeric material to form a radially expanding hood 254. A plurality of slots 256 may be formed in a uniform pattern over the distal portion of deployment catheter 16, as shown in FIG. 19A. The slots 256 may be formed in a pattern such that when the distal portion is urged radially open, utilizing any of the methods described above, a radially expanded and conically-shaped hood 254 may be formed by each of the slots 256 expanding into an opening, as shown in FIG. 19B. A distensible membrane 258 may overlie the exterior surface or the interior surface of the hood 254 to form a fluid-impermeable hood 254 such that the hood 254 may be utilized as an imaging hood. Alternatively, the distensible membrane 258 may alternatively be formed in each opening 258 to form the fluid-impermeable hood 254. Once the imaging procedure has been completed, hood 254 may be retracted into its low-profile configuration.

Figure 20A:
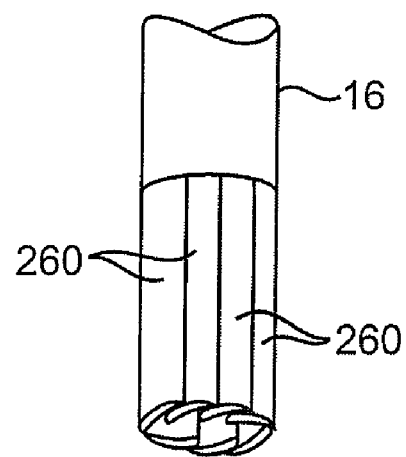
FIGS. 20A and 20B show another variation where the imaging hood may be formed from a plurality of overlapping hood members which overlie one another in an overlapping pattern.
Figure 20B:
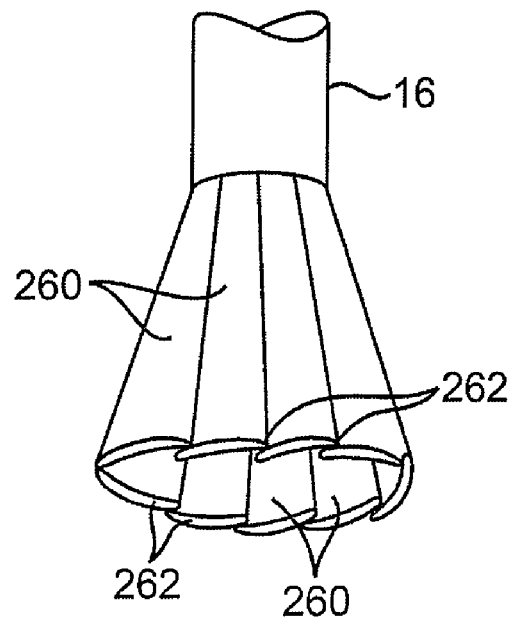

Yet another configuration for the imaging hood may be seen in FIGS. 20A and 20B where the imaging hood may be formed from a plurality of overlapping hood members 260 which overlie one another in an overlapping pattern. When expanded, each of the hood members 260 may extend radially outward relative to deployment catheter 16 to form a conically-shaped imaging hood, as shown in FIG. 20B. Adjacent hood members 260 may overlap one another along an overlapping interface 262 to form a fluid-retaining surface within the imaging hood. Moreover, the hood members 260 may be made from any number of biocompatible materials, e.g., Nitinol, stainless steel, polymers, etc., which are sufficiently strong to optionally retract surrounding tissue from the tissue region of interest.

Figure 20C:
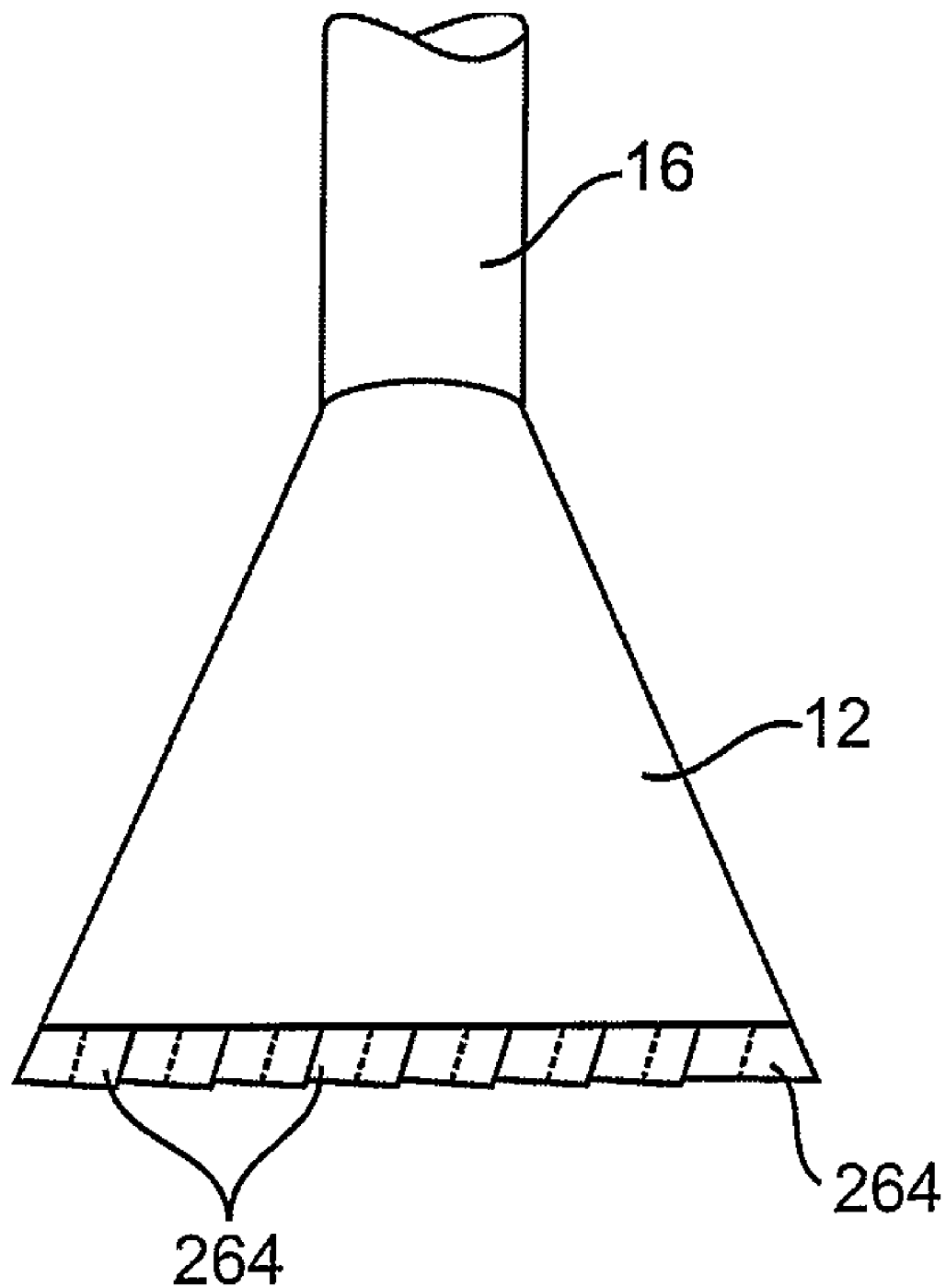
FIG. 20C shows a variation of a hood having a conforming section at the distal end.

FIG. 20C illustrates another variation of a hood 12 under the present invention. In this variation, the hood 12 includes a plurality of sections 264 that overlap on at least one side. The overlapping sections 264 aid in conforming the distal end of the hood against irregularly shaped tissue. The overlapping sections 264 may be affixed to the end of the hood 12. Alternatively, the overlapping sections may extend a substantial length of the hood (not shown). Any number of sections 264 may be used with the hood. For example, when used against tissue having an irregular surface, the device may include a large number of sections such that the end of the hood 12 has a "brush-like" appearance. Alternatively, a variation of the device may have fewer sections (as few as 2). Such a variation may be appropriately configured for use against relatively a smooth tissue surface. The sections 264 may be fabricated from a polymer, cloth, or membrane filled structure. Regardless of construction, the sections 264 improve conformation of the hood against tissue.

Figure 21A:
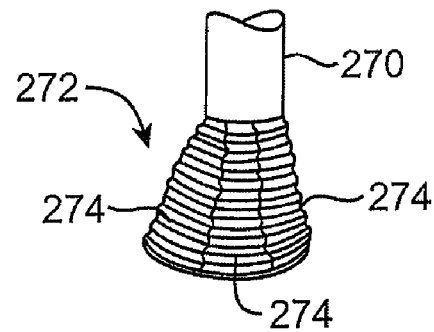
FIGS. 21A and 21B show another example of an expandable hood which is highly conformable against tissue anatomy with varying or non-uniform surfaces.
Figure 21B:
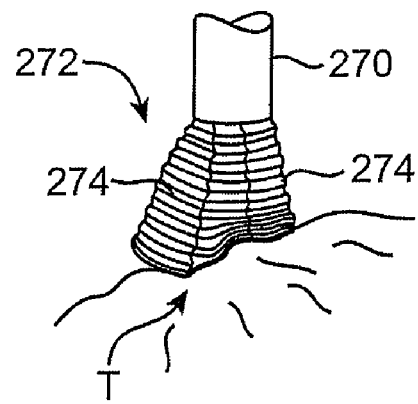

Although it is generally desirable to have an imaging hood contact against a tissue surface in a normal orientation, the imaging hood may be alternatively configured to contact the tissue surface at an acute angle. An imaging hood configured for such contact against tissue may also be especially suitable for contact against tissue surfaces having an unpredictable or uneven anatomical geography. For instance, as shown in the variation of FIG. 21A, deployment catheter 270 may have an imaging hood 272 that is configured to be especially compliant. In this variation, imaging hood 272 may be comprised of one or more sections 274 that are configured to fold or collapse, e.g., by utilizing a pleated surface. Thus, as shown in FIG. 21B, when imaging hood 272 is contacted against uneven tissue surface T, sections 274 are able to conform closely against the tissue. These sections 274 may be individually collapsible by utilizing an accordion style construction to allow conformation, e.g., to the trabeculae in the heart or the uneven anatomy that may be found inside the various body lumens.

Figure 22A:
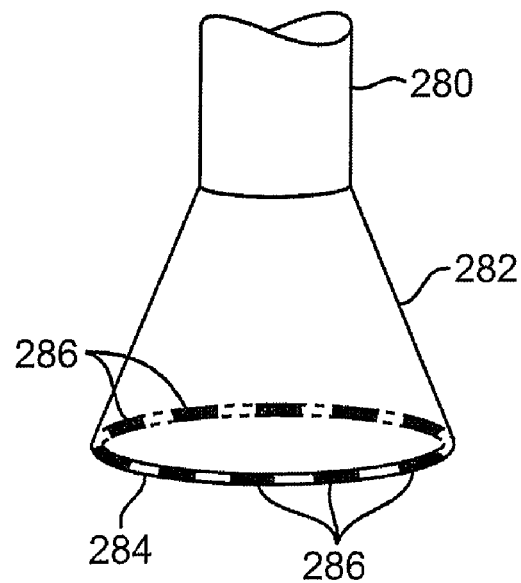
FIG. 22A shows yet another example of an expandable hood having a number of optional electrodes placed about the contact edge or lip of the hood for sensing tissue contact or detecting arrhythmias.

In yet another alternative, FIG. 22A shows another variation in which an imaging hood 282 is attached to deployment catheter 280. The contact lip or edge 284 may comprise one or more electrical contacts 286 positioned circumferentially around contact edge 284. The electrical contacts 286 may be configured to contact the tissue and indicate affirmatively whether tissue contact was achieved, e.g., by measuring the differential impedance between blood and tissue. Alternatively, a processor, e.g., processor 98, in electrical communication with contacts 286 may be configured to determine what type of tissue is in contact with electrical contacts 286. In yet another alternative, the processor 98 may be configured to measure any electrical activity that may be occurring in the underlying tissue, e.g., accessory pathways, for the purposes of electrically mapping the cardiac tissue and subsequently treating, as described below, any arrhythmias which may be detected.

Figure 22B:
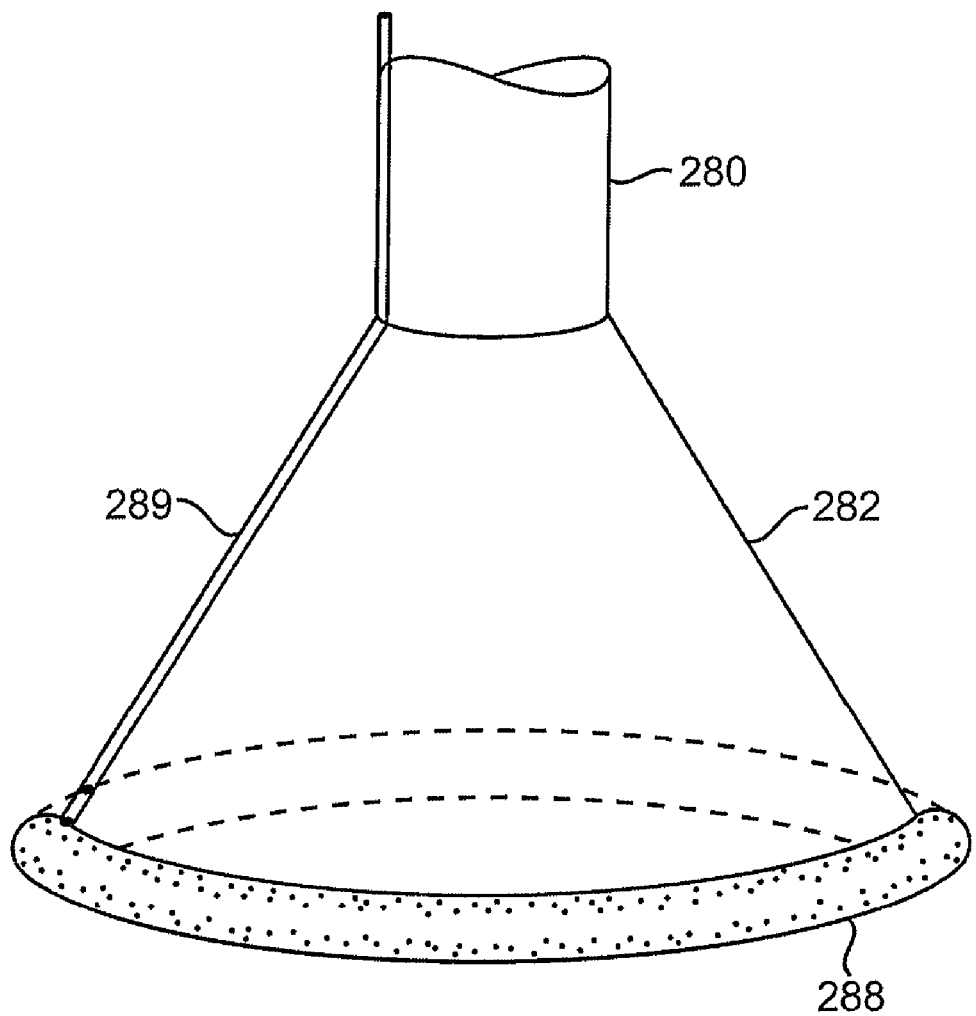
FIG. 22B shows another variation for conforming the imaging hood against the underlying tissue where an inflatable contact edge may be disposed around the circumference of the imaging hood.

Another variation for ensuring contact between imaging hood 282 and the underlying tissue may be seen in FIG. 22B. This variation may have an inflatable contact edge 288 around the circumference of imaging hood 282. The inflatable contact edge 288 may be inflated with a fluid or gas through inflation lumen 289 when the imaging hood 282 is to be placed against a tissue surface having an uneven or varied anatomy. The inflated circumferential surface 288 may provide for continuous contact over the hood edge by conforming against the tissue surface and facilitating imaging fluid retention within hood 282.

Figure 23:
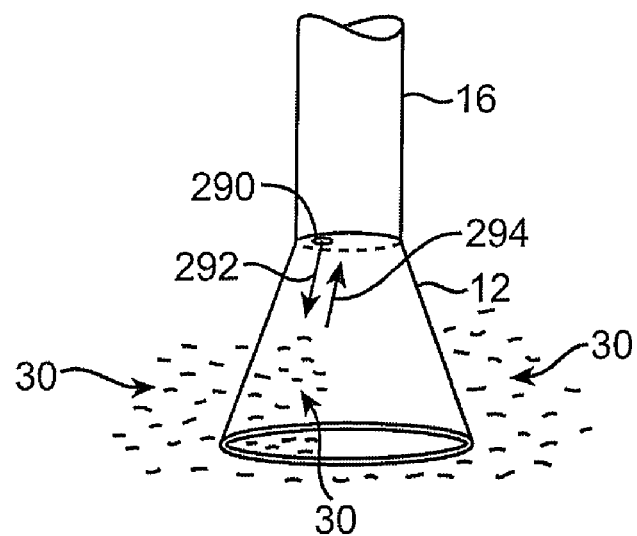
FIG. 23 shows a variation of the system which may be instrumented with a transducer for detecting the presence of blood seeping back into the imaging hood.

Aside from the imaging hood, various instrumentation may be utilized with the imaging and manipulation system. For instance, after the field within imaging hood 12 has been cleared of the opaque blood and the underlying tissue is visualized through the clear fluid, blood may seep back into the imaging hood 12 and obstruct the view. One method for automatically maintaining a clear imaging field may utilize a transducer, e.g., an ultrasonic transducer 290, positioned at the distal end of deployment catheter within the imaging hood 12, as shown in FIG. 23. The transducer 290 may send an energy pulse 292 into the imaging hood 12 and wait to detect back-scattered energy 294 reflected from debris or blood within the imaging hood 12. If back-scattered energy is detected, the pump may be actuated automatically to dispense more fluid into the imaging hood until the debris or blood is no longer detected.

Figure 24A:
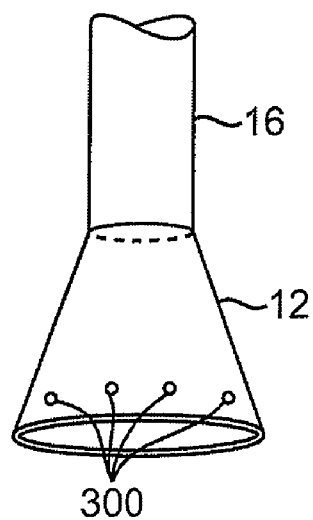
FIGS. 24A and 24B show variations of the imaging hood instrumented with sensors for detecting various physical parameters; the sensors may be instrumented around the outer surface of the imaging hood and also within the imaging hood.

Alternatively, one or more sensors 300 may be positioned on the imaging hood 12 itself, as shown in FIG. 24A, to detect a number of different parameters. For example, sensors 300 may be configured to detect for the presence of oxygen in the surrounding blood, blood and/or imaging fluid pressure, color of the fluid within the imaging hood, etc. Fluid color may be particularly useful in detecting the presence of blood within the imaging hood 12 by utilizing a reflective type sensor to detect back reflection from blood. Any reflected light from blood which may be present within imaging hood 12 may be optically or electrically transmitted through deployment catheter 16 and to a red colored filter within control electronics 118. Any red color which may be detected may indicate the presence of blood and trigger a signal to the physician or automatically actuate the pump to dispense more fluid into the imaging hood 12 to clear the blood.

Alternative methods for detecting the presence of blood within the hood 12 may include detecting transmitted light through the imaging fluid within imaging hood 12. If a source of white light, e.g., utilizing LEDs or optical fibers, is illuminated inside imaging hood 12, the presence of blood may cause the color red to be filtered through this fluid. The degree or intensity of the red color detected may correspond to the amount of blood present within imaging hood 12. A red color sensor can simply comprise, in one variation, a phototransistor with a red transmitting filter over it which can establish how much red light is detected, which in turn can indicate the presence of blood within imaging hood 12. Once blood is detected, the system may pump more clearing fluid through and enable closed loop feedback control of the clearing fluid pressure and flow level.

Figure 24B:
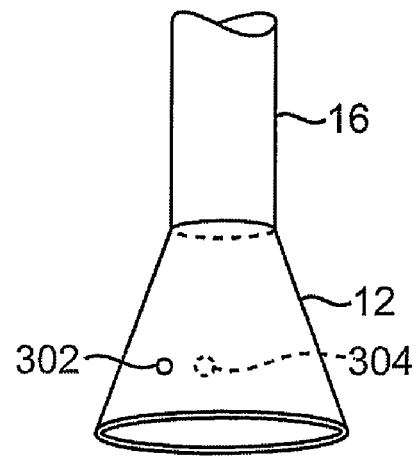

Any number of sensors may be positioned along the exterior 302 of imaging hood 12 or within the interior 304 of imaging hood 12 to detect parameters not only exteriorly to imaging hood 12 but also within imaging hood 12. Such a configuration, as shown in FIG. 24B, may be particularly useful for automatically maintaining a clear imaging field based upon physical parameters such as blood pressure, as described above for FIGS. 10A and 10B.

Figure 25A:
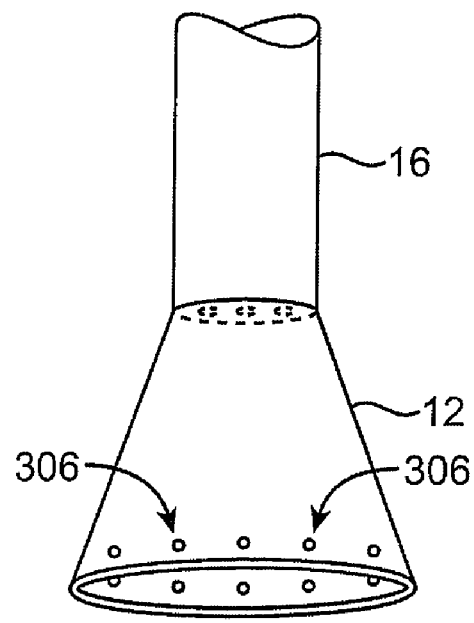
FIGS. 25A and 25B show a variation where the imaging hood may have one or more LEDs over the hood itself for providing illumination of the tissue to be visualized.
Figure 25B:
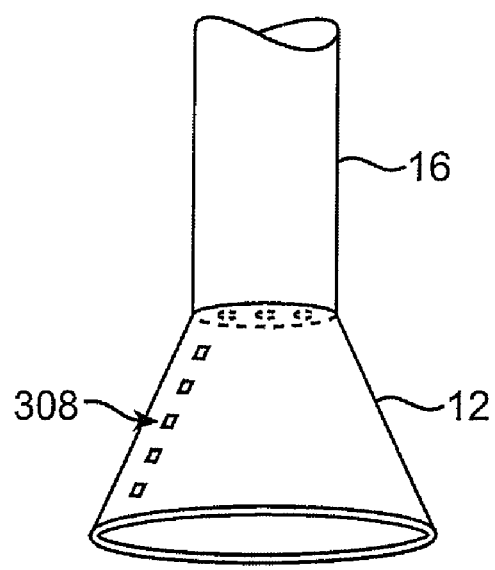

Aside from sensors, one or more light emitting diodes (LEDs) may be utilized to provide lighting within the imaging hood 12. Although illumination may be provided by optical fibers routed through deployment catheter 16, the use of LEDs over the imaging hood 12 may eliminate the need for additional optical fibers for providing illumination. The electrical wires connected to the one or more LEDs may be routed through or over the hood 12 and along an exterior surface or extruded within deployment catheter 16. One or more LEDs may be positioned in a circumferential pattern 306 around imaging hood 12, as shown in FIG. 25A, or in a linear longitudinal pattern 308 along imaging hood 12, as shown in FIG. 25B. Other patterns, such as a helical or spiral pattern, may also be utilized. Alternatively, LEDs may be positioned along a support member forming part of imaging hood 12.

Figure 26A:
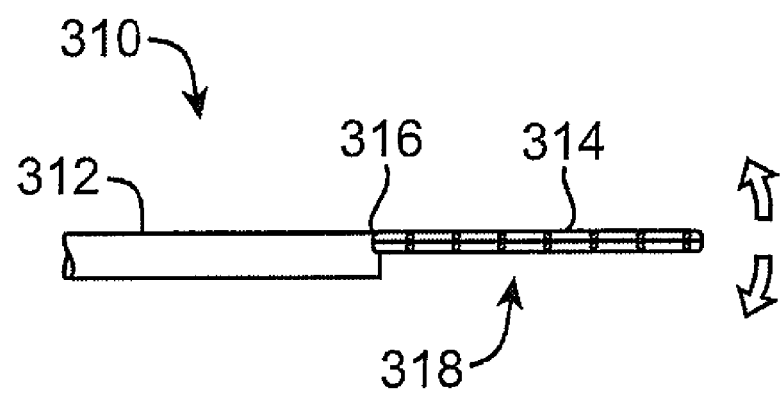
FIGS. 26A and 26B show another variation in which a separate illumination tool having one or more LEDs mounted thereon may be utilized within the imaging hood.
Figure 26B:
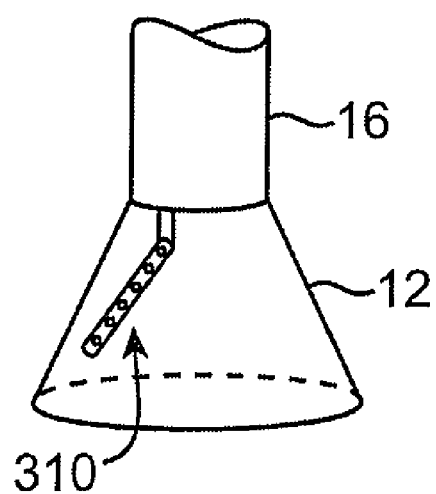

In another alternative for illumination within imaging hood 12, a separate illumination tool 310 may be utilized, as shown in FIG. 26A. An example of such a tool may comprise a flexible intravascular delivery member 312 having a carrier member 314 pivotably connected 316 to a distal end of delivery member 312. One or more LEDs 318 may be mounted along carrier member 314. In use, delivery member 312 may be advanced through deployment catheter 16 until carrier member 314 is positioned within imaging hood 12. Once within imaging hood 12, carrier member 314 may be pivoted in any number of directions to facilitate or optimize the illumination within the imaging hood 12, as shown in FIG. 26B.

In utilizing LEDs for illumination, whether positioned along imaging hood 12 or along a separate instrument, the LEDs may comprise a single LED color, e.g., white light. Alternatively, LEDs of other colors, e.g., red, blue, yellow, etc., may be utilized exclusively or in combination with white LEDs to provide for varied illumination of the tissue or fluids being imaged. Alternatively, sources of infrared or ultraviolet light may be employed to enable imaging beneath the tissue surface or cause fluorescence of tissue for use in system guidance, diagnosis, or therapy.

Figure 27:
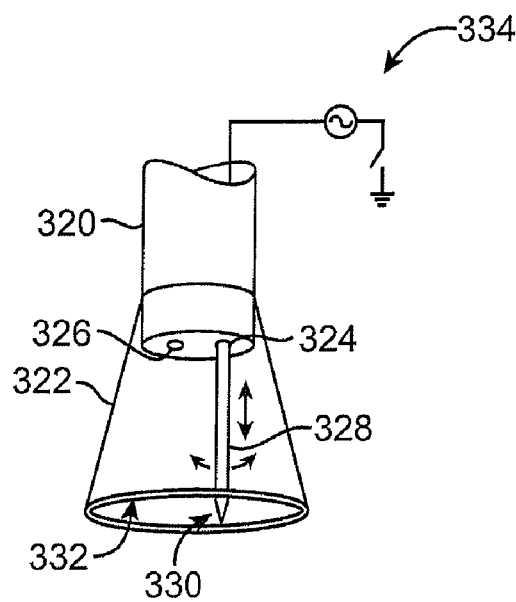
FIG. 27 shows one example of how a therapeutic tool may be advanced through the tissue imager for treating a tissue region of interest.

Aside from providing a visualization platform, the imaging assembly may also be utilized to provide a therapeutic platform for treating tissue being visualized. As shown in FIG. 27, deployment catheter 320 may have imaging hood 322, as described above, and fluid delivery lumen 324 and imaging lumen 326. In this variation, a therapeutic tool such as needle 328 may be delivered through fluid delivery lumen 324 or in another working lumen and advanced through open area 332 for treating the tissue which is visualized. In this instance, needle 328 may define one or several ports 330 for delivering drugs therethrough. Thus, once the appropriate region of tissue has been imaged and located, needle 328 may be advanced and pierced into the underlying tissue where a therapeutic agent may be delivered through ports 330. Alternatively, needle 328 may be in electrical communication with a power source 334, e.g., radio-frequency, microwave, etc., for ablating the underlying tissue area of interest.

Figure 28:
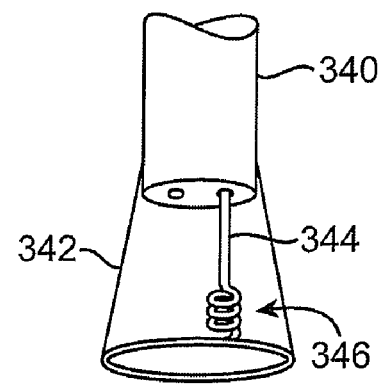
FIG. 28 shows another example of a helical therapeutic tool for treating the tissue region of interest.

FIG. 28 shows another alternative in which deployment catheter 340 may have imaging hood 342 attached thereto, as above, but with a therapeutic tool 344 in the configuration of a helical tissue piercing device 344. Also shown and described above in FIGS. 7A and 7B for use in stabilizing the imaging hood relative to the underlying tissue, the helical tissue piercing device 344 may also be utilized to manipulate the tissue for a variety of therapeutic procedures. The helical portion 346 may also define one or several ports for delivery of therapeutic agents therethrough.

Figure 29:
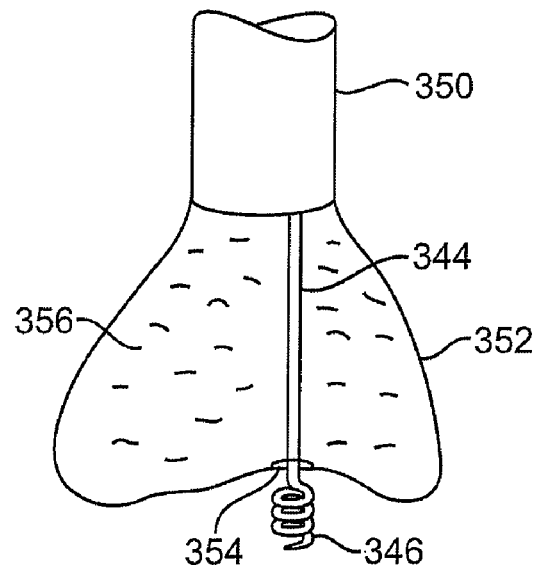
FIG. 29 shows a variation of how a therapeutic tool may be utilized with an expandable imaging balloon.

In yet another alternative, FIG. 29 shows a deployment catheter 350 having an expandable imaging balloon 352 filled with, e.g., saline 356. A therapeutic tool 344, as above, may be translatable relative to balloon 352. To prevent the piercing portion 346 of the tool from tearing balloon 352, a stop 354 may be formed on balloon 352 to prevent the proximal passage of portion 346 past stop 354.

Figure 30B:
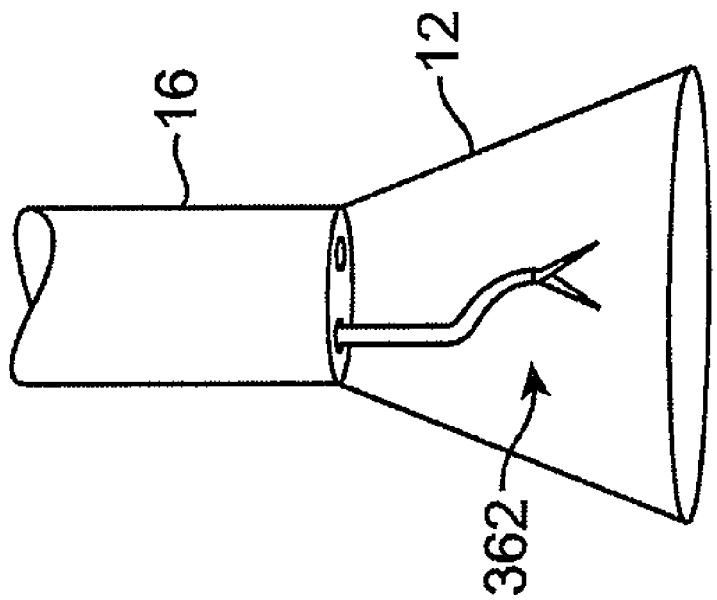
FIGS. 30A and 30B show alternative configurations for therapeutic instruments which may be utilized; one variation is shown having an angled instrument arm and another variation is shown with an off-axis instrument arm.
Figure 30A:
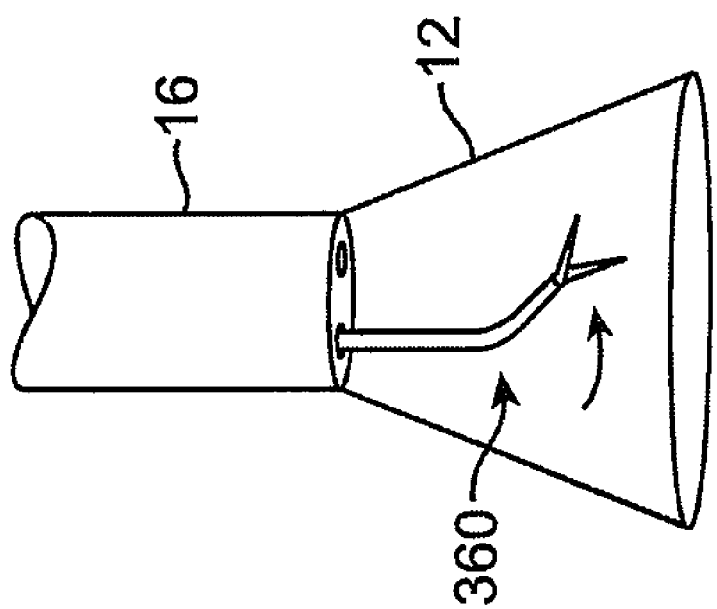

Alternative configurations for tools which may be delivered through deployment catheter 16 for use in tissue manipulation within imaging hood 12 are shown in FIGS. 30A and 30B. FIG. 30A shows one variation of an angled instrument 360, such as a tissue grasper, which may be configured to have an elongate shaft for intravascular delivery through deployment catheter 16 with a distal end which may be angled relative to its elongate shaft upon deployment into imaging hood 12. The elongate shaft may be configured to angle itself automatically, e.g., by the elongate shaft being made at least partially from a shape memory alloy, or upon actuation, e.g., by tensioning a pullwire. FIG. 30B shows another configuration for an instrument 362 being configured to reconfigure its distal portion into an off-axis configuration within imaging hood 12. In either case, the instruments 360, 362 may be reconfigured into a low-profile shape upon withdrawing them proximally back into deployment catheter 16.

Other instruments or tools that may be utilized with the imaging system are shown in the side and end views of FIGS. 31A to 31C. FIG. 31A shows a probe 370 having a distal end effector 372, which may be reconfigured from a low-profile shape to a curved profile. The end effector 372 may be configured as an ablation probe utilizing radio-frequency energy, microwave energy, ultrasound energy, laser energy or even cryo-ablation. Alternatively, the end effector 372 may have several electrodes upon it for detecting or mapping electrical signals transmitted through the underlying tissue.

In the case of an end effector 372 utilized for ablation of the underlying tissue, an additional temperature sensor such as a thermocouple or thermistor 374 positioned upon an elongate member 376 may be advanced into the imaging hood 12 adjacent to the distal end effector 372 for contacting and monitoring a temperature of the ablated tissue. FIG. 31B shows an example in the end view of one configuration for the distal end effector 372 which may be simply angled into a perpendicular configuration for contacting the tissue. FIG. 31C shows another example where the end effector may be reconfigured into a curved end effector 378 for increased tissue contact.

FIGS. 32A and 32B show another variation of an ablation tool utilized with an imaging hood 12 having an enclosed bottom portion. In this variation, an ablation probe, such as a cryo-ablation probe 380 having a distal end effector 382, may be positioned through the imaging hood 12 such that the end effector 382 is placed distally of a transparent membrane or enclosure 384, as shown in the end view of FIG. 32B. The shaft of probe 380 may pass through an opening 386 defined through the membrane 384. In use, the clear fluid may be pumped into imaging hood 12, as described above, and the distal end effector 382 may be placed against a tissue region to be ablated with the imaging hood 12 and the membrane 384 positioned atop or adjacent to the ablated tissue. In the case of cryo-ablation, the imaging fluid may be warmed prior to dispensing into the imaging hood 12 such that the tissue contacted by the membrane 384 may be warmed during the cryo-ablation procedure. In the case of thermal ablation, e.g., utilizing radio-frequency energy, the fluid dispensed into the imaging hood 12 may be cooled such that the tissue contacted by the membrane 384 and adjacent to the ablation probe during the ablation procedure is likewise cooled.

Figure 33A:
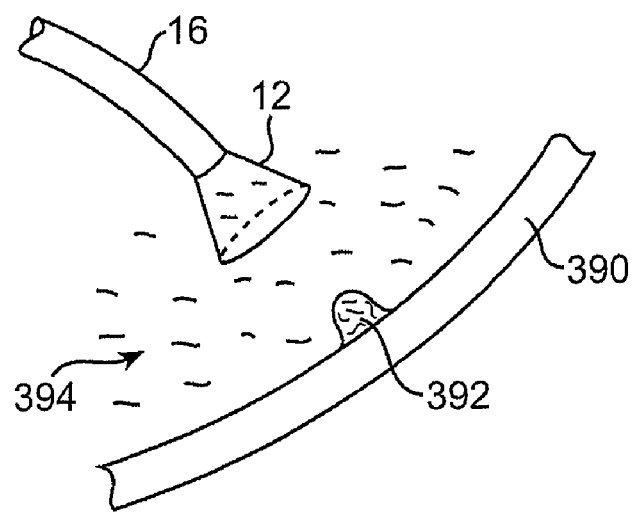
FIGS. 33A and 33B show an example in which the imaging fluid itself may be altered in temperature to facilitate various procedures upon the underlying tissue.
Figure 33B:
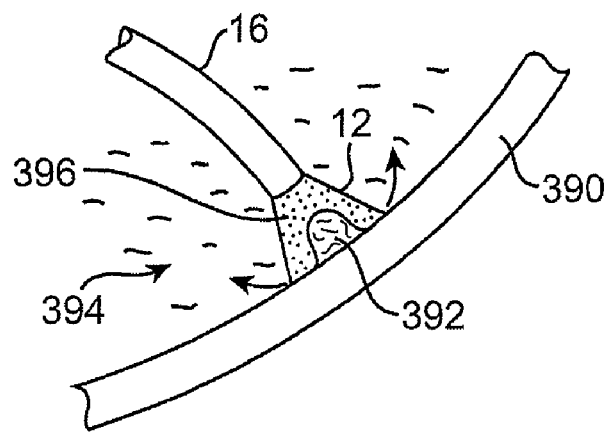

In either example described above, the imaging fluid may be varied in its temperature to facilitate various procedures to be performed upon the tissue. In other cases, the imaging fluid itself may be altered to facilitate various procedures. For instance as shown in FIG. 33A, a deployment catheter 16 and imaging hood 12 may be advanced within a hollow body organ, such as a bladder filled with urine 394, towards a lesion or tumor 392 on the bladder wall. The imaging hood 12 may be placed entirely over the lesion 392, or over a portion of the lesion. Once secured against the tissue wall 390, a cryo-fluid, i.e., a fluid which has been cooled to below freezing temperatures of, e.g., water or blood, may be pumped into the imaging hood 12 to cryo-ablate the lesion 390, as shown in FIG. 33B while avoiding the creation of ice on the instrument or surface of tissue.

As the cryo-fluid leaks out of the imaging hood 12 and into the organ, the fluid may be warmed naturally by the patient body and ultimately removed. The cryo-fluid may be a colorless and translucent fluid which enables visualization therethrough of the underlying tissue. An example of such a fluid is Fluorinert™ (3M, St. Paul, Minn.), which is a colorless and odorless perfluorinated liquid. The use of a liquid such as Fluorinert™ enables the cryo-ablation procedure without the formation of ice within or outside of the imaging hood 12. Alternatively, rather than utilizing cryo-ablation, hyperthermic treatments may also be effected by heating the Fluorinert™ liquid to elevated temperatures for ablating the lesion 392 within the imaging hood 12. Moreover, Fluorinert™ may be utilized in various other parts of the body, such as within the heart.

Figure 33C:
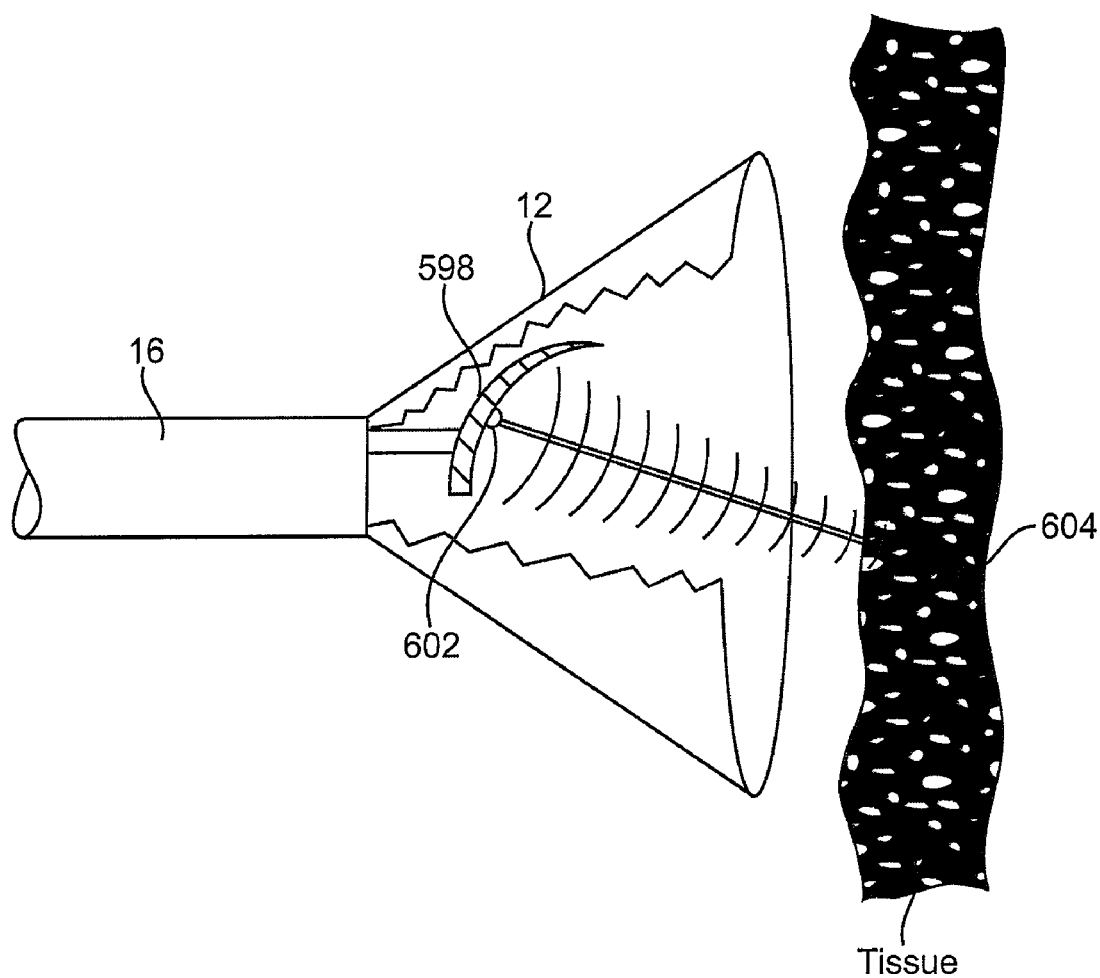
FIG. 33C illustrates a variation of a system using ultrasound to treat the tissue under the hood.

FIG. 33C illustrates another variation of a system according to the present invention. In this variation, an unltrasound beam 598 (for example, high frequency ultrasound, commonly referred to as HIFU) transducer 600 is integrated into the hood 12 and/or catheter 16. The beam 598 focuses on a region of interest in the tissue. This allows cauterization or welding of tissue via the ultrasound beam. The clear solution assists the operator in focusing the beam 598 accurately on the target tissue surface. Optionally, a laser pointer, LED or other pointing device/indicator 602 that coincides with the focal point 604 of the beam 598 can be used as a guide to ensure accurate placement of the beam 598 on the tissue surface.

One possible application for this variation is treatment of the PFO where the septum secundum is welded on to the septum primum to achieve closure. Alternatively, by just injuring the septum secundum with HIFU, the healing process can take over to close the tissue onto the septum primum.

Figure 34A:
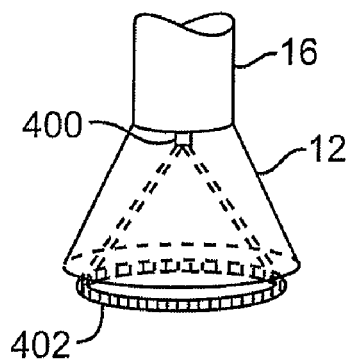
FIGS. 34A and 34B show an example of a laser ring generator which may be utilized with the imaging system and an example for applying the laser ring generator within the left atrium of a heart for treating atrial fibrillation.

FIG. 34A shows another variation of an instrument which may be utilized with the imaging system. In this variation, a laser ring generator 400 may be passed through the deployment catheter 16 and partially into imaging hood 12. A laser ring generator 400 is typically used to create a circular ring of laser energy 402 for generating a conduction block around the pulmonary veins typically in the treatment of atrial fibrillation. The circular ring of laser energy 402 may be generated such that a diameter of the ring 402 is contained within a diameter of the imaging hood 12 to allow for tissue ablation directly upon tissue being imaged. Signals which cause atrial fibrillation typically come from the entry area of the pulmonary veins into the left atrium and treatments may sometimes include delivering ablation energy to the ostia of the pulmonary veins within the atrium. The ablated areas of the tissue may produce a circular scar which blocks the impulses for atrial fibrillation.

When using the laser energy to ablate the tissue of the heart, it may be generally desirable to maintain the integrity and health of the tissue overlying the surface while ablating the underlying tissue. This may be accomplished, for example, by cooling the imaging fluid to a temperature below the body temperature of the patient but which is above the freezing point of blood (e.g., 2° C. to 35° C.). The cooled imaging fluid may thus maintain the surface tissue at the cooled fluid temperature while the deeper underlying tissue remains at the patient body temperature. When the laser energy (or other types of energy such as radio frequency energy, microwave energy, ultrasound energy, etc.) irradiates the tissue, both the cooled tissue surface as well as the deeper underlying tissue will rise in temperature uniformly. The deeper underlying tissue, which was maintained at the body temperature, will increase to temperatures which are sufficiently high to destroy the underlying tissue. Meanwhile, the temperature of the cooled surface tissue will also rise but only to temperatures that are near body temperature or slightly above.

Figure 34B:
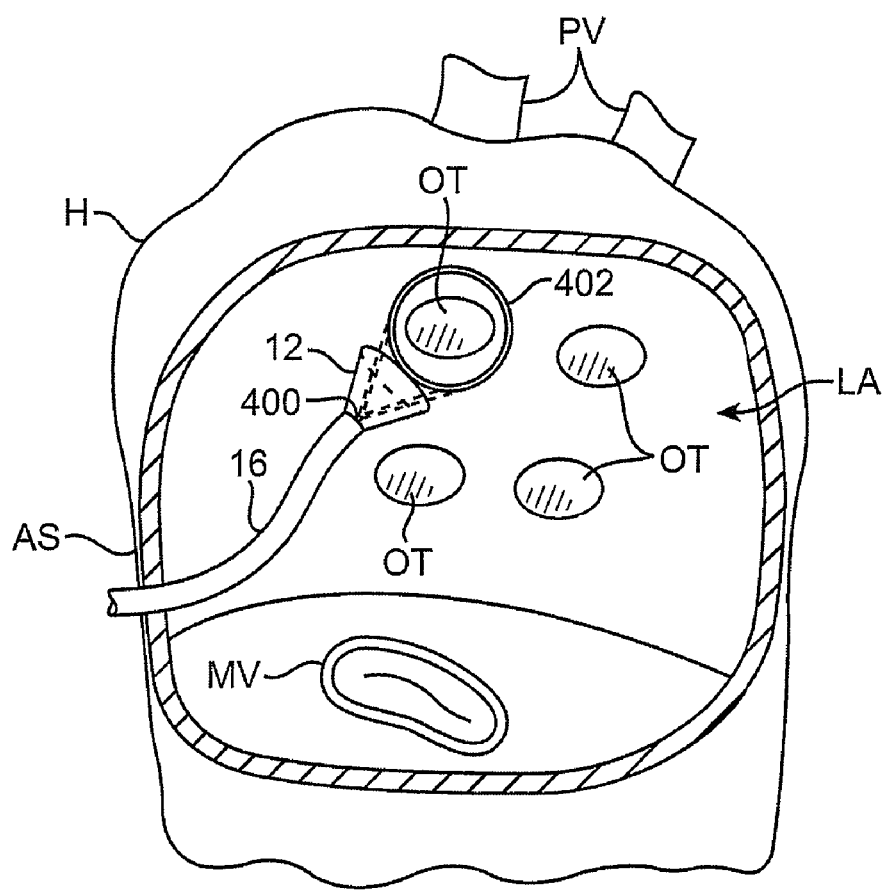

Accordingly, as shown in FIG. 34B, one example for treatment may include passing deployment catheter 16 across the atrial septum AS and into the left atrium LA of the patient's heart H. Other methods of accessing the left atrium LA may also be utilized. The imaging hood 12 and laser ring generator 400 may be positioned adjacent to or over one or more of the ostium OT of the pulmonary veins PV and the laser generator 400 may ablate the tissue around the ostium OT with the circular ring of laser energy 402 to create a conduction block. Once one or more of the tissue around the ostium OT have been ablated, the imaging hood 12 may be reconfigured into a low profile for removal from the patient heart H.

Figure 34C:
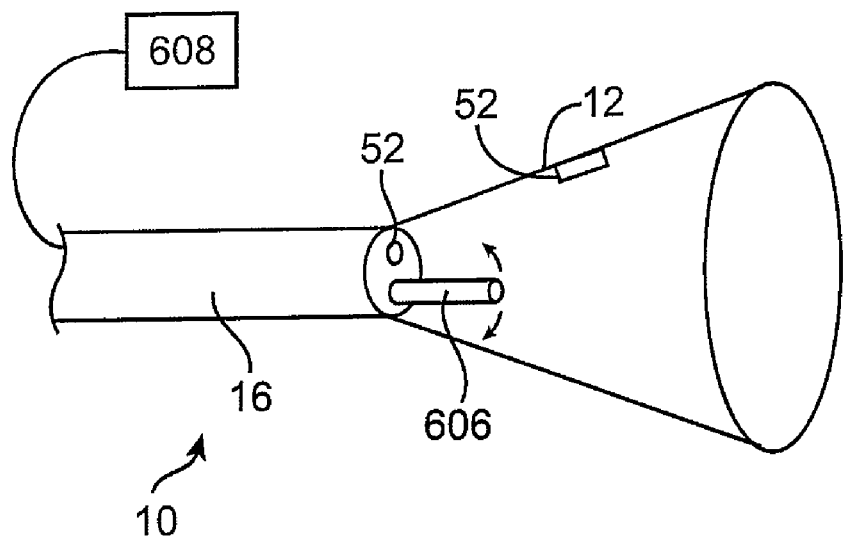
FIG. 34C illustrates a variation of the system having a visualization element located at the end of the catheter and/or on the hood.

FIG. 34C also illustrates a variation of the system 10 having a visualization element 52 located at the end of the catheter 16 and/or on the hood 12. The device 10 also includes a fiber 606 coupled to a laser source 608. The fiber 606 is optionally moveable so that the laser beam may be focused on desired areas to treat tissue (e.g., the injury of the tissue leads to healing over time). The fiber 606 can direct the laser energy invarious patterns (e.g., spot treatment, rings, various geometries, etc.). The laser may be collimated or non-collimated (where a collimated laser beam will propagate with the lowest possible beam divergence for a given beam size).

Figure 34D:
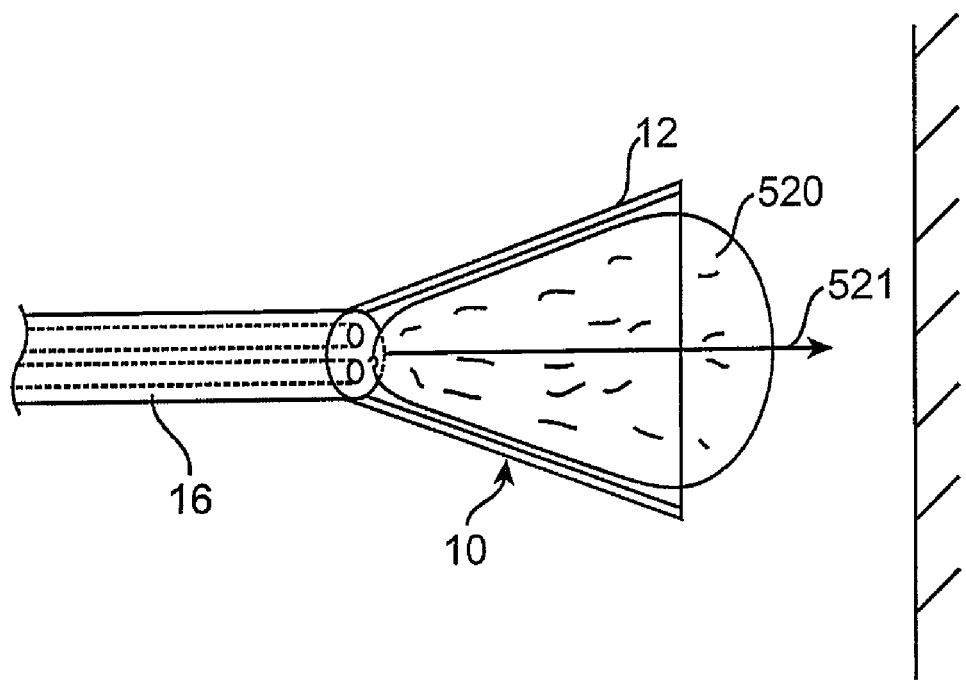
FIG. 34D illustrates another variation of a system according to the present invention using an inflatable member for advancing the device to a site.

FIG. 34D illustrates another variation of a system according to the present invention. In this variation, an inflatable member 520 the hood 12 to be expanded so that the device 10 may be advanced and pushed against tissue. This variation prevents the excessive use of saline or other fluid when the hood is not properly or partially sealed against a tissue surface. The inflatable member 520 may be fabricated to permit energy (e.g., such as laser or ultrasound as shown by line 521)

to be transmitted therethrough. For example, the inflatable member may be fabricated from silicone and a low thermal conductivity liquid is used to inflate the member 520.

One of the difficulties in treating tissue in or around the ostium OT is the dynamic fluid flow of blood through the ostium OT. The dynamic forces make cannulation or entry of the ostium OT difficult. Thus, another variation on instruments or tools utilizable with the imaging system is an extendible cannula 410 having a cannula lumen 412 defined therethrough, as shown in FIG. 35A. The extendible cannula 410 may generally comprise an elongate tubular member which may be positioned within the deployment catheter 16 during delivery and then projected distally through the imaging hood 12 and optionally beyond, as shown in FIG. 35B.

In use, once the imaging hood 12 has been desirably positioned relative to the tissue, e.g., as shown in FIG. 35C outside the ostium OT of a pulmonary vein PV, the extendible cannula 410 may be projected distally from the deployment catheter 16 while optionally imaging the tissue through the imaging hood 12, as described above. The extendible cannula 410 may be projected distally until its distal end is extended at least partially into the ostium OT. Once in the ostium OT, an instrument or energy ablation device may be extended through and out of the cannula lumen 412 for treatment within the ostium OT. Upon completion of the procedure, the cannula 410 may be withdrawn proximally and removed from the patient body. The extendible cannula 410 may also include an inflatable occlusion balloon at or near its distal end to block the blood flow out of the PV to maintain a clear view of the tissue region. Alternatively, the extendible cannula 410 may define a lumen therethrough beyond the occlusion balloon to bypass at least a portion of the blood that normally exits the pulmonary vein PV by directing the blood through the cannula 410 to exit proximal of the imaging hood.

Figure 36A:
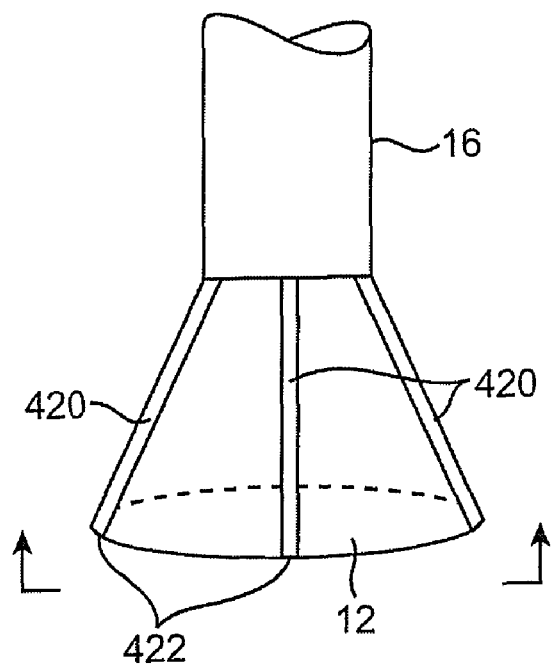
FIGS. 36A and 36B show side and end views, respectively, of an imaging hood having one or more tubular support members integrated with the hood for passing instruments or tools therethrough for treatment upon the underlying tissue.
Figure 36B:
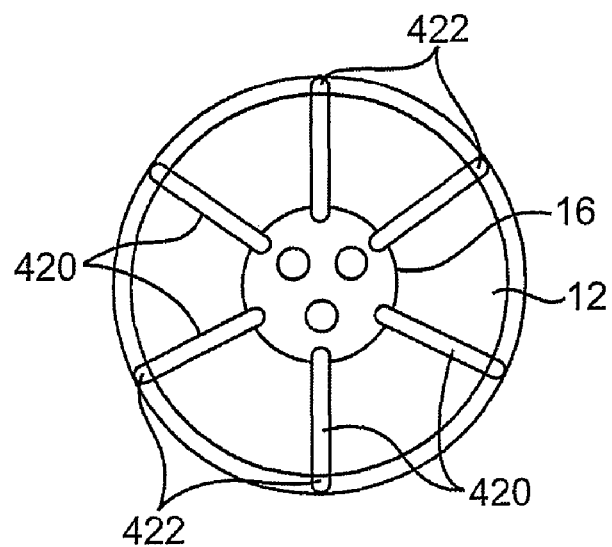

Yet another variation for tool or instrument use may be seen in the side and end views of FIGS. 36A and 36B. In this variation, imaging hood 12 may have one or more tubular support members 420 integrated with the hood 12. Each of the tubular support members 420 may define an access lumen 422 through which one or more instruments or tools may be delivered for treatment upon the underlying tissue. One particular example is shown and described above for FIG. 7C.

Figure 37A:
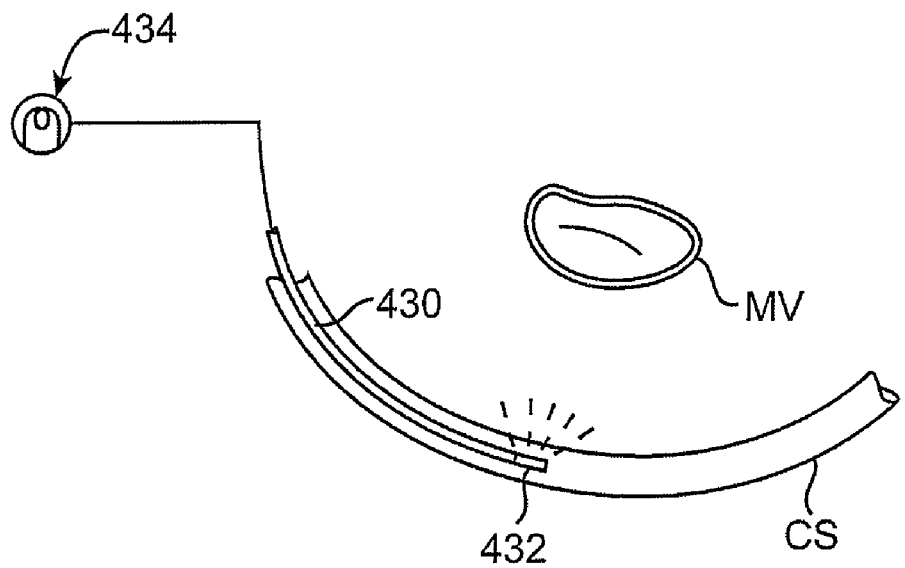
FIGS. 37A and 37B illustrate how an imaging device may be guided within a heart chamber to a region of interest utilizing a lighted probe positioned temporarily within, e.g., a lumen of the coronary sinus.
Figure 37B:
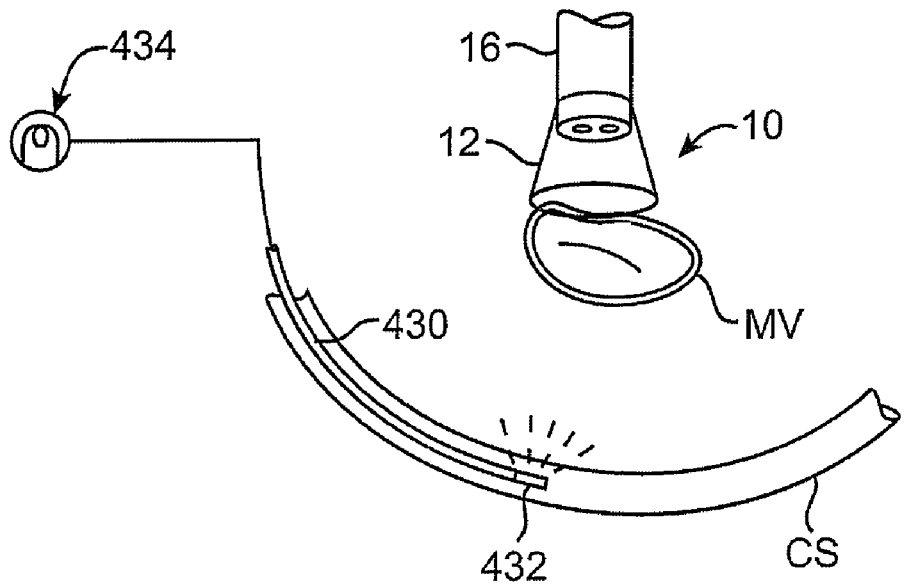

Various methods and instruments may be utilized for using or facilitating the use of the system. For instance, one method may include facilitating the initial delivery and placement of a device into the patient's heart. In initially guiding the imaging assembly within the heart chamber to, e.g., the mitral valve MV, a separate guiding probe 430 may be utilized, as shown in FIGS. 37A and 37B. Guiding probe 430 may, for example, comprise an optical fiber through which a light source 434 may be used to illuminate a distal tip portion 432. The tip portion 432 may be advanced into the heart through, e.g., the coronary sinus CS, until the tip is positioned adjacent to the mitral valve MV. The tip 432 may be illuminated, as shown in FIG. 37A, and imaging assembly 10 may then be guided towards the illuminated tip 432, which is visible from within the atrial chamber, towards mitral valve UV.

Figure 38A:
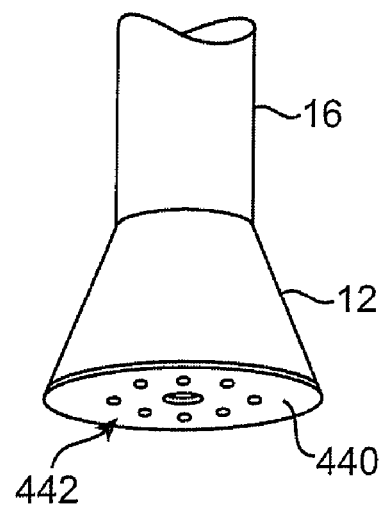
FIGS. 38A and 38B show an imaging hood having a removable disk-shaped member for implantation upon the tissue surface.
Figure 38B:
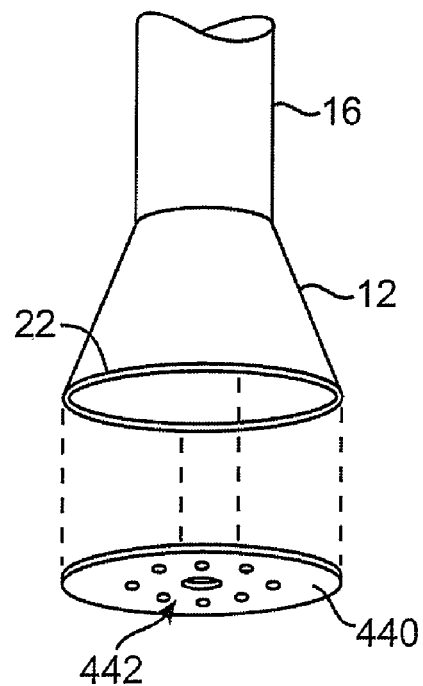

Aside from the devices and methods described above, the imaging system may be utilized to facilitate various other procedures. Turning now to FIGS. 38A and 38B, the imaging hood of the device in particular may be utilized. In this example, a collapsible membrane or disk-shaped member 440 may be temporarily secured around the contact edge or lip of imaging hood 12. During intravascular delivery, the imaging hood 12 and the attached member 440 may both be in a collapsed configuration to maintain a low profile for delivery. Upon deployment, both the imaging hood 12 and the member 440 may extend into their expanded configurations.

The disk-shaped member 440 may be comprised of a variety of materials depending upon the application. For instance, member 440 may be fabricated from a porous polymeric material infused with a drug eluting medicament 442 for implantation against a tissue surface for slow infusion of the medicament into the underlying tissue. Alternatively, the member 440 may be fabricated from a non-porous material, e.g., metal or polymer, for implantation and closure of a wound or over a cavity to prevent fluid leakage. In yet another alternative, the member 440 may be made from a distensible material which is secured to imaging hood 12 in an expanded condition. Once implanted or secured on a tissue surface or wound, the expanded member 440 may be released from imaging hood 12. Upon release, the expanded member 440 may shrink to a smaller size while approximating the attached underlying tissue, e.g., to close a wound or opening.

One method for securing the disk-shaped member 440 to a tissue surface may include a plurality of tissue anchors 444, e.g., barbs, hooks, projections, etc., which are attached to a surface of the member 440. Other methods of attachments may include adhesives, suturing, etc. In use, as shown in FIGS. 39A to 39C, the imaging hood 12 may be deployed in its expanded configuration with member 440 attached thereto with the plurality of tissue anchors 444 projecting distally. The tissue anchors 444 may be urged into a tissue region to be treated 446, as seen in FIG. 39A, until the anchors 444 are secured in the tissue and member 440 is positioned directly against the tissue, as shown in FIG. 39B. A pullwire may be actuated to release the member 440 from the imaging hood 12 and deployment catheter 16 may be withdrawn proximally to leave member 440 secured against the tissue 446.

Figure 40A:
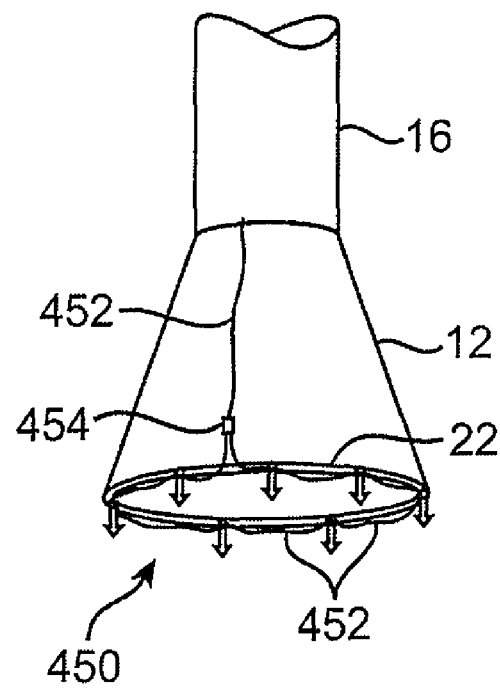
FIGS. 40A and 40B illustrate an imaging hood having a deployable anchor assembly attached to the tissue contact edge and an assembly view of the anchors and the suture or wire connected to the anchors, respectively
Figure 40B:
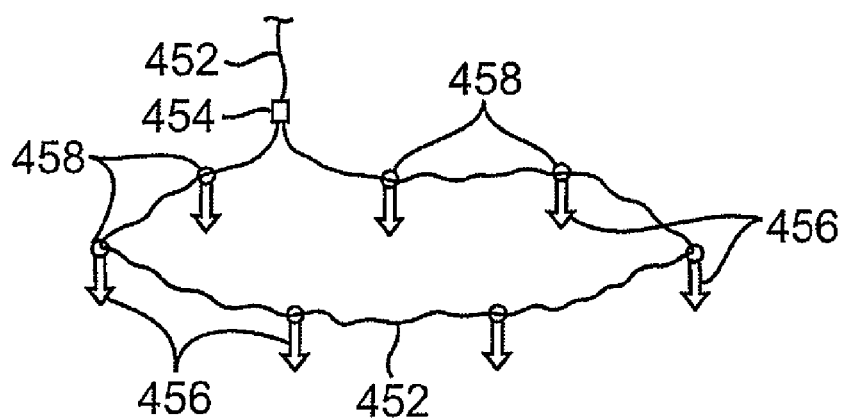

Another variation for tissue manipulation and treatment may be seen in the variation of FIG. 40A, which illustrates an imaging hood 12 having a deployable anchor assembly 450 attached to the tissue contact edge 22. FIG. 40B illustrates the anchor assembly 450 detached from the imaging hood 12 for clarity. The anchor assembly 450 may be seen as having a plurality of discrete tissue anchors 456, e.g., barbs, hooks, projections, etc., each having a suture retaining end, e.g., an eyelet or opening 458 in a proximal end of the anchors 456. A suture member or wire 452 may be slidingly connected to each anchor 456 through the openings 458 and through a cinching element 454, which may be configured to slide uni-directionally over the suture or wire 452 to approximate each of the anchors 456 towards one another. Each of the anchors 456 may be temporarily attached to the imaging hood 12 through a variety of methods. For instance, a pullwire or retaining wire may hold each of the anchors within a receiving ring around the circumference of the imaging hood 12. When the anchors 456 are released, the pullwire or retaining wire may be tensioned from its proximal end outside the patient body to thereby free the anchors 456 from the imaging hood 12.

One example for use of the anchor assembly 450 is shown in FIGS. 41A to 41D for closure of an opening or wound 460, e.g., patent foramen ovate (PFO). The deployment catheter 16 and imaging hood 12 may be delivered intravascularly into, e.g., a patient heart. As the imaging hood 12 is deployed into its expanded configuration, the imaging hood 12 may be positioned adjacent to the opening or wound 460, as shown in FIG. 41A. With the anchor assembly 450 positioned upon the expanded imaging hood 12, deployment catheter 16 may be directed to urge the contact edge of imaging hood 12 and anchor assembly 450 into the region surrounding the tissue opening 460, as shown in FIG. 41B. Once the anchor assembly 450 has been secured within the surrounding tissue, the anchors may be released from imaging hood 12 leaving the anchor assembly 450 and suture member 452 trailing from the anchors, as shown in FIG. 41C. The suture or wire member 452 may be tightened by pulling it proximally from outside the patient body to approximate the anchors of anchor assembly 450 towards one another in a purse-string manner to close the tissue opening 462, as shown in FIG. 41D. The cinching element 454 may also be pushed distally over the suture or wire member 452 to prevent the approximated anchor assembly 450 from loosening or widening.

Figure 41E:
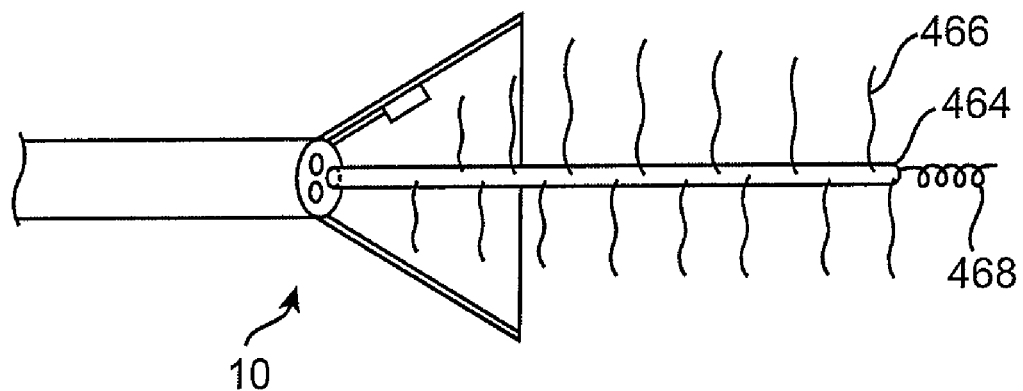
FIGS. 41E-41F illustrates tissue imaging and manipulation assemblies configured to deliver implants.

FIG. 41E illustrates a tissue imaging and manipulation assembly 10 configured to deliver an implant 464. In this variation, the implant comprises a shaft having a plurality of thrombogenic fibers 466. The implant 464 further includes a tissue attachment member 468. In use, the assembly 10 delivers the implant 464 to a tissue area or cavity. The implant may be rotated into tissue (or otherwise attached) using the attachment member 468. The implant 464 may be combined with other procedures discussed herein, especially where occlusion of a cavity or opening is required.

Figure 41F:
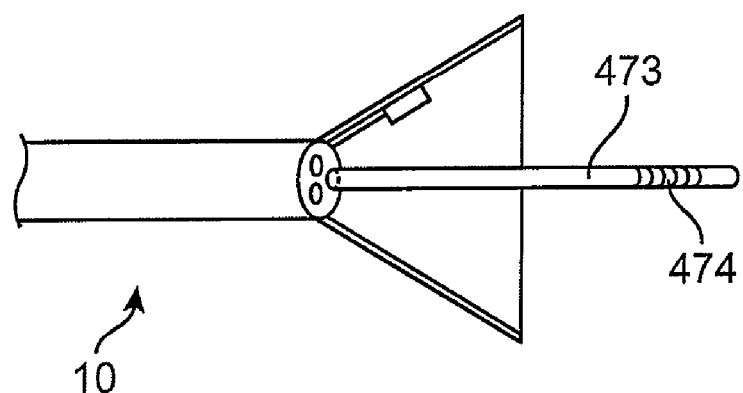

FIG. 41F illustrates another variation of an assembly 10 according to the present invention. In this case, the implant 474 may comprise a stent, coil, patch, suture, or other such implant. The implant 474 may be delivered using a delivery catheter 473 or similar means.

Figure 42:
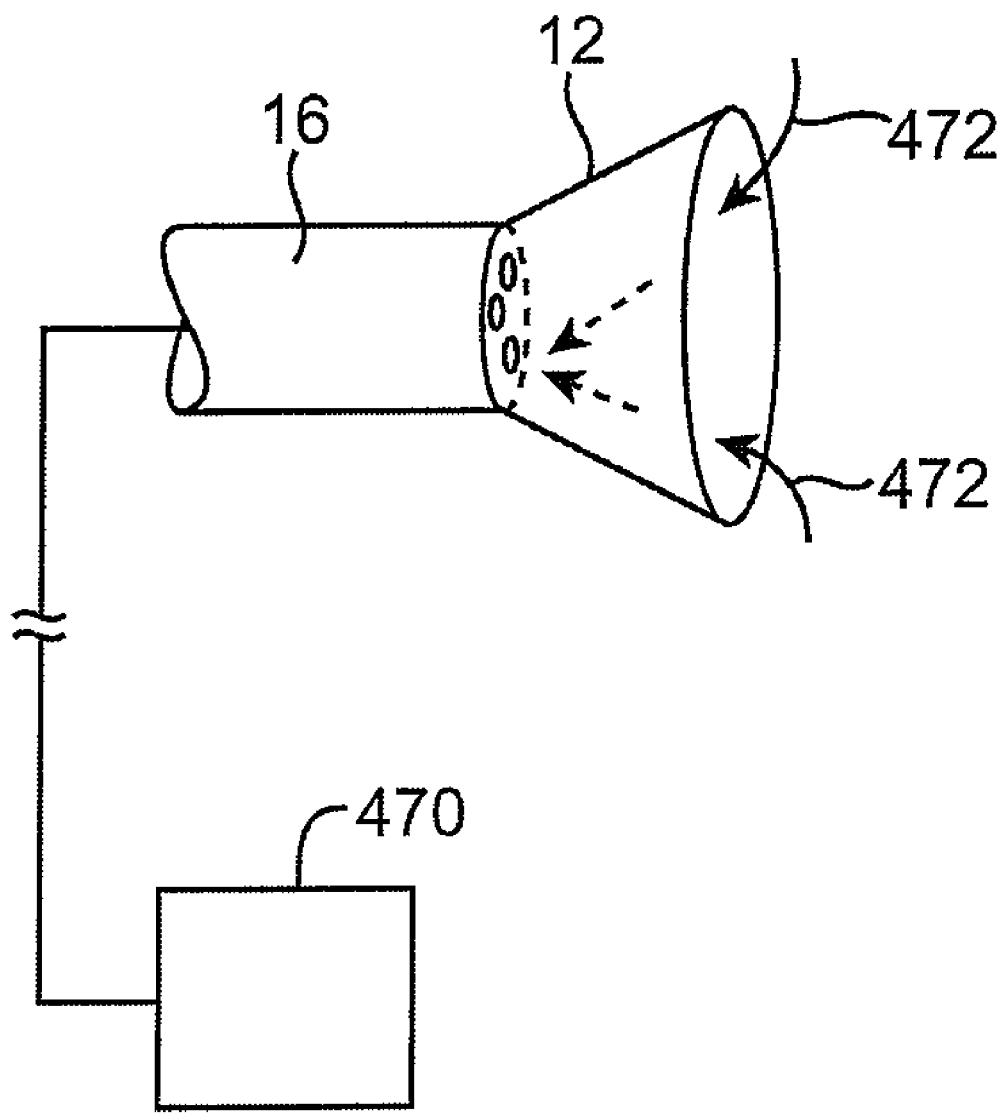
FIG. 42 shows another variation in which the imaging system may be fluidly coupled to a dialysis unit for filtering a patient's blood.

Another example for an alternative use is shown in FIG. 42, where the deployment catheter 16 and deployed imaging hood 12 may be positioned within a patient body for drawing blood 472 into deployment catheter 16. The drawn blood 472 may be pumped through a dialysis unit 470 located externally of the patient body for filtering the drawn blood 472 and the filtered blood may be reintroduced back into the patient.

Figure 43A:
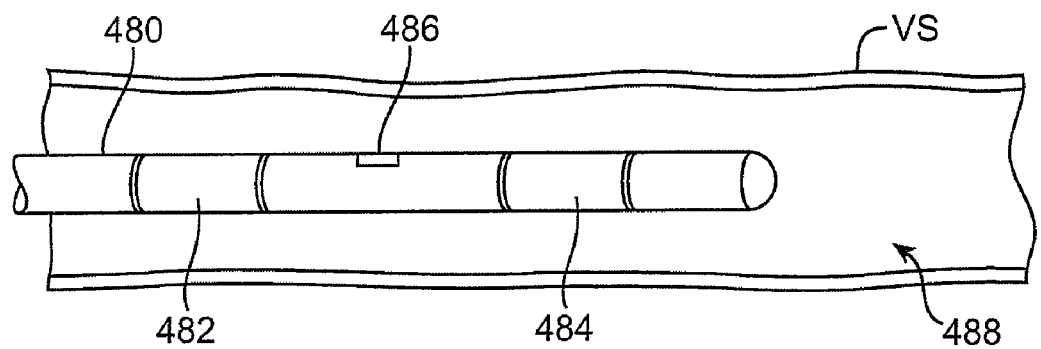
FIGS. 43A and 43B show a variation of the deployment catheter having a first deployable hood and a second deployable hood positioned distal to the first hood; the deployment catheter may also have a side-viewing imaging element positioned between the first and second hoods for imaging tissue between the expanded hoods.
Figure 43B:
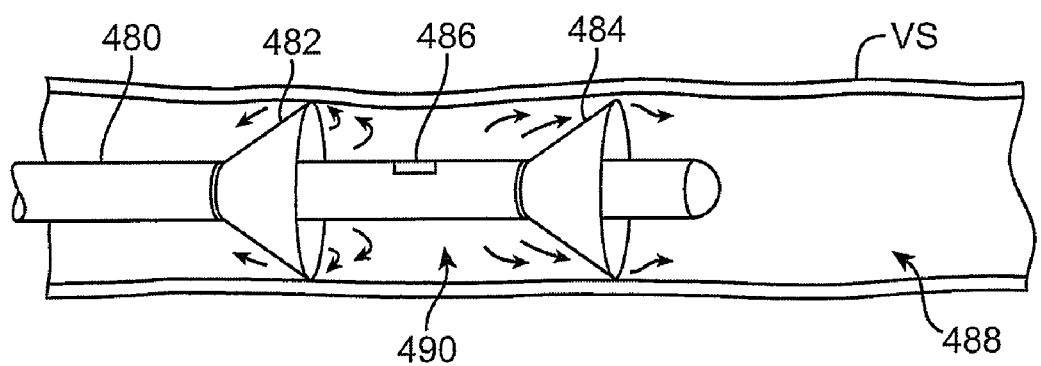

Yet another variation is shown in FIGS. 43A and 43B, which show a variation of the deployment catheter 480 having a first deployable hood 482 and a second deployable hood 484 positioned distal to the first hood 482. The deployment catheter 480 may also have a side-viewing imaging element 486 positioned between the first and second hoods 482, 484 along the length of the deployment catheter 480. In use, such a device may be introduced through a lumen 488 of a vessel VS, where one or both hoods 482, 484 may be expanded to gently contact the surrounding walls of vessel VS. Once hoods 482, 484 have been expanded, the clear imaging fluid may be pumped in the space defined between the hoods 482, 484 to displace any blood and to create an imaging space 490, as shown in FIG. 43B. With the clear fluid in-between hoods 482, 484, the imaging element 486 may be used to view the surrounding tissue surface contained between hoods 482, 484. Other instruments or tools may be passed through deployment catheter 480 and through one or more openings defined along the catheter 480 for additionally performing therapeutic procedures upon the vessel wall.

Figure 43C:
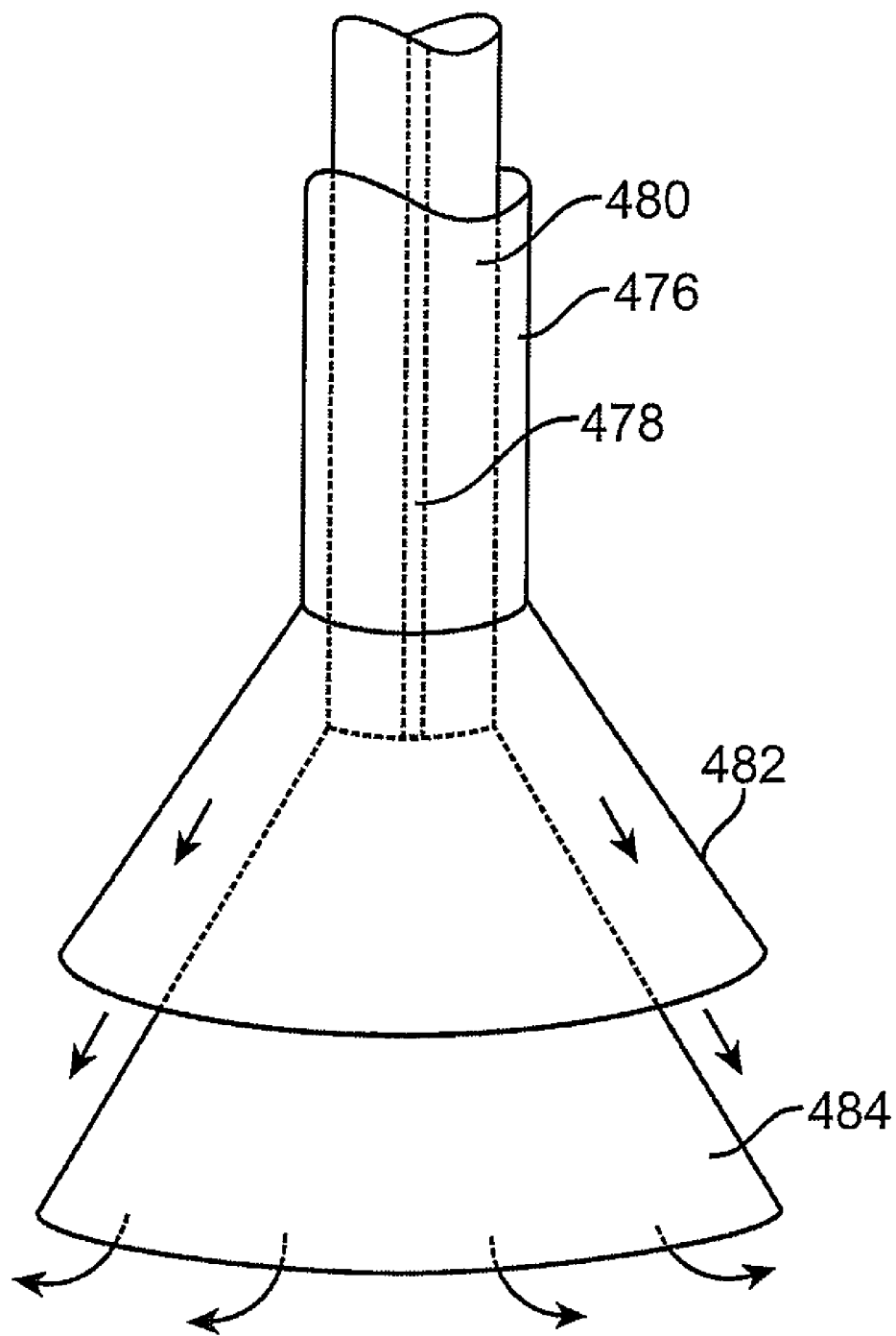
FIG. 43C illustrates another variation of a deployment catheter 480 having a series of deployable hoods arranged to produce a clear visual field.

FIG. 43C illustrates another variation of a deployment catheter 480 having a series of deployable hoods 482, 484 spaced close together. The deployment catheter 480 will include at least two fluid supply lumens 476, 478, where each lumen is fluidly coupled to an open area within the outer 482 and inner 484 hoods. During use, the fluid running between the outer and inner hoods 482, 484 clears the blood, debris or other obstructions from around the inside hood 484. One benefit is that this allows the device to have better visualization within the inner hood 484 by preventing bodily fluids from entering the open area. This is especially useful when the inner hood 484 abuts tissue and fluid from the outer hood 482 creates a flow pattern that opposes bodily fluids from entering the open area of the inner hood 484.

Visualization elements may be placed within one or both hoods. In one variation of the device, the inner hood 484 may be fabricated from a clear material so that one or more visualization elements may be placed within the outer hood 482. Alternatively, or in combination, the visualization elements may be placed to visualize the open area of the inner hood 484. It should be noted that any number of hoods may be used.

Figure 44A:
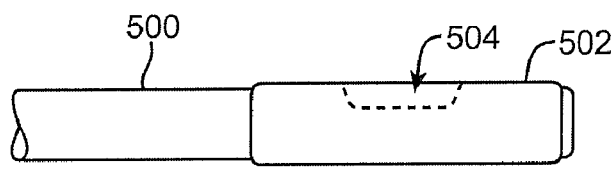
FIGS. 44A and 44B show side and end views, respectively, of a deployment catheter having a side-imaging balloon in an un-inflated low-profile configuration.
Figure 44B:
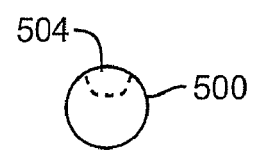
Figure 45A:
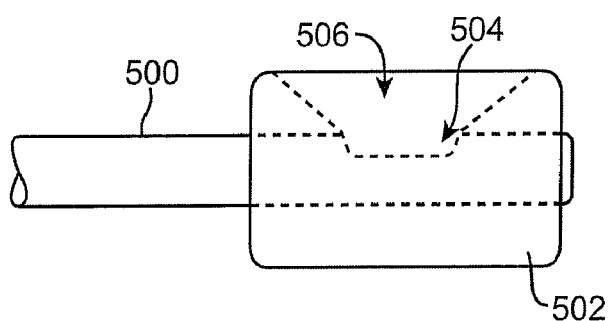
FIGS. 45A to 45C show side, top, and end views, respectively, of the inflated balloon of FIGS. 44A and 44B defining a visualization field in the inflated balloon.
Figure 45C:
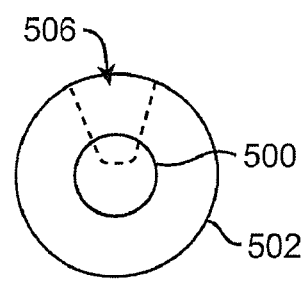
Figure 45B:
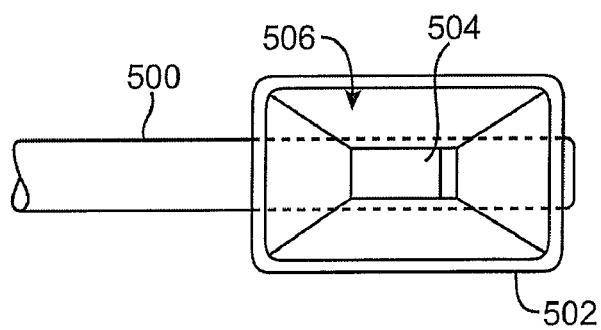

Another variation of a deployment catheter 500 which may be used for imaging tissue to the side of the instrument may be seen in FIGS. 44A to 45B. FIGS. 44A and 44B show side and end views of deployment catheter 500 having a side-imaging balloon 502 in an un-inflated low-profile configuration. A side-imaging element 504 may be positioned within a distal portion of the catheter 500 where the balloon 502 is disposed. When balloon 502 is inflated, it may expand radially to contact the surrounding tissue, but where the imaging element 504 is located, a visualization field 506 may be created by the balloon 502, as shown in the side, top, and end views of FIGS. 45A to 45B, respectively. The visualization field 506 may simply be a cavity or channel which is defined within the inflated balloon 502 such that the visualization element 504 is provided an image of the area within field 506 which is clear and unobstructed by balloon 502.

Figure 46B:
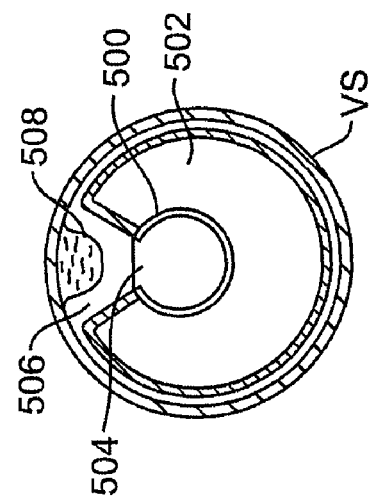
FIGS. 46A and 46B show side and cross-sectional end views, respectively, for one method of use in visualizing a lesion upon a vessel wall within the visualization field of the inflated balloon from FIGS. 45A to 45C.
Figure 46A:
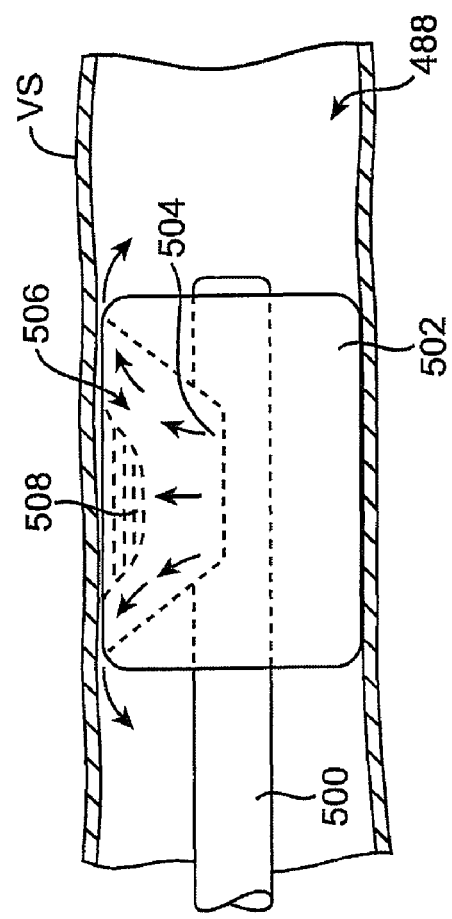

In use, deployment catheter 500 may be advanced intravascularly through vessel lumen 488 towards a lesion or tumor 508 to be visualized and/or treated. Upon reaching the lesion 508, deployment catheter 500 may be positioned adjacently to the lesion 508 and balloon 502 may be inflated such that the lesion 508 is contained within the visualization field 506. Once balloon 502 is fully inflated and in contact against the vessel wall, clear fluid may be pumped into visualization field 506 through deployment catheter 500 to displace any blood or opaque fluids from the field 506, as shown in the side and end views of FIGS. 46A and 46B, respectively. The lesion 508 may then be visually inspected and treated by passing any number of instruments through deployment catheter 500 and into field 506.

Figure 47A:
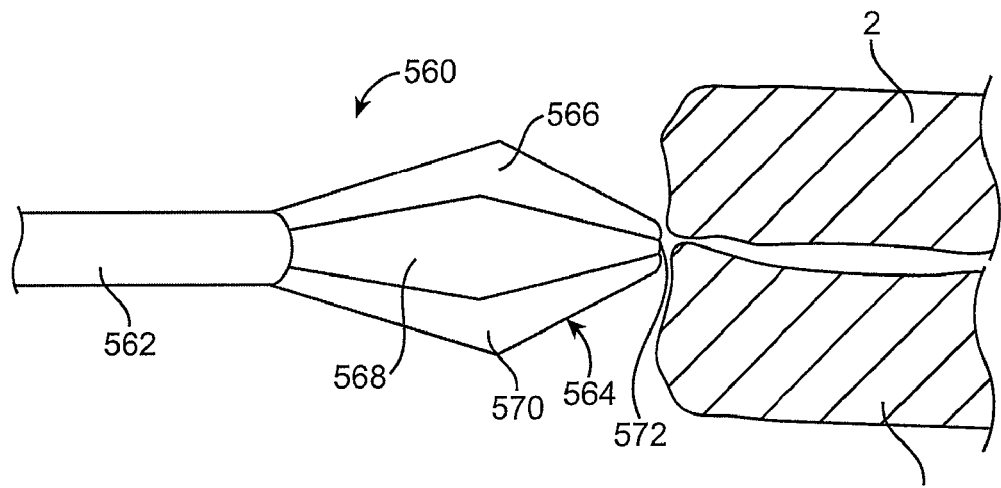
FIGS. 47A-47B illustrate a variation of a device according to the present invention where components of the system allow for blunt dissection of tissue.
Figure 47B:
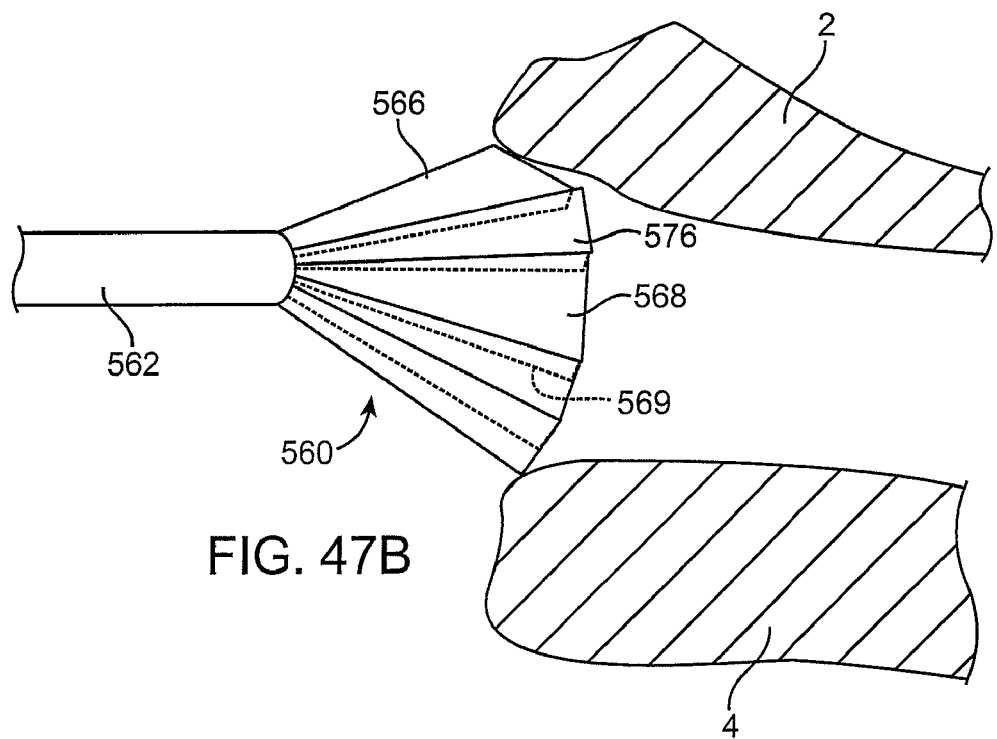

FIGS. 47A-47B illustrate a variation of a device according to the present invention where components of the system 560 allow for dissection/blunt dissection of tissue. As shown, a hood 564 extends from a catheter 562, where the hood 564 comprises a plurality of rigid sections 566 or leaflets. The leaflets 566, 568, 570 may be fabricated from a stiff metal or polymer. Moreover, a variation of the device may include leaflets 566, 568, 570 having alternating constructions (e.g., a flexible leaflet interspaced between stiff leaflets, a soft leaflet interspaced between stiff or hard leaflets, etc.) Although the leaflets are illustrated as having tapered profiles towards a tip 572 of the device 560, the tip 572 of the device may be sufficiently blunted so as to avoid unnecessary trauma to the tissue.

FIG. 47A illustrates the device 560 as it approaches adjacent layers of tissue 2, 4. As illustrated in FIG. 47B, once appropriately positioned, the device 560 dissects tissue by opening or repeatedly opening and closing to separate the layers of tissue 2, 4. FIG. 47B also illustrates the dissector hood 564 as having a flexible material or webbing 576 located between adjacent leaflets 566, 568, 570. This flexible material/webbing 576 permits the hood to form a seal once the hood is placed adjacent to a tissue surface. As illustrated, the leaflets 566, 568, 570 may overlap (as shown by the overlapping portion 569).

Figure 48A:
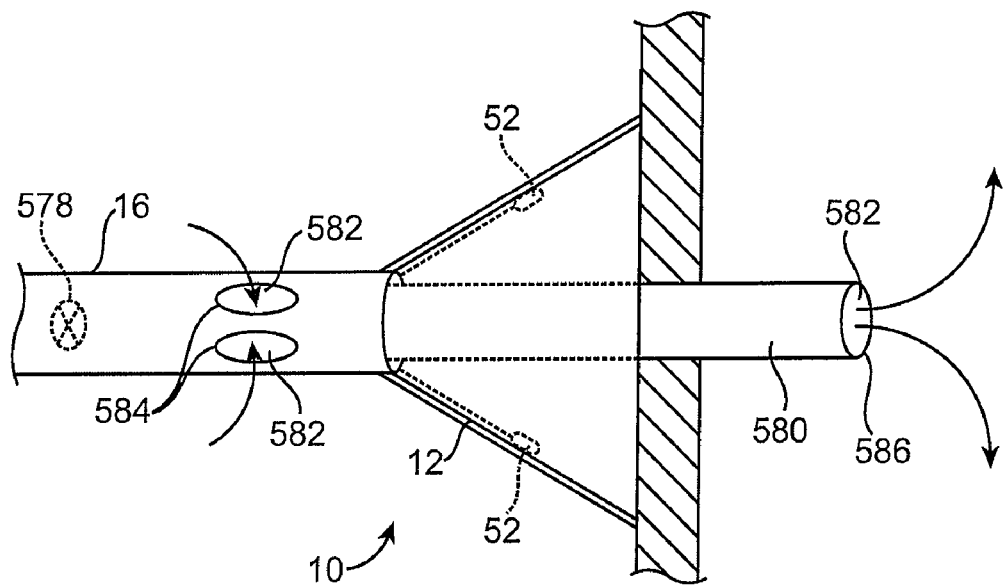
FIG. 48A show a variation of a tissue imaging and manipulation assembly including an elongate bypass portion.

FIG. 48A illustrates a variation of a tissue imaging and manipulation assembly 10 further including an elongate bypass portion 580. The elongate bypass portion 580 includes at least one bypass lumen 582 that allows a fluid path between proximal opening 584 in the catheter 16 and a distal opening 586 located distally of the hood 16. The bypass lumen 582 allows fluid to pass around the open area during a surgical procedure. Furthermore, the hood 12 may include one or more visualization element 52 to allow visualization of the open area. A variation of the assembly 10 may include a pump-type device 578 to assist in moving fluid through the assembly 10.

The elongate bypass portion 580 may be moveable relative to the hood 12 or catheter 16. In addition, the elongate bypass portion 580 may include one or more structures to facilitate various procedures. For example, FIG. 48B illustrates a variation of the system 10 of FIG. 48A with the addition of a support flap 588. The support flap 588 is preferably fabricated from a material that allows the flap 588 to assume a reduced profile for delivery. Upon expansion, the flap 588 provides a semi-rigid support when placed against tissue. In one application of this configuration, the assembly 10 may be passed through a valve (e.g., a mitral valve), such that the hood 12 creates a first open area over the valve. The flap 588 may then support the distal surface of the valve. Accordingly, devices may be advanced through the catheter 16 and to within the open area to perform surgical repair of the valve. In an additional variation, the region between proximal openings 584 and the distal end of the catheter 586 contains a valve (e.g., a one-way valve) to control the flow of fluid (in the case of a one-way valve fluid would only flow in a single direction).

Figure 48C:
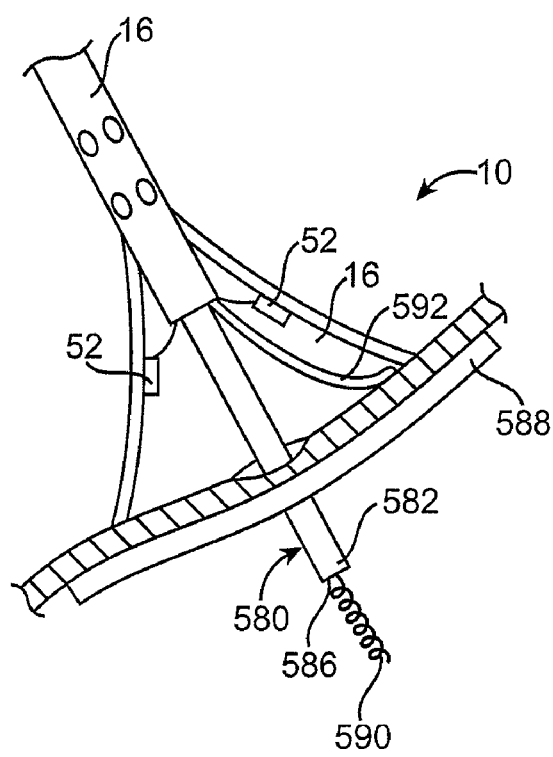
FIGS. 48B-48C show the variation of FIG. 48A with a tissue support flap.
Figure 48B:
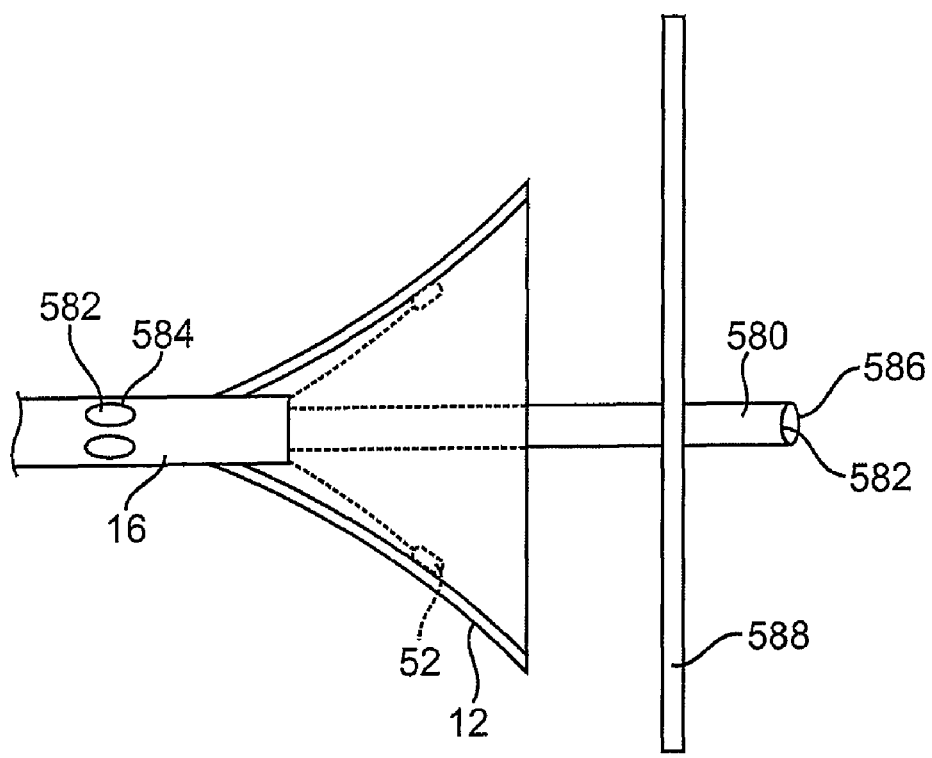

FIG. 48C illustrates a cross-sectional view of the flap 588 placed against a distal surface of tissue (or a valve). As shown, the hood 16 creates an open area over the tissue so that devices 592 may be advanced through the catheter 16 to repair or treat the tissue. As discussed above, the elongate portion 580 may be withdrawn relative to the catheter 16 to secure the tissue between the hood 12 and flap 588. FIG. 48C also illustrates a variation of an assembly 10 where the elongate portion 580 further includes a tissue attachment member 590. In this variation, the tissue attachment member 590 comprises a helical member.

Figure 48D:
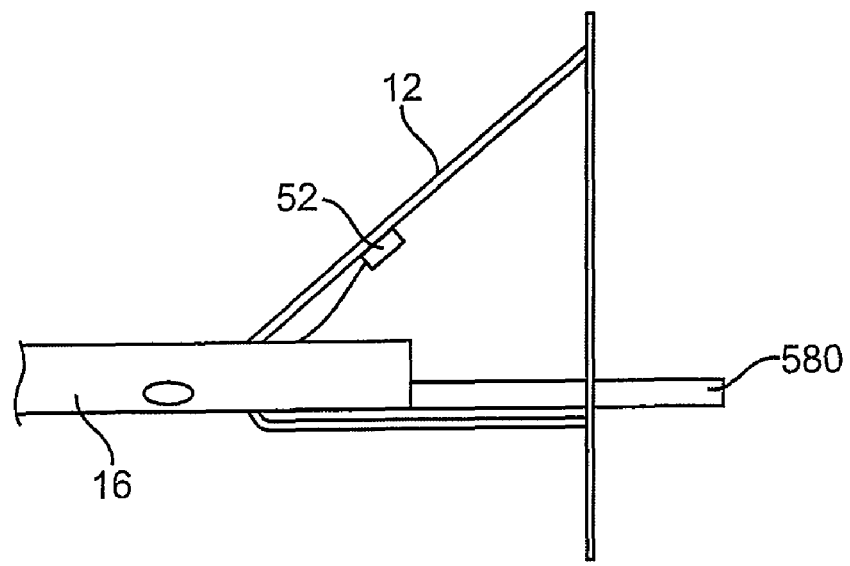
FIG. 48D illustrates an off-center hood located about a catheter.

FIG. 48D illustrates a variation of an assembly 10 according to the present invention where the expanded hood 12 is off-center relative to the catheter 16. Variations include assemblies where the elongate portion 580 is also be off-center relative to the hood 12 when expanded. The visualization element 52 may be placed on a side of the hood 12 to give optimal viewing of the open area. However, the invention also contemplates placement of one or more visualization elements at any location and on any structure within the open area. It is also contemplated that variations of the assembly with an off-set hood configuration, such as that shown in FIG. 48D, may or may not incorporate a support flap as shown in FIGS. 48A-48C.

Figure 48E:
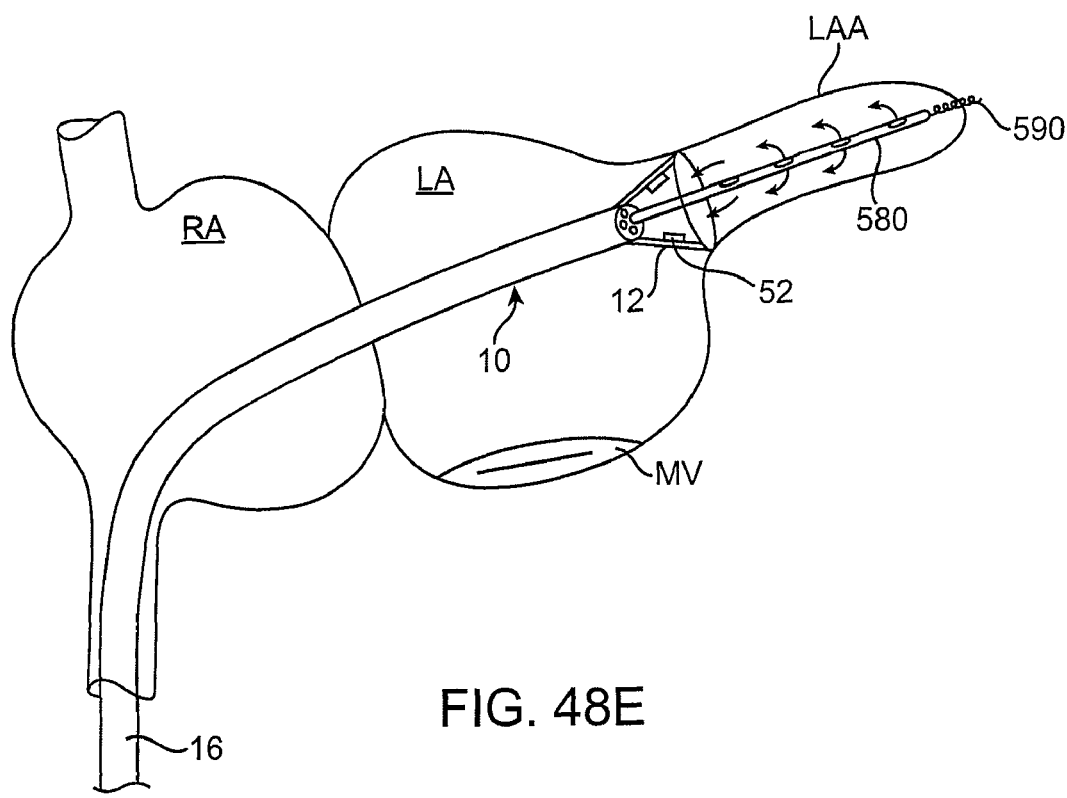
FIG. 48E shows a variation of a tissue imaging and manipulation assembly including an elongate portion that supplies fluid to an area of tissue.

FIG. 48E illustrates another variation of an assembly 10 with an elongate portion 580. In this variation, the elongate portion 580 supplies fluid that is ultimately evacuated through the catheter 16. As shown, as the fluid enters the target site via the elongate portion 580 the hood 12 prevents the fluid from escaping beyond the open area. A lumen in fluid communication with the open area evacuates the fluid and may also aspirate blood located in the left atrial appendage LAA. Such a variation is useful for work in the left atrial appendage LAA. A variation of the assembly 10 may include a tissue attachment member 590 to stabilize the assembly 10 at the target site. In use, the device is advanced through the right atrium RA through the heart wall and into the left atrial appendage LAA in the left atrium LA. The tissue attachment member 590 may be rotated into the tissue to secure the hood 12 and elongate member 580 within the appendage LAA. As noted above, the elongate member 580 may be moveable relative to the catheter 16 and hood 12. Accordingly, pulling the elongate member 580 when the tissue attachment member 590 is coupled to tissue could assist in creating a compressive force between the hood 12 and the opening of the appendage LAA.

Figure 48F:
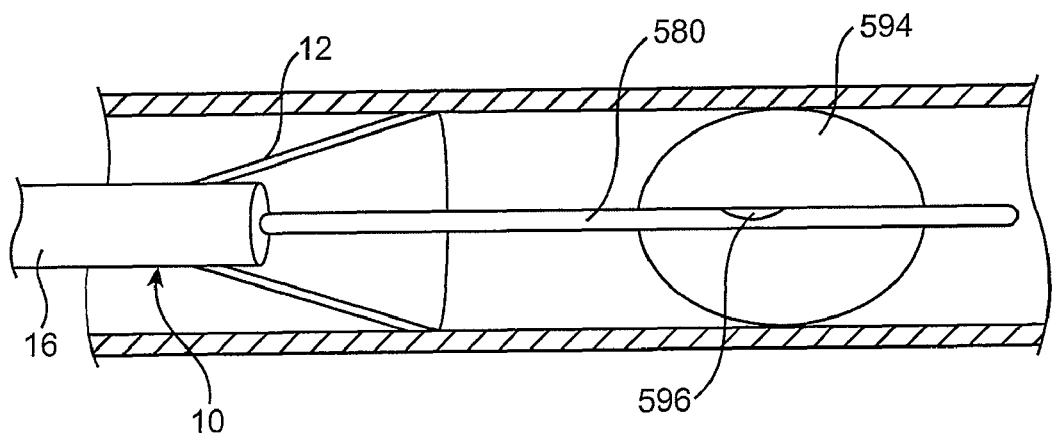
FIG. 48F shows a tissue imaging and manipulation assembly including an occlusion member or balloon.

FIG. 48F illustrates another variation of tissue imaging and manipulation assembly 10. In this variation, the assembly 10 includes an elongate member 580 having a balloon 594 coupled to a balloon lumen 596. The balloon 594 may function as an occlusion balloon. As such, the elongate member 580 may be configured to permit passage of a guidewire or other guiding means. The elongate portion 580 may also be configured to have a bypass lumen as shown in FIG. 48A to allow fluid to move from an area proximally to the hood 12 to an area distally of the balloon.

Figure 49A:
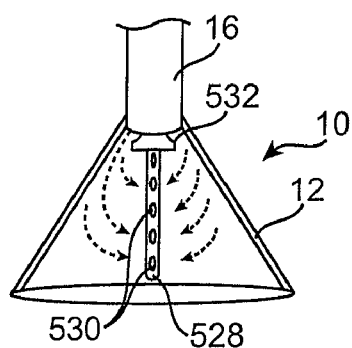
FIG. 49A-49E illustrate the use of an elongate member having a plurality of openings to produce flow patterns within the hood.

FIG. 49A-49E illustrate the use of an elongate member 528 having a plurality of openings 530. FIG. 49A shows an elongate member 528 and openings 530 that act as an irrigator/aspirator to circulate fluid between the catheter 16 and open area of the hood 12. The elongate member may have a tissue attaching member, as discussed herein, attached to a distal end. Moreover, the catheter may have a flow distributor 532 to encourage laminar flow of fluid. Although not illustrated, a pump may be used in any of the described systems to allow the elongate member 528 or catheter 16 to aspirate fluid out of the open area of the hood 12. In variations of the assembly 10, the elongate member 528 may move in and out of the catheter. It should be noted that in any of the variations discussed herein, the flow of fluid may be the reverse of that shown. In such cases, the hood or other structure may require a slight structural change to handle any vacuum forces.

Figure 49B:
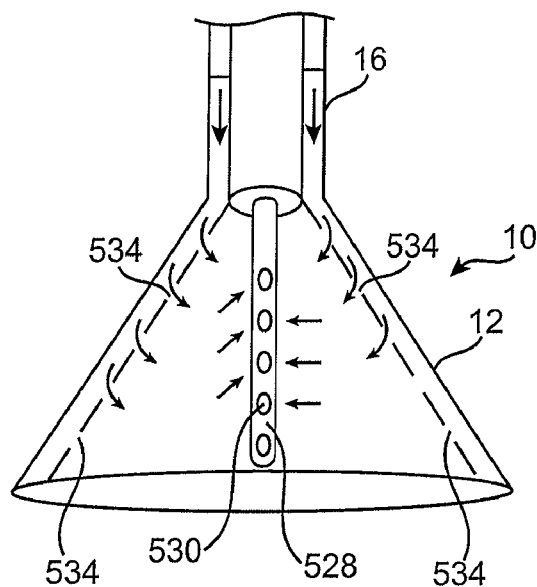
Figure 49C:
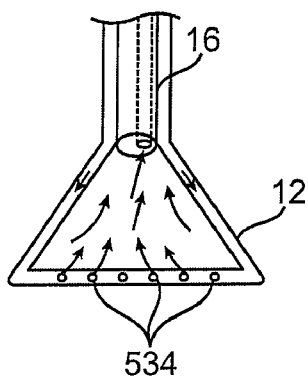

FIG. 49B illustrates another variation of an assembly 10. In this variation, the hood 12 comprises a double layer with a plurality of openings 534 in the interior layer. Accordingly, fluid passes from the catheter 16 into the hood 12 and out of the openings 534. Again, the elongate member 528 draws fluid from within the open area of the hood 12. FIG. 49C illustrates a similar assembly to 49B. However, in this variation, the base of the hood 12 contains the openings 534 that provide fluid into the open area of the hood 12. Fluid returns through the catheter 16.

Figure 49E:
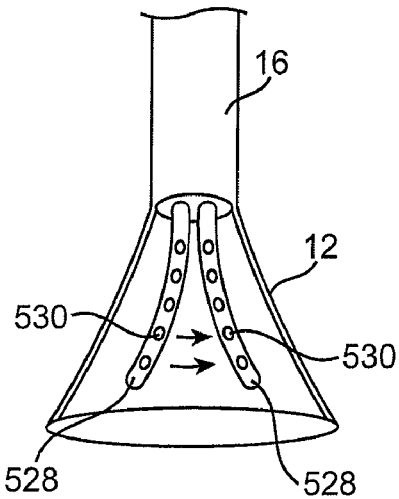
Figure 49D:
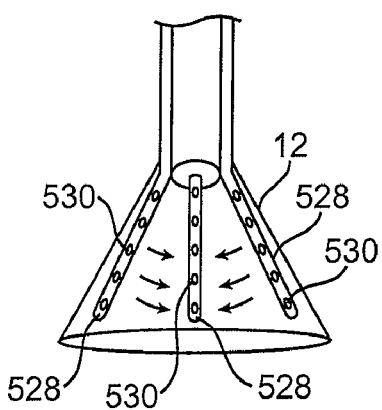

FIG. 49D illustrates another variation of a hood 12 under the present invention. In this variation, the hood 12 includes a plurality of elongate members 528 each having openings 530 that allow for circulation of fluid. One or more of the elongate members 528 are attached to the surface of the hood while a separate elongate member 528 extends through the catheter 16. FIG. 49E illustrates a similar variation where two elongate members 528 extend through the catheter 16 rather than being attached to the hood.

Figure 50A:
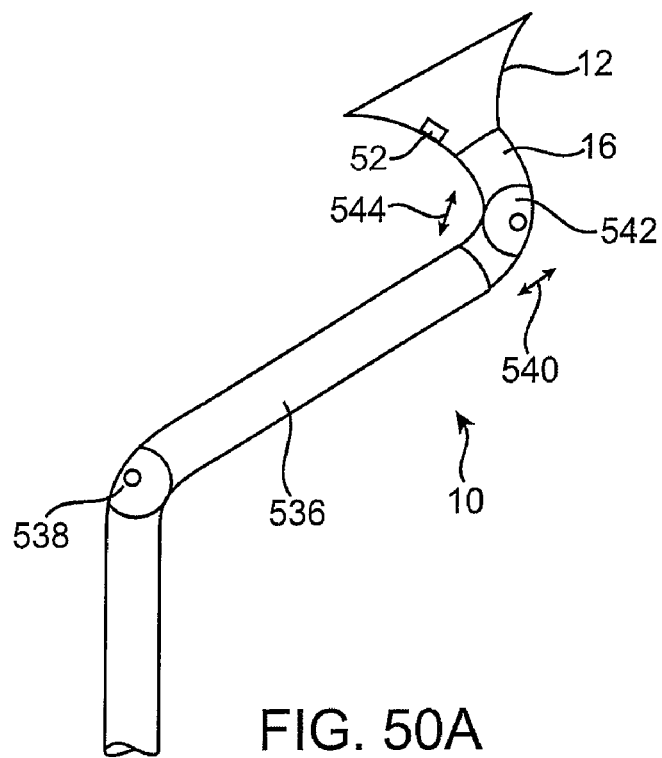
FIGS. 50A-50C illustrate variations of a tissue imaging and manipulation assembly designed to translate or "walk" across tissue surfaces when inserted within the body.
Figure 50B:
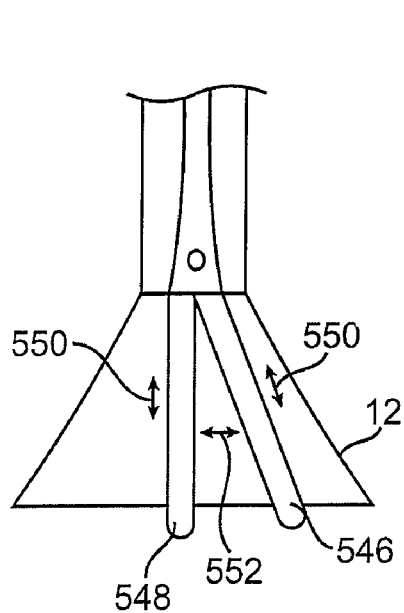
Figure 50C:
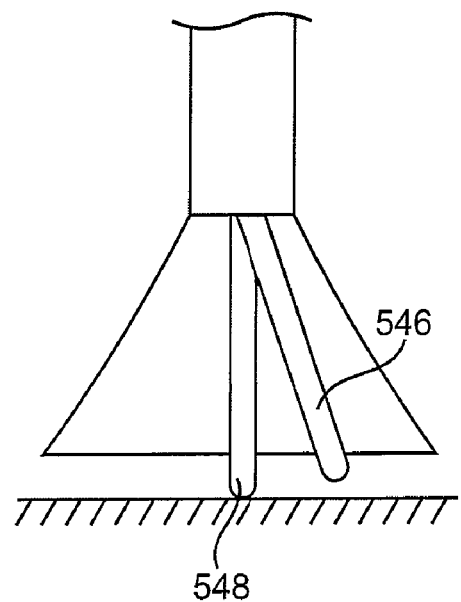

FIGS. 50A-50C illustrate variations of a tissue imaging and manipulation assembly 10 designed to translate or "walk" across tissue surfaces when inserted within the body. In a first variation, the assembly 10 includes an outer sheath 536 having an articulating section or joint 538 allowing for at least one degree of motion. The assembly 10 further includes a catheter 16 being axially moveable, as shown by arrows 540, relative to the sheath 536. The catheter 16 may further include a second joint 542 that allows for angular rotation of the hood 12, as shown by arrows 544. Accordingly, the joints of the assembly 10 allow for repositioning of the hood 12 as it sweeps or walks across tissue.

FIG. 50B illustrates another variation of a tissue imaging and manipulation assembly 10 designed to translate or "walk" across tissue surfaces. In this variation, one or more "fingers" 546, 548 are moveably located within the hood 12. Each finger 546, 548 is designed to move axially relative to the hood 12, as illustrated by arrows 550, as well as angularly relative to the hood 12, as illustrated by arrows 552. Accordingly, as one finger extends beyond the hood 12, the finger 548 raises it off of the tissue surface, as shown in FIG. 50C. Once raised off of the tissue, the second finger 546 advances in the desired direction and extends to contact tissue as the first finger 548 retracts. Thus, this walking motion of the fingers allows for precise movement of the hood across tissue.

The user controls to actuate and control movement are not illustrated but may be those controls conventionally used by medical practitioner. Alternatively, the assembly 10 may be coupled to a robotic manipulation system as described above.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method for imaging an immersed region of tissue, comprising:
   translating a hood projecting distally from a deployment catheter relative to a sheath such that the hood reconfigures from a constrained state within the sheath to an unconstrained state external to the sheath;
   positioning an opening defined by the hood against or adjacent to the region of tissue to be imaged;
   urging a translucent fluid into the hood via the deployment catheter such that an opaque fluid is displaced from within the hood and is purged through the opening to an environment external to the hood while the opening is maintained against the region of tissue; and
   visualizing the region of tissue through the translucent fluid via a visualization element positioned on the hood within or adjacent to an open area defined by the hood such that the element is in fluid communication through the opening with the environment, where the visualization element is moved out of alignment with the deployment catheter when in the constrained state to an off-axis position relative to a longitudinal axis of the deployment catheter when in the unconstrained state.

2. The method of claim 1 wherein positioning an opening defined by the hood comprises advancing the deployment catheter intravascularly into a chamber of a heart.

3. The method of claim 1 wherein translating comprises deploying the hood from a low-profile delivery configuration into an expanded deployed configuration.

4. The method of claim 1 wherein positioning an opening defined by the hood comprises steering the deployment catheter to the region of tissue.

5. The method of claim 1 wherein positioning an opening defined by the hood comprises stabilizing a position of the hood relative to the tissue.

6. The method of claim 1 wherein urging a translucent fluid comprises pumping the translucent fluid into the hood through a fluid delivery lumen defined through the deployment catheter.

7. The method of claim 6 wherein urging a translucent fluid comprises urging saline, plasma, water, or perfluorinated liquid into the hood such that blood is displaced from the hood.

8. The method of claim 1 wherein visualizing the region of tissue further comprises illuminating the region of tissue.

9. The method of claim 1 further comprising treating the region of tissue with a therapeutic tool advanced through the deployment catheter.

10. The method of claim 1 further comprising repositioning the hood to a second region of tissue to be imaged.

11. The method of claim 9 wherein treating the region comprises advancing a guidewire into or through the hood.

12. The method of claim 11 further comprising guiding a movement of the hood via the guidewire.

13. The method of claim 1 wherein urging a translucent fluid comprises introducing the fluid through at least one lumen defined through the catheter.

14. The method of claim 1 wherein urging a translucent fluid comprises controlling a flow rate of the fluid into the hood via a processor.

15. The method of claim 1 wherein visualizing the region of tissue comprises recording a location of the region of tissue via a processor.

16. The method of claim 1 wherein visualizing the region of tissue comprises recording an image of the region of tissue via a processor.

17. The method of claim 1 wherein the hood reconfigures from a constrained state within the sheath to the unconstrained state external to the sheath by elastically self-expanding.

18. The method of claim 1 wherein the visualization element comprises at least one optical fiber, CCD imager, or CMOS imager.

19. The method of claim 1 wherein visualizing further comprises illuminating the open area.

20. The method of claim 19 wherein illuminating comprises illuminating the open area via one or more light emitting diodes.

21. The method of claim 1 wherein translating a hood comprises translating a non-inflatable membrane which defines the open area of the hood.

* * * * *